United States Patent
Egholm et al.

(10) Patent No.: US 6,451,968 B1
(45) Date of Patent: Sep. 17, 2002

(54) PEPTIDE NUCLEIC ACIDS

(75) Inventors: Michael Egholm, Lexington, MA (US); Peter Nielsen, Kokkedal (DK); Ole Buchardt, deceased, late of Vaerlose (DK), by Dorte Buchardt, heiress; Kim L. Dueholm, Kokkedal; Leif Christensen, Valby, both of (DK); James M. Coull, Westford, MA (US); John Kiely; Michael Griffith, both of San Diego, CA (US)

(73) Assignees: ISIS Pharmaceuticals, Inc., Carlsbad, CA (US); Perseptive Biosystems, Inc., Framingham, MA (US)

( * ) Notice: Subject to any disclaimer, the term of this patent is extended or adjusted under 35 U.S.C. 154(b) by 0 days.

(21) Appl. No.: 08/275,951

(22) Filed: Jul. 15, 1994

Related U.S. Application Data

(63) Continuation-in-part of application No. 08/108,591, filed as application No. PCT/EP92/01219 on May 22, 1992, and a continuation-in-part of application No. 08/088,658, filed on Jul. 2, 1993, now Pat. No. 5,641,625, and a continuation-in-part of application No. 08/088,661, filed on Jul. 2, 1993, now Pat. No. 6,228,982.

(30) Foreign Application Priority Data

| May 24, 1991 | (DK) | ................................................. 986/91 |
| May 24, 1991 | (DK) | ................................................. 987/91 |
| Apr. 15, 1992 | (DK) | ................................................. 510/92 |

(51) Int. Cl.[7] .................. C07H 21/00; A61K 38/00; C12Q 1/68

(52) U.S. Cl. ................ 530/300; 435/6; 436/501; 536/22.1

(58) Field of Search ............ 435/6, 810; 436/501; 530/350, 300; 536/22.1, 23.1, 24.1, 24.3–24.33; 935/77, 78

(56) References Cited

U.S. PATENT DOCUMENTS

| 5,134,066 A | | 7/1992 | Rogers et al. ................. 435/91 |
| 5,142,047 A | | 8/1992 | Summerton et al. ......... 544/118 |
| 5,166,315 A | | 11/1992 | Summerton et al. ......... 528/406 |
| 5,324,483 A | | 6/1994 | Cody et al. .................. 422/131 |
| 5,539,082 A | * | 7/1996 | Nielsen et al. ............... 530/300 |
| 5,773,571 A | * | 6/1998 | Nielsen et al. ............... 530/300 |

FOREIGN PATENT DOCUMENTS

| EP | 0 410 280 A1 | 7/1989 |
| WO | WO 86/05518 | 9/1986 |
| WO | WO 86/05519 | 9/1986 |
| WO | WO 90/02749 | 3/1990 |
| WO | WO 92/20702 | 11/1992 |
| WO | WO 92/20703 | 11/1992 |
| WO | WO 93/05180 | 3/1993 |
| WO | WO 93/12129 | 6/1993 |
| WO | WO 93/18187 | 9/1993 |
| WO | WO 94/05268 | 3/1994 |
| WO | WO 94/13326 | 6/1994 |

OTHER PUBLICATIONS

Switzer et al., Biochemistry, vol. 32, No. 39, pp. 10489–10496, 1993.*

(List continued on next page.)

Primary Examiner—Ardin H. Marschel
(74) Attorney, Agent, or Firm—Woodcock Washburn LLP

(57) ABSTRACT

Novel peptide nucleic acids and novel linked peptide nucleic acids, form triple stranded structures with nucleic acids. The peptide nucleic acids include ligands such as naturally occurring nucleobases attached to a peptide backbone through a suitable linker. Other nucleobases including C-pyrimidines and iso-pyrimidines can be used as the ligands in Hoogsteen strands to increase binding affinity. Two peptide nucleic acid strands are joined together with a linker to form a bis-peptide nucleic acid. The individual strands of the peptide nucleic acids in the bis compounds can be orientated either parallel or antiparallel to each other.

26 Claims, 4 Drawing Sheets

OTHER PUBLICATIONS

Affinity Chromatography—A Practical Approach, P.D.g. Dean, W.S. Johnson and F.A. Middle, eds., IRL Press Ltd., Oxford 1986.

Anderson et al., "t–Butyloxycarbonylamino Acids and Their Use in Peptide Synthesis", *J. Am. Chem. Soc.* 1957, 79, 6180–6183.

Atherton et al., "A Physically Supported Gel Polymer for Low Pressure, Continuous Flow Solid Phase Reactions. Application to Solid Phase Peptide Synthesis", *J. Chem. Soc. Chem. Commun* 1981, 1151–1152.

Atherton et al., "Polyamide Supports for Polypeptide Synthesis", *J. Am. Chem. Soc* 1975, 50, 6584–6585.

Atherton et al., "Peptide Synthesis. Part 2. Procedures for solid–phase Synthesis Using $N^\alpha$–Fluorenylmethoxycarbonylamino–acids on Polyamide Supports. Synthesis of Substance P and of Acyl Carrier Protein 65–74 Decapeptide", *J.C.S. Perkin* 1981, I, 538–546.

Atherton, E. et al., "The Polyamide Method of Solid Phase Peptide and Oligonucleotide Synthesis" *Bioorg. Chem.* 1979, 8, 351–370.

Barany et al., "Solid–phase Peptide Synthesis: a Silver Anniversary Report", *Int. J. Peptide Protein Res.* 1987, 30, 705–739.

Barany and Merrified in "The Peptides" vol. 2, Academic Press, N.Y., 1979, pp. 1–284.

Barany et al., "A New Amino Protecting Group Removable by Reduction. Chemistry of the Dithiasuccinoyl (Dts) Function", *J. Am. Chem. Soc.* 1977, 99, 7363–7365.

Barton et al., "Solid–Phase Synthesis of Selectively Protected Peptides for Use as Building Units in the Solid–Phase Synthesis of Large Molecules", *J. Am. Chem. Soc.* 1973, 95, 4501–4506.

Bayer and Jung, "A New Support for Polypeptide Synthesis in Columns", *Tetrahedron Lett* 1970, 51, 4503–4505.

Beaucage and Caruthers, "Deoxynucleoside Phosphoramidites–A New Class of Key Intermediates for Deoxypolynucleotide Synthesis" *Tetrahedron Lett.*, 1981, 22, 1859–1862.

Beran, Miloŝ et al., "Substituted ω–(4–Oxo–3, 4–Dihydro–5–Pyrimidinyl) Alkanoic Acids, Their Derivatives and Analogues" *Collect. Czech. Chem. Commun.* 1983, 48, 292–298.

Berg et al., "Long–Chain Polystyrene–Grafted Polyethylene Film Matrix: A New Support for Solid–Phase Peptide Synthesis", *J. Am. Chem. Soc* 1989, 111, 8024–8026.

Bodánzsky, "Synthesis of Peptides by Aminolysis of Nitrophenyl Esters", *Nature* 1955, 175, 685.

Bodanszky et al., "Active Esters and Resins in Peptide Synthesis", *Chem. Ind.* 1964, 1423–1424.

Bodanzsky, "Principles of Peptide Synthesis", Springer Verlag, Berlin–New York 1984.

Brady et al., "Some Novel, Acid–Labile Amine Protecting Groups", *J. Org. Chem.* 1977, 42, 143–146.

Carpino, "New Amino–Protecting Groups in Organic Synthesis", *Acc. Chem. Res.* 1973, 6, 191–198.

Carpino and Han, "The 9–Fluorenylmethoxycarbonyl Amino–Protecting Group" *J. Org. Chem.*, 1972, 37, 3404–3409.

Carpino, "Oxidative Reactions of Hydrazines. IV. Elimination of Nitrogen from 1,1–Disubstituted–2–arenesulfonhydrazides[1–4]", *J. Am. Chem. Soc.* 1957, 79, 4427–4431.

Carpino and Han, "The 9–Fluorenylmethoxycarbonyl Function, a New Base–Sensitive Amino–Protecting Group", *J. Am. Chem. Soc.* 1970, 92, 5748–5749.

Carpino et al., "( (9–Fluorenylmethyl) oxy) carbonyl (FMOC) Amino Acid Fluorides. Convenient New Peptide Coupling Reagents Applicable to the FMOC/tert–Butyl Strategy for Solution and Solid–Phase Syntheses", *J. Am. Chem. Soc.* 1990, 112, 9651–9652.

Caruthers, Marvin H., "Gene Synthesis Machines: DNA Chemistry and Its Uses" *Science*, 1985, 230, 281–285.

Daniels et al., "Membranes as Solid Supports for Peptide Synthesis", *Tetrahedron Lett.* 1989, 30, 4345–4348.

Egholm, et al., "Recognition of Guanine and Adenine in DNA by Cytosine and Thymine Containing Peptide Nucleic Acids (PNA)[1,2]" *J. Am. Chem. Soc.*, 1992, 114, 9677–9678.

Egholm et al., "Peptide Nucleic Acids (PNA). Oligonucleotide Analogues with an Achiral Peptide Backbone" *J. Am. Chem. Soc.* 1992, 114, 1895–1897.

Eichler et al., "Application of Cellulose Paper as Support Material in Simultaneous Solid Phase Peptide Synthesis", *Collect. Czech. Chem. Commun.* 1989, 54, 1746–1752.

Fissekis, John D. and Sweet, Frederick, "Synthesis of 5–Carboxymethyluridine. A Nucleoside form Transfer Ribonucleic Acid" *Biochemistry* 1970, 9, 3136–3142.

Fodor, Stephen P.A. et al., "Light–Directed, Spatially Addressable Parallel Chemical Synthesis" *Science*, 1991, 251, 767–773.

Fridkin et al., "A Synthesis of Cyclic Peptides Utilizing High Molecular Weight Carriers", *J. Am. Chem. Soc* 1965, 87, 4646–4648.

Geysen et al., "Use of Peptide Synthesis to Probe Viral Antigens for Epitopes to a Resolution of a Single Amino Acid", *Proc. Natl. Acad. Sci. USA* 1984, 81: 3998–4002.

Gilham, P. T., "The Covalent Binding of Nucleotides, Polynucleotides, and Nucleic Acids to Cellulose" in *Methods in Enzymology*, Chapter 10, L. Grossmann and K. Moldave, eds. 1971, 21, part D, 191–197, Academic Press, N.Y. and London.

Goodman and Levine, "Peptide Synthesis via Active Esters. IV. Racemization and Ring–Opening Reactions of Optically Active Oxazolones", *J. Am. Chem. Soc.* 1964, 86, 2918–2922.

Gorman, Jeffrey, "An Apparatus for Simultaneous Manual Solid–Phase Synthesis of Multiple Peptide Analogs", *Anal. Biochem* 1984 136 397–406.

Hahn et al., "Design and Synthesis of a Peptide Having Chymotrypsin–Like Esterase Activity", *Science* 1990, 248, 1544–1547.

Haas, W.L. et al., "Adamantyloxycarbonyl, a New Blocking Group. Preparation of 1–Adamantyl Chloroformate" *J. Am. Chem. Soc.* 1966, 88, 1988–1992.

Heimer, J.P. et al., "Synthesis of Analogs and Oligomers of N– (2–aminoethyl) glycine and Their Gastrointestinal Absorption in the Rat" *Int. J. Pept. Protein Res.*, 1984, 23, 203–211.

Holm and Meldal, "Multiple Column Peptide Synthesis", Proceedings of the 20th European Peptide Symposium, G. Jung and E. Bayer, eds., Walter de Gruyter & Co., Berlin: 1989, 208–210.

Houghten, "General Method for the Rapid Solid–Phase Synthesis of Large Numbers of Peptides: Specificity of Antigen–Antibody Interaction at the Level of Individual Amino Acids", *Proc. Natl. Acad. Sci. USA* 1985, 82, 5131–5135.

Jones, Jr., "Hydrogeneration of Protected Leucine Enkephalin from a Resin During Solid Phase Synthesis", *Tetrahedron Lett.* 1977, 33, 2853–2856.

Kent and Merrifield, "Preparation and Properties of tert–Butyloxycarbonylaminoacyl–4– (oxymethyl) phenylacetamidomethyl–(Kel F–g–styrene) Resin, an Insoluble, Noncrosslinked Support for Solid Phase Peptide Synthesis", *Israel J. Chem* 1978, 17, 243–247.

König and Geiger, "Racemisierung bei Peptidsynthesen", *Chem. Ber.* 1970, 103, 2024–2033.

König and Geiger, "Eine Neue Methode Zur Synthese Von Peptiden: Aktivierung Der Carboxylgruppe Mit Dicyclohexylcarbodiimid Und 3 –Hydroxy–4 –oxo–3.4–dihydro–1.2.3–benzotriazin", *Chem. Ber.* 1970, 103, 2034–2040.

Kovacs, J. et al., "Glutamic and Aspartic Anhydrides. Rearrangement of N–Carboxyglutamic 1,5–Anhydride to the Leuchs' Anhydride and Conversion of the Latter to Pyroglutamic Acid" *J. Am. Chem. Soc.* 1963 85: 1839–1844.

Krchňák et al., "Continuous–Flow Solid–Phase Peptide Synthesis", *Tetrahedron Lett* 1987, 28, 4469–4472.

Krchňák et al., "Multiple Continuous–Flow Solid Phase Peptide Synthesis", *Int. J. Peptide Protein Res.* 1989, 33, 209–213.

Kupryszewski, "O Estrach Chlorofenylowych Aminokwasow. II. Synteza Peptydow Poprzez Aminolize Aktywnych Estrow 2,4,6–Trojchlorofenylowych N–Chronionych Aminokwasow", *Rocz. Chem.* 1961, 35, 595–600.

Lebl, Michal and Eichler, Jutta, "Simulation of Continuous Solid Phase Synthesis: Synthesis of Methionine Enkephalin and its Analogs", *Peptide Research*, 1989, 2, 297–300.

Letsinger, et al., "Synthesis of Thymidine Oligonucleotides by Phosphite Triester Intermediates" *J. Am. Chem. Soc.* 1976, 98, 3655–3661.

Li et al., "The Synthesis of a Protein Possessing Growth-Promoting and Lactogenic Activities", *J. Am. Chem. Soc.* 1970, 92, 7608–7609.

McKay and Albertson, "New Amine–Masking Groups for Peptide Synthesis", *J. Am. Chem. Soc.* 1957, 79, 4686–4690.

Merrifield, "Solid Phase Peptide Synthesis. I. The Synthesis of a Tetrapeptide", *J. Am. Chem. Soc.* 1963, 85, 2149–2154.

Merrifield, "Solid Phase Synthesis", *Science* 1986, 232, 341–347.

Mitchell and Merrifield, "Occurrence of N–Alkylation During the Acidolytic Cleavage of Urethane Protecting Groups[1a,b]", *J. Org. Chem.* 1976, 41, 2015–2019.

Mitchell et al., "Preparation of Aminomethyl–Polystyrene Resin by Direct Amidomethylation", *Tetrahedron Lett.* 1976, 42, 3795–3798.

Mizutani, Takaharu and Tachibana, Yoshio, "Oligo (dT)—glyceryl Porous Glass, a Better Support for the Preparation of mRNA" *J. Chromatogr*, 1986, 356, 202–205.

Mutter and Bayer, "Rapid Procedure for Liquid–Phase Peptide Synthesis: The Crystallization Method", *Angew. Chem., Int. Ed. Engl.* 1974, 13, 88–89.

Nefkens and Tesser, "A Novel Activated Ester in Peptide Synthesis" *J. Am. Chem. Soc.* 1961, 83, 1263.

"Nucleic Acid Hybridization—A Practical Approach", B. D. Harnes and S. J. Higgins, IRL Press Ltd., Oxford 1987.

Odian, "Principles of Polymerization", McGraw–Hill, N.Y. 1970.

Ono, A. et al., "Triplex Formation of Oligonucleotides Containing 2'–O–Methylpseudoisocytidine in Substitution for 2'–Deoxycytidine" *J. Am. Chem. Soc.* 1991, 113, 4032–4033.

Ono, Akira et al., "Triplex Formation of an Oligonucleotide Containing 2'–O–Methylpseudoisocytidine with a DNA Duplex at Neutral pH" *J. Org. Chem.* 1992, 57, 3225–3230.

Parr and Grohmann, "Solid–Phase Peptide Synthesis on an Inorganic Matrix having Organic Groups on the Surface", *Angew. Chem. Internal. Ed.* 1972, 11, 314–315.

Petty et al., "Cytochrome Oxidase Models. 2. $\mu$–Bipyrimidyl Mixed–Metal Complexes as Synthetic Models for the Fe/Cu Binuclear Active Site of Cytochrome Oxidase", *J. Am. Chem. Soc.* 1980, 102, 611–620.

Pietta and Marshall, "Amide Protection and Amide Supports in Solid–Phase Peptide Synthesis" *Chemical Communications*, 1970, 650–651.

Pless et al., Über die Geschwindigkeit der Aminolyse von Verschiedenen Neuen, Aktivierten, N–geschützten α–Aminosäure–phenylestern, insbesondere 2,4,5–Trichlorphenylestern) *Helv. Chim. Acta* 1963, 46, 1609–1625.

Pollack, S. J. et al., "Selective Chemical Catalysis by an Antibody" *Science*, 1986, 234, 1570–1573.

Rich and Gurwara, "Preparation of a New o–Nitrobenzyl Resin for Solid–Phase Synthesis of tert–Butyloxycarbonyl––Protected Peptide Acids", *J. Am. Chem. Soc.* 1975, 97, 1575–1579.

Rivaille et al., "Synthesis of LH–RH Using a New Phenolic Polymer as Solid Support and "BOP" Reagent for Fragment Coupling", *Tetrahedron* 1980, 36, 3413–3419.

Sakakibara, et al., "A New Method for Releasing Oxytocin from Fully–Protected Nona–peptides Using Anhydrous Hydrogen Fluoride" *Bull. Chem. Soc. Jpn.* 1965, 38, 1412–1413.

Schlatter, James M. and Mazur, Robert H., "Hydrogenation in Solid Phase Peptide Synthesis. I. Removal of Product from the Resin" Tet. Letts. 1977 33: 2851–2852.

Scott et al., "The Use of Resin Coated Glass Beads in the Form of a Packed Bed for the Solid Phase Synthesis of Peptides", *J. Chromatogr. Sci* 1971, 9, 577–591.

Sheehan, "A New Method of Forming Peptide Bonds", *J. Am. Chem. Soc.* 1955, 77, 1067–1068.

Shemyakin et al., "Synthesis of Peptides in Solution on a Polymeric Support I. Synthesis of Glycylglycyl—L—Leucylglycine", *Tetrahedron Lett* 1965, 27, 2323–2327.

Shokat et al., "A New Strategy for the Generation of Catalytic Antibodies", *Nature* 1989, 338, 269–271.

Sieber and Iselin, "77. Selektive Acidolytische Spaltung von Aralkyloxycarbonyl—Aminoschutzgruppen", *Helv. Chem. Acta.* 1968, 51, 614–622.

Solid–Phase Biochemistry —Analytical and Synthetic Aspects, W.H. Scouten, ed., John Wiley & Sons, N. Y., 1983.

Stewart and Young, "Solid Phase Peptide Synthesis", 2nd Ed., Pierce Chemical Company, Ill., 1984.

Tam, James P., "A Gradative Deprotection Strategy for the Solid–Phase Synthesis of Peptide Amides Using p–(Acyloxy) benzhydrylamine Resin and the $S_N2$ Deprotection Method", *J. Org. Chem.* 1985 50 5291–5298.

Tam et al., "Multi–Detachable Resin Supports for Solid Phase Fragment Synthesis", *Tetrahedron Lett.* 1979, 51, 4935–4938. Tam et al., "$S_N2$ Deprotection of Synthetic Peptides with a Low Concentration of HF in Dimethyl Sulfide: Evidence and Application in Peptide Synthesis", *J. Am. Chem. Soc.* 1983, 105, 6442–6455.

Tam et al., "Improved Synthesis of 4–(Boc–aminoacyloxymethyl)–phenylacetic Acids for Use in Solid Phase Peptide Synthesis", *Communications* 1979, 955–957.

Tam et al., "Mechanisms for the Removal of Benzyl Protecting Groups in Synthetic Peptides by Trifluoromethanesulfonic Acid–Trifluoroacetic Acid–Dimethyl Sulfide", *J. Am. Chem. Soc.* 1986, 108, 5242–5251.

Tramontano et al., "Catalytic Antibodies", *Science* 1986, 234, 1566–1570.

Tramane, T.L. et al., "A Proposed Model for Triplex Formation at Single–Stranded Nucleic Acid Target Sites of Unrestricted Sequence", Abstracts Conference on Nucleic Acids Medical Applications, Cancun, Mexico, Jan. 1993.

Trapane, T. et al., "Formation of a purine–purine–pyrimidine triplex with purine oligomers having non–ionic methylphosphonate linkages" *Abstract of J. Biomol. Strul. Struct.*, 1991, 8, from "Seventh Conversation in Biomolecular Stereodynamics" 229.

Trapane, T.L. and Ts'o, P.O.P., "Triplex Formation of Adenine and Thymine Deoxyoligonucleotides and Their Nonionic Methylphosphonate Analogs" *Biophys. J.*, 1992, 61, Abstract 2437.

Tregear, "Graft Copolymers as Insoluble Supports in Peptide Synthesis", *Chemistry and Biology of Peptides* 1972, J. Meienhofer, ed., Ann Arbor Sci. Publ., Ann Arbor, 175–178.

van Rietschoten, "Simultaneous Synthesis of Two Peptide Analogs on Different Insoluble Supports", *Peptides 1974* 1975, Y. Wolman, Ed., Wiley and Sons, New York, pp. 113–116.

Wieland et al., "Symmetrical Boc–Amino Acid Anhydrides for Economical Peptide Syntheses on a Solid Phase", *Angew. Chem., Int. Ed. Engl.* 1971, 10, 336.

Yajima et al., "Trifluoromethanesulphonic Acid, as a Deprotecting Reagent in Peptide Chemistry", *J. Chem. Soc., Chem. Comm.* 1974, 107–108.

Zervas et al., "New Methods in Peptide Synthesis. I. Tritylsulfenyl and o–Nitrophenylsulfenyl Groups as N–Protecting Groups", *J. Am. Chem. Soc.* 1963, 85, 3660–3666.

McCurdy, et al., "Deoxyoligonucleotides with Inverted Polarity: Synthesis and Use in Triple–Helix Formation," *Nucleosides and Nucleotides* 1991, 10, 287–290.

Nielsen, et al., "Sequence–Selective Recognition of DNA by Strand Displacement with a Thymine–Substituted Polyamide," *Science*, 254:1497–1500, 1991.

Froehler, et al., "Oligodeoxynucleotides Containing C–5 Propyne Analogs of 2'–Deoxyuridine and 2'–Deoxycytidine," *Tetrahedron Letters* 1992, 33, 5307–5310.

Sági, et al., "Base–Modified Oligodeoxynucleotides. I. Effect of 5–Alkyl, 5– (1–Alkenyl) and 5– (1–Alkynyl) Substitution of the Pyrimidines on Duplex Stability and Hydrophobicity," *Tetrahedron Letters* 1993, 34, 2191–2194.

Spalholtz et al., "Bovine Papillomavirus Transcriptional Regulation: Localization of the E2—Responsive Elements of the Long Control Region," *J. Virol.* 1987, 61, 2128–2137.

Dubochet et al., "A New Preparation Method for Dark–Field Electron Microscopy of Biomacromolecules," *J. Ultrastruct. Res.* 1971, 35, 147–167.

Vickers, T. et al., "Inhibition of HIV–LTR gen expression by oligonucleotides targeted to the TAR element," *Nucleic Acids Research* 1991, 19, 3359–3368.

Stenberg et. al., "Promoter–Specific trans Activation and Repression by Human Cytomegalovirus Immediate–Early Proteins Invovles Common and Unique Protein Domains," *J. Virol.* 1990, 64, 1556–1565.

Hahn et al., "Molecular cloning and characterization of the HTLV–III virus associated with AIDS," *Nature* 1984, 312, 166–169.

Depto et al., "Regulated Expression of the Human Cytomegalovirus pp65 Gene: Octamer Sequence in the Promoter Is Required for Activation by Viral Gene Products," *J. Virol.* 1989, 63, 1232–1238.

Tibanyenda et al., "The effect of single base–pair mismatches on the duplex stability of d(T–A–TT–A–A–T–A–T––C–A–A–G–T–T–G) . d(C–A–A–C–TT–G–A–T–A–T––T–A–A–T–A)," *Eur. J. Biochem.* 1984, 139, 19–27.

Vasseur et al., "Oligonucleosides: Synthesis of a Novel Methylhydroxylamine–Linked Nucleoside Dimer and Its Incorporation into Antisense Sequences," *J. Am. Chem. Soc.* 1992, 114, 4006–4007.

Lal et al., "Diphenylphosphoryl Azide A Novel Reagent for the Stereospecific Synthesis of Azides from Alcohols," *Tetrahedron Letters* 1977, 23, 1977–1980.

Demidov, V. et al., "Sequence Selective Double Strand DNA Cleavage by Peptide Nucleic Acid (PNA) Targeting Using Nuclease S1" *Nucl. Acids Res.* 1993 21(19), 2103–2107.

Egholm, M. et al., "Peptide Nucleic Acids Containing Adenine and Guanine Recognize Thymine and Cytosine in Complementary DNA Sequences" *J. Chem. Soc. Chem. Commun.* 1993 800–801.

Mack, D. P. et al., "Design and Chemical Synthesis of a Sequence–Specific DNA–Cleaving Protein" *J. of Am. Chem. Soc.*, 1988 110 7572–7574.

Wakelin, L. P.G. et al., "Kinetic and Equilibrium Binding Studies of Amsacrine–4–Carboxamides: A Class of Asymmetrical DNA–Intercalating Agents which Bind by Threading Through the DNA Helix" *J. Med. Chem* 1990, 33, 2039–2044.

Nielsen, P. E. et al., "Photochemical Cleavage for DNA by Nitrobenzamides" *Biochem.* 1988, 27, 6338–6343.

Blackwell, T. K. et al., "Sequence–Specific DNA Binding by the c–Myc Protein," *Science* 1990, 250, 1149–1151.

Cullen, B., "The HIV–1 Tat Protein: An RNA Sequence–Specific Processivity Factor?" *Cell* 1990 63, 655–657.

Eckstein, ed., *Oligonucleotides and Analogues, A Practical Approach*, IRL Press, 1991.

Franza, Jr., B. R. et al., "Characterization of cellular proteins recognizing the HIV enhancer using a microscale DNA–affinity precipitation assay," *Nature* 1987, 330, 391–395.

Gait, ed., *Oligonucleotide Synthesis, A Practical Approach*, IRL Press, 1984.

Gilmore, T. D. and Temin, H. M., "Different Localization of the Product of the v–rel Oncogene in Chicken Fibroplasts and Spleen Cells Correlates with Transformation by REV–T", *Cell* 1986 44 791–800.

König, H. et al., "Autoregulation of fos: the Dyad Symmetry Element as the Major Target of Repression," *EMBO Journal* 1989, 8, 2559–2566.

Nisen, P. D. et al., "Enhanced Expression of the N–myc Gene in Wilms' Tumors," *Cancer Research* 1986, 46, 6217–6222.

Akashi, et al., "New Aspects of Polymer Drugs", *Adv. Polym. Sci.* 1990, 97, 108–146.

Buttrey et al., "Synthetic Analogues of Polynucleotides–XIII: The Resolution of DL–β– (Thymin–1–YL) Alanine and Polymerisation of the β– (Thymin–1–YL) Alanines", *Tetrahedron* 1975, 31, 73–75.

De Konig et al., "Unconventioanl Nucleotide Analogues V. Derivatives of 6– (1–pyrimidinyl) –and 6– (9–purinyl) –2– aminocaproic acid.", *Recueil* 1971, 90, 874–884.

Doel et al., "An Approach to the Synthesis of Peptide Analogues of Oligonucleotides (Nucleopeptides)", *Tetrahedron Letters* 1969, 27, 2285–2288.

Doel et al., "The Synthesis of Peptides Containing Purine and Pyrimidine Derivatives of DL–Alanine", *Tetrahedron* 1974, 30, 2755–2759.

Hanvey et al., "Antisense and Antigene Properties of Peptide Nucleic Acids", *Science* 1992, 258, 1481–1485.

Huang et al., "Acyclic Nucleic Acid Analogues: Synthesis and Oligomerization of γ, 4–Diamino–2–oxo–1 (2H) –pyrimidinepentanoic Acid and δ 4–Diamino–2–oxo–1 (2H) –pyrimidinehexanoic Acid", *J. Org. Chem.* 1991, 56, 6007–6018.

Inaki et al., "Functionality and Applicability of Synthetic Nucleic Acid Analogs", *in Current Topics in Polymer Science* 1987, Ottenbrite, Utracki, Inoue, Eds. New York : Macmillan Pub. Co., 1, 80–100.

Inaki, Y., "Synthetic Nucleic Acid Analogs", *Prog. Polym. Sci.* 1992, 17, 515–570.

Lu et al., "Synthesis of Polyesters Containing Nucleic Acid Base Derivatives as Pending Side Chains," *J. Polym. Sci.* 1986, Part A: *Polymer Chemistry* 24: 525–536.

Nagae et al., "Functional Monomers and Polymers. CLIV. Application of Nucleic Acid Base Containing Polymers to High Performance Liquid Chromatography," *J. Polym. Sci.: Part A: Polymer Chemistry* 1989, 27, 2593–2609.

Nollet et al., "Unconventional Nucleotide Analogues–III, 4– ($N_1$–Pyrimidyl) –2–Aminobutyric Acids", *Tetrahedron* 1968, 25, 5989–5994.

Nollet et al., "Unconventional Nucleotide Analogues–I, $N_9$–Purinyl α– Amino Acids", *Tetrahedron* 1969, 25, 5971–5981.

Nollet et al., "Unconventional Nucleotide Analogues–II, Synthesis of the Adenyl Analogue of Willardiine", *Tetrahedron* 1969, 25, 5983–5987.

Nollet et al., "Michael Addition of 4–O–Ethyluracil. A Method for Specific $N_1$–Alkylation of Hydroxpyrimidines", *Tetrahedron Letters* 1969, 53, 4605–4606.

Pitha et al., "Inhibition of Murine Leukemia Virus Replication by Poly (vinyluracil) and Poly (vinyladenine)", *Proc. Natl Acad. Sci. USA* 1973, 70, 1204–1208.

Pitha, J., "Physiological Activities of Synthethic Analogs of Polynucleotides", *Adv. Polym. Sci.* 1983, 50, 1–16.

Simon et al., "Peptoids: A modular approach to drug discovery", *Proc. Natl. Acad. Sci. USA* 1992, 89, 9367–9371.

Takemoto et al, "Synthetic Nucleic Acid Analogs. Preparation and Interactions", *Adv. Polym. Sci.* 1981, 1–51.

Uhlmann et al., "Antisense Oligonucleotides: A New Therapeutic Principle", *Chemical Reviews* 1990, 90, 544–583.

Weller et al., "Molecular Modeling of Acyclic Polyamide Oligonucleotide Analogues", *J. Org. Chem.* 1991, 6000–6006.

Brady et al., "Large–Scale Synthesis of a Cyclic Hexapeptide Analogue of Somatostatin," *J. Org. Chem.* 1987, 52, 764–769.

Meier et al., "Peptide Nucleic Acids (PNAs) –Unusual Properties of Nonionic Oligonucleotide Analogues", *Angew. Chem. Int. Ed. Engl.* 1992, 31, 1008–1010.

Gewirtz, "Therapeutic Application of Antisense DNA in the Treatment of Human Leukemia", published in Antisense Strategies vol. 660 178–187 (Oct. 28, 1992) Annals of the New York Academy of Sciences (Baserga & Denhardt Eds.).

Hyrup et al., "Modification of the Binding Affinity of Peptide Nucleic Acids (PNA). PNA with Extended Backbones Consisting of 2–Aminoethyl–β–alanine or 3–Aminopropyglycine Units" *J. Chem. Soc. Chem. Commun.* 1993, 518–519.

Egholm et al., "Peptide Nucleic Acids (PNA): A Novel Approach to Sequence–Selective Recognition of Double–Stranded DNA" Innovation and Perspectives in Solid Phase Synthesisi Collected Papers (Epton, Ed. by Intercept ltd, Andover, England) 1992, 325–328.

Tam, "Design and Synthesis of Multidetachable Resin Supports for Solid–Phase Peptide Synthesis" *J. Am. Chem. Soc.* 1980, 102, 6117–6127.

Almarsson, et al., "Molecular mechanics calculations of the structures of polyamide nucleic acid DNA duplexes and triple hilical hybrids", *Proc., Natl., Acad. Sci., USA*, 1993, 90, 7518–7522.

Almarsson and Bruice, "Peptide nucleic acid (PNA) conformation and polymorphism in PNA–DNA and PNA–RNA hybrids", *Proc. Natl. Acad. Sci., USA*, 1993, 90, 9542–9546.

Brown, et al., "NMR Solution Structure of a Peptide Nucleic Acid Complexed with RNA", *Science*, 1994, 265, 777–780.

Chen, et al., "Molecular Dynamics and NMR Studies of Single–Stranded PNAs", *Tetrahedron Letters*, 1994, 35, 5105–5108.

Demidov, et al., "Stability of peptide nucleic acids in human serum and cellular extracts", *Biochem. Pharm.*, 1994, 48, 1310–1313.

Dueholm, et al., "An Efficient Synthesis of BOC–Aminoacetaldehyde and its Application to the Synthesis of N– (2–BOC–Aminoethyl) Glycine Esters", *Org. Prep.& Proc. Int.*, 1993, 25(4), 457–461.

Dueholm, et al., "Peptide Nucleic Acid (PNA) with a Chiral Backbone Based on Alanine", *Bioorg. & Med. Chem. Letts.*, 1994, 4, 1077–1080.

Dueholm, et al., "Synthesis of Peptide Nucleic Acid Monomers Containing the Four Natural Nucleobases: Thymine, Cytosine, Adenine, and Guanine and Their Oligomerization", *J. Org. Chem.*, 1994, 59, 5767–5773.

Flam F., Can DNA Mimics Improve On the Real Thing? *Science*, 1993, 262, 1647–1649.

Frank–Kamenetskii, Maxim, "A change of backbone", *Nature*, 1991, 354, 505.

Griffith, et al., "Single and Bis Peptide Nucleic Acids as Triplexing Agents: Binding and Stoichiometry", *J. Am. Chem. Soc.*, 1995, 117, 831–832.

Hyrup, et al., "Structure–Activity Studies of the Binding of Modified Peptide Nucleic Acids (PNAs) to DNA[1]" *J. Am. Chem. Soc.*, 1994, 116, 7964–7970.

Kosynkina, et al., "A Convenient Synthesis of Chiral Peptide Nucleic Acid (PNA) Monomers", *Tetrahedron Letters*, 1994, 35, 5173–5176.

Lagriffoul, et al., "The Synthesis, Co–Oligomerization and Hybridization of a Thymine–Thymine Heterodimer Containing PNA", *Bioorg. & Med. Chem. Letters.*, 1994, 4, 1081–1082.

Leijon, et al., "Structural Characterization of PNA–DNA Duplexes by NMR. Evidence for DNA in a B–like Conformation", *Biochemistry*, 1994, 33, 9820–9825.

Mollegaard, et al., "Peptide nucleic acid–DNA strand displacement loops as artificial transcription promoters", *Proc. Natl. Acad. Sci.*, 1994, 91, 3892–3895.

Nielsen, et al., "Peptide nucleic acids (PNAs): Potential antisense and anti–gene agents", *Anti–Cancer Drug Design*, 1993, 8, 53–63.

Frank–Kamenetskii, Maxim, "A change of backbone", *Nature* 1991, 354, 505.*

Griffith, et al., "Single and Bis Peptide Nucleic Acids as Triplexing Agents: Binding and Stoichiometry", *J. Am. Chem. Soc.*, 1995, 117, 831–832.*

Hyrup, et al., "Structure–Activity Studies of the Binding of Modified Peptide Nucleic Acids (PNAs) to DNA[1]", *J. Am. Chem. Soc.*, 1994, 116, 7964–7970.*

Kosynkina, et al., "A Convenient Synthesis of Chiral Peptide Nucleic Acid (PNA) Monomers", *Tetrahedron Letters*, 1994, 35, 5173–5176.*

Lagriffoul, et al., "The Synthesis, Co–Oligomerization and Hybridization of a Thymine–Thymine Heterodimer Containing PNA", *Bioorg. & Med. Chem. Letts.*, 1994, 4, 1081–1082.*

Leijon, et al., "Structural Characterization of PNA–DNA Duplexes by NMR. Evidence for DNA in a B–like Conformation", *Biochemistry*, 1994, 33, 9820–9825.*

Mollegaard, et al., "Peptide nucleic acid–DNA strand displacement loops as artificial transcription promoters", *Proc. Natl. Acad. Sci.*, 1994, 91, 3892–2895.*

Nielsen, et al., "Peptide nucleic acids (PNAs): Potential antisense and anti–gene agents", *Anti–Cancer Drug Design*, 1993, 8, 53–63.*

Nielson, "Peptide Nucleic Acid (PNA): A Model Structure for the Primordial Genetic Material?", *Orig. Life Evol. Biosph.* 1993, 23, 323–327.*

Nielsen, et al., "Peptide Nucleic Acids (PNA): Oligonucleotide Analogs with a Polyamide Backbone", *Antisense Research and Applications*, 363–373, S.T. Crooke and B. Lebleu, eds., CRC Press, Boca Raton, FL 1993.

Nielsen, et al., "Peptide Nucleic Acid (PNA). A DNA Mimic with a Peptide Backbone", *Bioconjugate Chem.*, 1994, 5, 3–7.

Nielsen, et al., "Sequence–specific transcription arrest by peptide nucleic acid bound to the DNA template strand", *Gene*, 1994, 149, 139–145.

Orum, et al., "Single base pair mutation analysis by PNA directed PCR clamping", *Nucleic Acids Research*, 1993, 21, 5332–5336.

Peffer, et al., "Strand–invasion of duplex DNA by peptide nucleic acid oligomers", *Proc. Natl. Acad. Sci. USA*, 1993, 90, 10648–10652.

Rose, Donald J., "Characterization of Antisense Binding Properties of Peptide Nucleic Acids by Capillary Gel Electrophoresis", *Anal. Chem.*, 1993, 65, 3545–3549.

Wittung, et al., "DNA–like double helix formed by peptide nucleic acid", *Nature*, 1994, 368, 561–563.

Nielsen, , et al., "Peptide Nucleic Acids (PNA): Potential antiviral agents", *Int'l. Antiviral News*, (1993), 1, 37–39.

Bergstrom, D., "Organometallic Intermediates in the Synthesis of Nucleoside Analogs", *Nucleosides & Nucleotides* 1982, 1(1), 1–34.

Switzer, C. et al., "Enzymatic Recognition of the Base Pair between Isocytidine and Isoguanosine", *Biochemistry* 1993, 32, 10489–10496.

* cited by examiner a) HCOOMe/MeONa b) HN=C(NH$_2$)$_2$HCl/MeONa c) SOCl$_2$/MeOH d) CF$_3$SO$_3^-$ Cbz-N⟨imidazole⟩N$^+$— e) LiOH/H$_2$O f) Boc-HN⌒N(H)⌒COOEt / O⟨morpholine⟩N-Me/HBTU g) NaOH/H$_2$O/MeOH a) S=C(NH$_2$)$_2$/MeONa b) ClCH$_2$COOH/HCl/H$_2$O c) Boc-HN⁀N(H)⁀COOEt / O(morpholine)N-Me/TDBTU d) NaOH/H$_2$O a) $CF_3SO_3^-$ Cbz—N⟨ ⟩N+— b) $BrCH_2COOH/DCC/DhbtOH$ c) $K_2CO_3$ d) $LiOH/H_2O$ a) Methylbromoacetate b) NaOH/HCl c) Dhbt-OH/N'-Boc-aminoethylglycine ethyl ester-DCC d) NaOH/HCl

SEQUENCE LISTING

<160> NUMBER OF SEQ ID NOS: 65

<210> SEQ ID NO 1
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 1 gcat                                                                      4

<210> SEQ ID NO 2
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 2 gcat                                                                      4

<210> SEQ ID NO 3
<211> LENGTH: 4
<212> TYPE: DNA

-continued

```
<213> ORGANISM: Artificial Sequence
<220> FEATURE:
<223> OTHER INFORMATION: Description of Artificial Sequence: Novel
      Sequence

<400> SEQUENCE: 3 gcat                                                                      4

<210> SEQ ID NO 4
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4 gcat                                                                      4

<210> SEQ ID NO 5
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5 gcat                                                                      4

<210> SEQ ID NO 6
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 6 gcat                                                                      4

<210> SEQ ID NO 7
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7 gcat                                                                      4

<210> SEQ ID NO 8
<211> LENGTH: 4
<212> TYPE: DNA
<213> ORGANISM: Artificial Sequence
<220> FEATURE:
<223> OTHER INFORMATION: Description of Artificial Sequence: Novel
      Seqeunce

<400> SEQUENCE: 8 gcat                                                                      4

<210> SEQ ID NO 9
<211> LENGTH: 4
<212> TYPE: DNA
<213> ORGANISM: Artificial Sequence
```

```
<220> FEATURE:
<223> OTHER INFORMATION: Description of Artificial Sequence: Novel
      Sequence

<400> SEQUENCE: 9 gcat                                                                    4

<210> SEQ ID NO 10
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10 gcat                                                                    4

<210> SEQ ID NO 11
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11 gcat                                                                    4

<210> SEQ ID NO 12
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12 gcat                                                                    4

<210> SEQ ID NO 13
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 13 gcat                                                                    4

<210> SEQ ID NO 14
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 14 gcat                                                                    4

<210> SEQ ID NO 15
<211> LENGTH: 4
<212> TYPE: DNA
<213> ORGANISM: Artificial Sequence
<220> FEATURE:
```

-continued

```
<223> OTHER INFORMATION: Description of Artificial Sequence: Novel
      Sequence

<400> SEQUENCE: 15 gcat                                                              4

<210> SEQ ID NO 16
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 16 gcat                                                              4

<210> SEQ ID NO 17
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 17 gcat                                                              4

<210> SEQ ID NO 18
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 18 gcat                                                              4

<210> SEQ ID NO 19
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19 gcat                                                              4

<210> SEQ ID NO 20
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20 gcat                                                              4

<210> SEQ ID NO 21
<211> LENGTH: 4
<212> TYPE: DNA
<213> ORGANISM: Artificial Sequence
<220> FEATURE:
<223> OTHER INFORMATION: Description of Artificial Sequence: Novel
```

Sequence

<400> SEQUENCE: 21 gcat                                                                4

<210> SEQ ID NO 22
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22 gcat                                                                4

<210> SEQ ID NO 23
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 23 gcat                                                                4

<210> SEQ ID NO 24
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 24 gcat                                                                4

<210> SEQ ID NO 25
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 25 gcat                                                                4

<210> SEQ ID NO 26
<211> LENGTH: 4
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 26 gcat                                                                4

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

```
<221> NAME/KEY: misc_feature
<222> LOCATION: (10)..(11)
<223> OTHER INFORMATION: Lysine, Amino Hexanoic Acid, Lysine, Amino
      Hexanoic Acid, Lysine Linkage

<400> SEQUENCE: 27
ttctctctct tctctctctt                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Lysine, Amino Cis-hexenoic Acid, Lysine, Amino
      Cis-hexenoic Acid, Lysine Linkage

<400> SEQUENCE: 28
ttctctctct tctctctctt                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Lysine, Amino Hexynoic Acid, Lysine, Amino
      Hexynoic Acid, Lysine Linkage

<400> SEQUENCE: 29
ttctctctct tctctctctt                                              20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Lysine, Meta-Amino Benzoic Acid, Lysine,
      Meta-Amino Benzoic Acid, Lysine Linkage

<400> SEQUENCE: 30
ttctctctct tctctctctt                                              20

<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)..(7)
<223> OTHER INFORMATION: Lysine, Amino Hexanoic Acid, Lysine, Amino
      Hexanoic Acid, Lysine Linkage

<400> SEQUENCE: 31 tcttttttt ctttt                                                    15

<210> SEQ ID NO 32
```

```
<211> LENGTH: 18
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (9)..(10)
<223> OTHER INFORMATION: Lysine, Amino Hexanoic Acid, Lysine, Amino
      Hexanoic Acid, Lysine Linkage

<400> SEQUENCE: 32
ttttgttttt tttctttt                                               18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (9)..(10)
<223> OTHER INFORMATION: Lysine, Amino Hexanoic Acid, Lysine, Amino
      Hexanoic Acid, Lysine Linkage

<400> SEQUENCE: 33
ttttcttttt tttctttt                                               18

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)
<223> OTHER INFORMATION: N is Pseudoisocytosine
<221> NAME/KEY: misc_feature
<222> LOCATION: (5)
<223> OTHER INFORMATION: N is Pseudoisocytosine
<221> NAME/KEY: misc_feature
<222> LOCATION: (7)
<223> OTHER INFORMATION: N is Pseudoisocytosine
<221> NAME/KEY: misc_feature
<222> LOCATION: (9)
<223> OTHER INFORMATION: N is Pseudoisocytosine
<221> NAME/KEY: misc_feature
<222> LOCATION: (10)..(11)
<223> OTHER INFORMATION: Lysine, Amino Hexanoic Acid, Lysine, Amino
      Hexanoic Acid, Lysine Linkage

<400> SEQUENCE: 34
ttntntntnt tctctctctt                                             20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: N is Pseudouracil
<221> NAME/KEY: misc_feature
<222> LOCATION: (6)
<223> OTHER INFORMATION: N is Pseudouracil
<221> NAME/KEY: misc_feature
<222> LOCATION: (7)
<223> OTHER INFORMATION: N is Pseudoisocytosine
<221> NAME/KEY: misc_feature
```

```
<222> LOCATION: (10)
<223> OTHER INFORMATION: N is Pseudouracil
<221> NAME/KEY: misc_feature
<222> LOCATION: (10)..(11)
<223> OTHER INFORMATION: Lysine, Amino Hexanoic Acid, Lysine, Amino
      Hexanoic Acid, Lysine Linkage

<400> SEQUENCE: 35
gnagannacn guagaucacu                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:  Novel
      Sequence
<221> NAME/KEY: misc_feature
<222> LOCATION: (3)
<223> OTHER INFORMATION: N is Isocytosine
<221> NAME/KEY: misc_feature
<222> LOCATION: (5)
<223> OTHER INFORMATION: N is Isocytosine
<221> NAME/KEY: misc_feature
<222> LOCATION: (7)
<223> OTHER INFORMATION: N is Isocytosine
<221> NAME/KEY: misc_feature
<222> LOCATION: (9)
<223> OTHER INFORMATION: N is Isocytosine
<221> NAME/KEY: misc_feature
<222> LOCATION: (10)..(11)
<223> OTHER INFORMATION: Lysine, Amino Hexanoic Acid, Lysine, Amino
      Hexanoic Acid, Lysine Linkage

<400> SEQUENCE: 36
ttntntntnt tctctctctt                                              20

<210> SEQ ID NO 37
<211> LENGTH: 20
<212> TYPE: RNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: 5-Bromouracil
<221> NAME/KEY: misc_feature
<222> LOCATION: (6)
<223> OTHER INFORMATION: 5-Bromouracil
<221> NAME/KEY: misc_feature
<222> LOCATION: (7)
<223> OTHER INFORMATION: N is Pseudoisocytosine
<221> NAME/KEY: misc_feature
<222> LOCATION: (10)
<223> OTHER INFORMATION: 5-Bromouracil
<221> NAME/KEY: misc_feature
<222> LOCATION: (10)..(11)
<223> OTHER INFORMATION: Lysine, Amino Hexanoic Acid, Lysine, Amino
      Hexanoic Acid, Lysine Linkage

<400> SEQUENCE: 37
gnagannacn guagaucacu                                              20

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (7)..(8)
```

```
<223> OTHER INFORMATION: Ethylene Glycol, Ethylene Glycol, Ethylene
      Glycol Linkage

<400> SEQUENCE: 38
tctctttttt ctct                                                    14

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Ethylene Glycol, Ethylene Glycol, Ethylene
      Glycol Linkage

<400> SEQUENCE: 39
ttttcctctc ctctccttttt                                             20

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (8)..(9)
<223> OTHER INFORMATION: Ethylene Glycol, Ethylene Glycol, Ethylene
      Glycol Linkage

<400> SEQUENCE: 40
gtagatcatg atctac                                                  16

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: N is Pseudoisocytosine
<221> NAME/KEY: misc_feature
<222> LOCATION: (4)
<223> OTHER INFORMATION: N is Pseudoisocytosine
<221> NAME/KEY: misc_feature
<222> LOCATION: (7)..(8)
<223> OTHER INFORMATION: Ethylene Glycol, Ethylene Glycol, Ethylene
      Glycol Linkage

<400> SEQUENCE: 41 tntnttttt ctct                                                     14

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)
<223> OTHER INFORMATION: N is Pseudoisocytosine
<221> NAME/KEY: misc_feature
<222> LOCATION: (5)..(6)
<223> OTHER INFORMATION: N is Pseudoisocytosine
<221> NAME/KEY: misc_feature
```

```
<222> LOCATION: (8)..(9)
<223> OTHER INFORMATION: Ethylene Glycol, Ethylene Glycol, Ethylene
      Glycol Linkage

<400> SEQUENCE: 42 ttntnnttttt cctctt                                                    16

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)..(5)
<223> OTHER INFORMATION: N is Pseudoisocytosine
<221> NAME/KEY: misc_feature
<222> LOCATION: (8)..(9)
<223> OTHER INFORMATION: Ethylene Glycol, Ethylene Glycol, Ethylene
      Glycol Linkage
<221> NAME/KEY: misc_feature
<222> LOCATION: (12)..(14)
<223> OTHER INFORMATION: N is Pseudoisocytosine

<400> SEQUENCE: 43
ttnnnttttt tnnntt                                                     16

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)
<223> OTHER INFORMATION: N is Pseudoisocytosine
<221> NAME/KEY: misc_feature
<222> LOCATION: (5)..(6)
<223> OTHER INFORMATION: N is Pseudoisocytosine
<221> NAME/KEY: misc_feature
<222> LOCATION: (9)..(10)
<223> OTHER INFORMATION: Ethylene Glycol, Ethylene Glycol, Ethylene
      Glycol Linkage

<400> SEQUENCE: 44 ttntnnttttt ttcctctt                                                  18

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (4)..(5)
<223> OTHER INFORMATION: N is Pseudoisocytosine
<221> NAME/KEY: misc_feature
<222> LOCATION: (7)..(8)
<223> OTHER INFORMATION: Ethylene Glycol, Ethylene Glycol, Ethylene
      Glycol Linkage

<400> SEQUENCE: 45 tttnntttc cttt                                                        14

<210> SEQ ID NO 46
<211> LENGTH: 20
<212> TYPE: DNA
<213> ORGANISM: Artificial Sequence
```

```
<220> FEATURE:
<223> OTHER INFORMATION: Description of Artificial Sequence: Novel
      Sequence
<221> NAME/KEY: misc_feature
<222> LOCATION: (5)..(6)
<223> OTHER INFORMATION: N is Pseudoisocytosine
<221> NAME/KEY: misc_feature
<222> LOCATION: (8)
<223> OTHER INFORMATION: N is Pseudoisocytosine
<221> NAME/KEY: misc_feature
<222> LOCATION: (10)
<223> OTHER INFORMATION: N is Pseudoisocytosine
<221> NAME/KEY: misc_feature
<222> LOCATION: (10)..(11)
<223> OTHER INFORMATION: Ethylene Glycol, Ethylene Glycol, Ethylene
      Glycol Linkage

<400> SEQUENCE: 46
ttttnntntn ctctcctttt                                             20

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(6)
<223> OTHER INFORMATION: N is Pseudoisocytosine
<221> NAME/KEY: misc_feature
<222> LOCATION: (8)
<223> OTHER INFORMATION: N is Pseudoisocytosine
<221> NAME/KEY: misc_feature
<222> LOCATION: (10)..(12)
<223> OTHER INFORMATION: N is Pseudoisocytosine
<221> NAME/KEY: misc_feature
<222> LOCATION: (14)
<223> OTHER INFORMATION: N is Pseudoiscytosine
<221> NAME/KEY: misc_feature
<222> LOCATION: (15)..(16)
<223> OTHER INFORMATION: Ethylene Glycol, Ethylene Glycol, Ethylene
      Glycol Linkage

<400> SEQUENCE: 47
ttttnntntn nntnttctcc ctctcctttt                                  30

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)
<223> OTHER INFORMATION: N is Pseudoisocytosine
<221> NAME/KEY: misc_feature
<222> LOCATION: (6)
<223> OTHER INFORMATION: N is Pseudoisocytosine
<221> NAME/KEY: misc_feature
<222> LOCATION: (10)..(11)
<223> OTHER INFORMATION: Ethylene Glycol, Ethylene Glycol, Ethylene
      Glycol Linkage

<400> SEQUENCE: 48
ttnttntttt ttttcttctt                                             20

<210> SEQ ID NO 49
<211> LENGTH: 20
<212> TYPE: DNA
<213> ORGANISM: Artificial Sequence
<220> FEATURE:
```

```
<223> OTHER INFORMATION: Description of Artificial Sequence: Novel
      Sequence
<221> NAME/KEY: misc_feature
<222> LOCATION: (10)..(11)
<223> OTHER INFORMATION: Ethylene Glycol, Ethylene Glycol, Ethylene
      Glycol Linkage
<221> NAME/KEY: misc_feature
<222> LOCATION: (13)
<223> OTHER INFORMATION: N is Pseudoisocytosine
<221> NAME/KEY: misc_feature
<222> LOCATION: (20)
<223> OTHER INFORMATION: N is Pseudoiscytosine

<400> SEQUENCE: 49
cttttttctt ttnttttttn                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Ethylene Glycol, Ethylene Glycol, Ethylene
      Glycol Linkage
<221> NAME/KEY: misc_feature
<222> LOCATION: (11)
<223> OTHER INFORMATION: N is Pseudoisocytosine
<221> NAME/KEY: misc_feature
<222> LOCATION: (15)
<223> OTHER INFORMATION: N is Pseudoisocytosine
<221> NAME/KEY: misc_feature
<222> LOCATION: (18)
<223> OTHER INFORMATION: N is Pseudoisocytosine
<221> NAME/KEY: misc_feature
<222> LOCATION: (20)
<223> OTHER INFORMATION: N is Pseudoisocytosine

<400> SEQUENCE: 50
ctcttctttc ntttnttntn                                              20

<210> SEQ ID NO 51
<211> LENGTH: 7
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (4)
<223> OTHER INFORMATION: N is Pseudoisocytosine
<221> NAME/KEY: misc_feature
<222> LOCATION: (6)
<223> OTHER INFORMATION: N is Pseudoisocytosine

<400> SEQUENCE: 51 tttntnt                                                             7

<210> SEQ ID NO 52
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (7)..(8)
<223> OTHER INFORMATION: Ethylene Glycol, Ethylene Glycol, Ethylene
      Glycol Linkage
<221> NAME/KEY: misc_feature
<222> LOCATION: (11)
```

```
<223> OTHER INFORMATION: N is Peseudoisocytosine
<221> NAME/KEY: misc_feature
<222> LOCATION: (13)
<223> OTHER INFORMATION: N is Pseudoisocytosine

<400> SEQUENCE: 52 tctcttttttt ntnt                                                   14

<210> SEQ ID NO 53
<211> LENGTH: 7
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 53 tctcttt                                                             7

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: N is Pseudouridine
<221> NAME/KEY: misc_feature
<222> LOCATION: (6)
<223> OTHER INFORMATION: N is Pseudouridine
<221> NAME/KEY: misc_feature
<222> LOCATION: (7)
<223> OTHER INFORMATION: N is Pseudoisocytosine
<221> NAME/KEY: misc_feature
<222> LOCATION: (9)
<223> OTHER INFORMATION: N is Pseudoisocytosine
<221> NAME/KEY: misc_feature
<222> LOCATION: (10)
<223> OTHER INFORMATION: N is Pseudouridine

<400> SEQUENCE: 54 gnagannann                                                         10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: N is Isocytosine
<221> NAME/KEY: misc_feature
<222> LOCATION: (4)
<223> OTHER INFORMATION: N is Isocytosine
<221> NAME/KEY: misc_feature
<222> LOCATION: (7)
<223> OTHER INFORMATION: N is Pseudoisocytosine
<221> NAME/KEY: misc_feature
<222> LOCATION: (10)
<223> OTHER INFORMATION: N is Pseudoisocytosine

<400> SEQUENCE: 55 tncntcnctn                                                         10

<210> SEQ ID NO 56
<211> LENGTH: 13
<212> TYPE: DNA
```

```
<213> ORGANISM: Artificial Sequence
<220> FEATURE:
<223> OTHER INFORMATION: Description of Artificial Sequence: Novel
      Sequence

<400> SEQUENCE: 56
cgcaaagaga cgc                                                              13

<210> SEQ ID NO 57
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 57
cgcaaacaga cgc                                                              13

<210> SEQ ID NO 58
<211> LENGTH: 14
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 58
cgcaaaagag acgc                                                             14

<210> SEQ ID NO 59
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 59
cgcaaataga cgc                                                              13

<210> SEQ ID NO 60
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 60
cgcaaacaca cgc                                                              13

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 61
ttctctctct                                                                  10

<210> SEQ ID NO 62
<211> LENGTH: 10
<212> TYPE: DNA
<213> ORGANISM: Artificial Sequence
```

-continued

```
<220> FEATURE:
<223> OTHER INFORMATION: Description of Artificial Sequence: Novel
      Sequence

<400> SEQUENCE: 62
tctctctctt                                                                        10

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Ethylene Glycol, Ethylene Glycol, Ethylene
      Glycol Linkage

<400> SEQUENCE: 63
ttctctctct tctctctctt                                                             20

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 64
attgtagaga gagaat                                                                 16

<210> SEQ ID NO 65
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 65
cgcagagaaa cgc                                                                    13
```

PEPTIDE NUCLEIC ACIDS

CROSS REFERENCE TO RELATED APPLICATIONS

This application is a continuation-in-part of U.S. application Ser. No. 08/108,591, filed Aug. 27, 1993 that, in turn, is a national phase application of PCT application EP/01219, filed May 22, 1992, claiming priority to Danish Patent Applications: No. 986/91, filed May 24, 1991, No. 987/91, filed May 24, 1991, and No. 510/92, filed Apr. 15, 1992. In addition, this application is a continuation-in-part to U.S. application Ser. No. 08/088,658, filed Jul. 2, 1993; now U.S. Pat. No. 5,641,625; and U.S. application Ser. No. 08/088,661, filed Jul. 2, 1993, now U.S. Pat. No. 6,228,982. The entire disclosure of each of these applications are incorporated herein by reference.

FIELD OF THE INVENTION

This invention is directed to compounds that are not polynucleotides yet which bind to complementary DNA and RNA strands more strongly than corresponding polynucleotides. In particular, the invention concerns novel peptide nucleic acid compounds and novel linked peptide nucleic acid compounds wherein naturally-occurring nucleobases or other nucleobase-binding moieties are covalently bound to a polyamide backbone which is covalently linked via a linking moiety to a second similarly substituted polyamide backbone.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecule. Other modifications have been made to the ribose phosphate backbone to increase the nuclease stability of the resulting analog. These modifications include use of methyl phosphonates, phosphorothioates, phosphorodithioate linkages, and 2'—O-methyl ribose sugar units. Further modifications, include modification made to modulate uptake and cellular distribution. Phosphorothioate oligonucleotides are presently being used as antisense agents in human clinical trials for various disease states including use as antiviral agents. With the success of these oligonucleotides for both diagnostic and therapeutic uses, there exists an ongoing demand for improved oligonucleotide analogs.

Oligonucleotides can interact with native DNA and RNA in several ways. One of these is duplex formation between an oligonucleotide and a single stranded nucleic acid. The other is triplex formation between an oligonucleotide and double stranded DNA to form a triplex structure; however, to form a triplex structure with a double stranded DNA, the cytosine bases of the oligonucleotide must be protonated. This thus renders such triplexing pH dependent. P.O.P. Ts'o and associates have used pseudo isocytosine as a permanently protonated analogue of cytosine in DNA triplexing (see Ono, et al., *J. Am. Chem. Soc.*, 1991, 113, 4032–4033; Ono, et. al., *J. Org. Chem.*, 1992, 57, 3225–3230). Trapane and Ts'o have also suggested the us of pseudo isocytosine for triplex formation with singe-stranded nucleic acid targets. (see, Trapane, et. al., *J. Biomol. Strul. Struct.*, 1991, 8, 229; Trapane, et. al., *Biophys. J.*, 1992, 61, 2437; and Trapane, et. al., Abstracts Conference on Nucleic Acids Medical Applications, Cancun, Mexico, January 1993).

8-Oxoadenine was also suggested in patent application WO 93/05180 for protonated cytosine in triplex formation.

Peptide nucleic acids are compounds that in certain respects are similar to oligonucleotide analogs however in other very important respects their structure is very different. In peptide nucleic acids, the deoxyribose phosphate backbone of oligonucleotides has been replaced with a backbone more akin to a peptide than a sugar phosphodiester. Each subunit has a naturally occurring or non naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA(RNA) triplexes of high thermal stability (see, e.g., Egholm, et al., *Science*, 1991, 254, 1497; Egholm, et al., *J. Am. Chem. Soc.*, 1992, 114, 1895; Egholm, et al., *J. Am. Chem. Soc.*, 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for (PNA)$_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the PNA$_2$/DNA complex area. The other strand of the DNA is locked up in the (PNA)$_2$/DNA triplex structure. The loop area (alternately referenced as a P loop) being single stranded, is susceptible to cleavage by enzymes that can cleave single stranded DNA.

A further advantage of PNA compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike DNA and peptides.

Because of their properties, PNAs are known to be useful in a number of different areas. Since PNAs having stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the P-loop will not be cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

PNAs have further been used to detect point mutations in PCR-based assays (PCR clamping). PCR clamping uses PNA to detect point mutations in a PCR-based assay, e.g. the distinction between a common wild type allele and a mutant allele, in a segment of DNA under investigation. A PNA oligomer complementary to the wild type sequence is synthesized. The PCR reaction mixture contains this PNA and two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, one can determine the presence and exact identity of a mutant.

OBJECTS OF THE INVENTION

It is an object of this invention to provide compounds that bind ssDNA, dsDNA and ssRNA nucleic acids to form complexes with improved thermal stability, specificity, and other properties relative to corresponding DNA.

It is a further object of this invention to provide compounds that bind nucleic acids via strand invasion using two sequences of PNA which may be linked together to form a bis PNA wherein one strand binds anti-parallel relative to the target utilizing Watson/Crick type hydrogen bonds and the second strand binds parallel relative to the target utilizing Hoogsteen type hydrogen bonds.

It is a further object of this invention to provide PNAs and bis PNAs wherein C-pyrimidine heterocyclic bases or iso pyrimidine heterocyclic bases are substituted in place of at least one pyrimidine heterocyclic base.

It is a further object of this invention to provide compounds that bind nucleic acids via strand invasion using two sequences of PNA which may be linked together wherein the cytosines of the parallel strand relative to the target have been replaced with pseudo isocytosines to form a bis PNA wherein one strand binds anti-parallel relative to the target forming Watson/Crick type hydrogen bonds and the second strand binds parallel relative to the target forming Hoogsteen type hydrogen bonds.

It is a further object of this invention to provide bis PNA structures wherein the cytosine nucleobases are replaced with pseudo isocytosines in the Hoogsteen strand.

It is a further object of this invention to provide therapeutic, diagnostic, and prophylactic methods that employ such compounds.

SUMMARY OF THE INVENTION

The present invention is directed to modified peptide nucleic acids especially PNAs that are linked via a linking segment. Such PNAs have been given the short hand name "bis peptide nucleic acids" or "bis PNAs." The present invention is also directed to modified peptide nucleic acids that incorporate certain non-natural nucleobases for Hoogsteen type base paring. These modified peptide nucleic acids are particularly useful for diagnostic uses, including the identification of certain sites in double stranded DNA, restriction enzyme sites, transcription inhibition, clamping to detect point mutations and for use in Hoogsteen strands in triplexing motif.

In accordance with this invention there are provided compounds that include a peptide nucleic acid that has at least one peptide nucleic acid monomeric unit having a pyrimidine heterocyclic base that is a C-pyrimidine heterocyclic base or an iso-pyrimidine heterocyclic base. In certain preferred embodiments of this invention the pyrimidine heterocyclic base is a C-pyrimidine heterocyclic base. In other preferred embodiments of this invention the pyrimidine heterocyclic base is pseudo-isocytosine. In a further embodiment of the invention the C-pyrimidine heterocyclic base is pseudo-uracil, 5-bromouracil, iso-cytosine or other iso-pyrimidine heterocyclic base.

Compounds of the invention, including compounds having C-pyrimidines and iso-pyrimidine heterocyclic bases, include compounds of formula I:

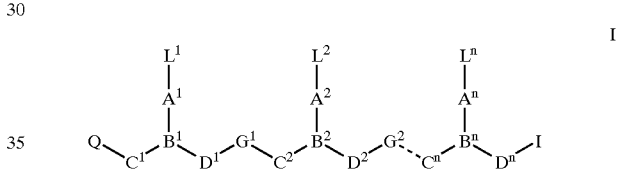

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands;

each of $C^1$–$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are each independently selected from the group consisting of hydrogen, ($C_1$–$C_4$)alkyl, hydroxy- or alkoxy- or alkylthio-substituted ($C_1$–$C_4$)alkyl, hydroxy, alkoxy, alkylthio and amino, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $(CR^6R^7)_z$ where $R^6$ and $R^7$ are as defined above;

each of y and z is zero or an integer from 1 to 10, the sum y+z being greater than 1 but not more than 10;

each of $G^1$–$G^{n-1}$ is —$NR^3CO$—, —$NR^3CS$—, —$NR^3SO$— or —$NR^3SO_2$—, in either orientation, where $R^3$ is as defined above;

each of $A^1$–$A^n$ and $B^1$–$B_n$ are selected such that:

(a) A is a group of formula (IIa), (IIb), (IIc) or (IId), and B is N or $R^3N^+$; or (b) A is a group of formula (IId) and B is CH;

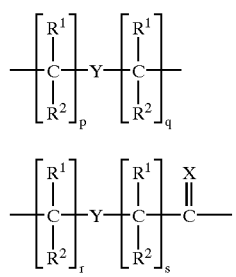

(IIa)

(IIb)

where:

X is O, S, Se, $NR^3$, $CH_2$ or $C(CH_3)_2$;

Y is a single bond, O, S or $NR^4$; each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each $R^3$ and $R^4$ are as defined above;

Q is $-CO_2H$, $-CONR'R''$, $-SO_3H$ or $-SO_2NR'R''$ or an activated derivative of $-CO_2H$ or $-SO_3H$; and I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

Peptide nucleic acids compounds of the invention further include compounds of structure III, IV or V:

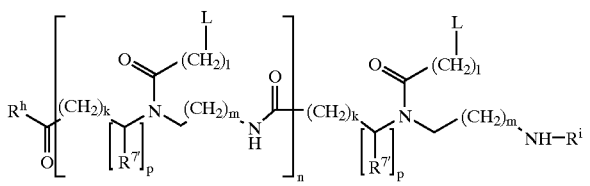

III

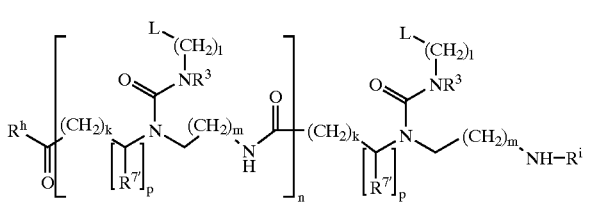

IV

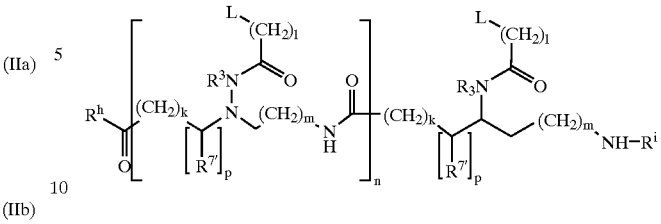

V wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, $NH_2$ or $-NHLysNH_2$; and $R^i$ is H or $COCH_3$.

Further in accordance with this invention there are provided compounds having a first and a second peptide nucleic acid segments that are joined together via at least one linking segment that is not a peptide nucleic acid or an oligonucleotide.

In preferred embodiments of the invention, the linking segment includes a linear structure having a carboxylic acid functional group on one end thereof and a primary amino functional group on the other end thereof. Preferred linking segments includes at least one unit of the structure:

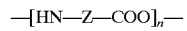

wherein n is 1 to 3; and Z is $C_1-C_{20}$ alkyl, $C_2-C_{20}$ alkenyl, $C_2-C_{20}$ alkynyl, $C_1-C_{20}$ alkanoyl having at least one O or S hetero atom, $C_1-C_{17}$ aryl, or $C_7-C_{34}$ aralkyl.

In a more preferred embodiment, the linking segment includes at least one aminoalkylcarboxylic acid of the formula:

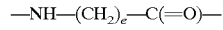

where e is 1 to 15. In certain preferred embodiments e is from 4 to 8. In a more preferred embodiment e is 6.

In other preferred embodiments, the linking segment includes structures of the immediate above formula and at least one further α-amino acid such that they are of formula:

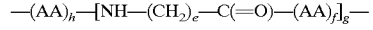

where:

AA is an α-amino acid;

e is 4 to 8;

f and h are 0 or 1; and g is 1 to 4.

In further preferred embodiments, the linking segment includes at least one unit of a glycol amino acid. The glycol amino acid is formed of glycol sub-units linked together in a linear array and having an amino group on one terminus and a carboxyl group on the other terminus. Preferred glycol amino acid linking segments are compounds of the formula:

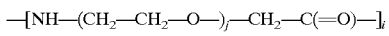

wherein j is 1 to 6; and i is 1 to 6. In one particularly preferred embodiment, j is 2 and i is 3.

In a further embodiment of the invention, both of the ends of two respective peptide nucleic acid segments are joined together via two of the linking segments to form a cyclic structure.

In a further embodiment of the invention, the linking segment connects a terminal amine function on one of first and second peptide nucleic acid segments to a carboxyl function on the other of first and second peptide nucleic acid segments.

In certain preferred embodiments of the invention, the nucleobase sequence of the first peptide nucleic acid segment, in a direction from its amine terminus to its carboxyl terminus, is the same as the nucleobase sequence of the second peptide nucleic acid segment, in a direction from its carboxyl terminus to its amine terminus.

In other embodiments of the invention, at least a portion of the nucleobases of the first and second peptide nucleic acid segments are pyrimidine nucleobases. In a further embodiment of the invention, at least one of the pyrimidine nucleobases of one of the first or the second peptide nucleic acid segments comprises a C-pyrimidine heterocyclic base or an iso-pyrimidine heterocyclic base. In a further embodiment of the invention, a portion of the nucleobases that are pyrimidine nucleobases are located in contiguous homopyrimidine sequences.

Compounds of the invention also include multiple stranded structures having a nucleic acid strand, at least a portion of which forms a target nucleotide sequence, and a further strand, formed from first and second peptide nucleic acid segments that, in turn, are joined together via a linker. The sequence of the nucleobases of the first peptide nucleic acid segment is selected to be complementary to the target nucleotide sequence in the 5' to 3' direction of the target nucleotide sequence and the sequence of the nucleobases of the second peptide nucleic acid segment is selected to be complementary to the target nucleotide sequence in the 3' to 5' direction of the target nucleotide sequence.

In certain embodiments of the invention the nucleic acid strand is a single stranded DNA or RNA and in further embodiments of the invention the nucleic acid strand is a double stranded DNA.

In still a further embodiment of the invention one of the first or second peptide nucleic acid segments binds to the target nucleotide sequence utilizing Watson/Crick type hydrogen bonding and the other of the first or second peptide nucleic acid segments binds to the target nucleotide sequence utilizing Hoogsteen type hydrogen bonding. In a preferred embodiment, the one of the first or second peptide nucleic acid segments that binds to the target nucleotide sequence utilizing said Hoogsteen hydrogen bonding includes C-pyrimidine heterocyclic nucleobases or iso-pyrimidine heterocyclic nucleobases in at least one of the positions that are complementary to nucleobases in the target nucleotide sequence. In certain preferred embodiments the C-pyrimidine heterocyclic nucleobase or iso-pyrimidine heterocyclic nucleobase are selected as pseudo-isocytosine, iso-cytosine, pseudo-uracil or 5-bromouracil.

Compounds of the invention also include a compound having a first segment of joined peptide nucleic acid units having a first sequence of nucleobases and a second segment of joined peptide nucleic acid units having second sequence of nucleobases and a linker group linking the first and the second segments of peptide nucleic acid units. The first segment of peptide nucleic acid units extends from an amino end to a carboxyl end and the second segment of peptide nucleic acid units extends from an amino end to a carboxyl end with the linker group linking the carboxyl end of the first segment of peptide nucleic acid units to the amino end of the second segment of peptide nucleic acid units.

BRIEF DESCRIPTION OF THE DRAWINGS

The numerous objects and advantages of the present invention may be better understood by those skilled in the art by reference to the accompanying figures, in which.

DESCRIPTION OF PREFERRED EMBODIMENTS

Figure 1:
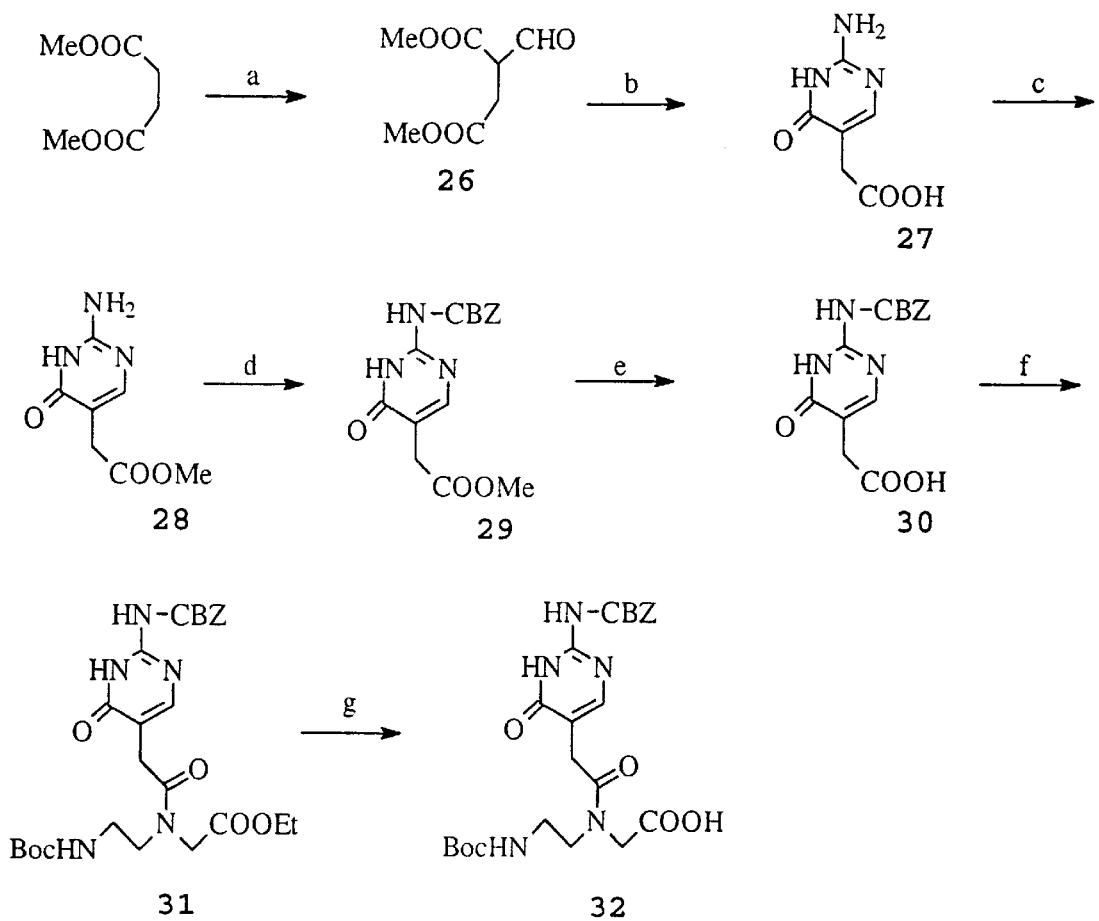
FIG. 1 shows a synthetic scheme according to the invention and discussed in Example 26.

This invention is directed to novel PNA molecules and novel linked PNA molecules. The linked PNA molecules are formed from PNA strands that are joined together with a linking segment. These novel, linked molecules are herein referred to as "bis PNAs." Bis PNAs have been shown to have improved binding, specificity and recognition properties over single stranded PNAS.

In accordance with this invention, it has been found that the most stable triplexes that are formed between two single stranded PNAs or a bis PNA and a DNA or RNA target strand are triplexes wherein the Watson/Crick base pairing strand is in an anti-parallel orientation relative to the target strand and the Hoogsteen base pairing strand is in a arallel orientation relative to the target strand. As so orientated to the target strand, the two PNA strands are therefore anti-parallel to each other.

In the PNA molecules and linked PNA molecules or bis PNAs of the invention as shown in the structures of Formula I above, ligand L is primarily a naturally occurring nucleobase attached at the position found in nature, i.e., position 9 for adenine or guanine, and position 1 for thymine or cytosine. Alternatively, L may be a non-naturally occurring nucleobase (nucleobase analog), another base-binding moiety, an aromatic moiety, ($C_1$–$C_4$)alkanoyl, hydroxy or even hydrogen. In certain preferred embodiments at least one L in the structure is a C-pyrimidine heterocyclic base or an iso-pyrimidine heterocyclic base. In other embodiments L can be a DNA intercalator, a reporter ligand such as, for example, a fluorophor, radio label, spin label, hapten, or a protein-recognizing ligand such as biotin.

For purposes of this invention, the term "pyrimidine" refers to any 1,3-diazine, irrespective of its substituents or position of attachment the other molecular entities. Pyrimidines according to the invention include both naturally-occurring and synthetic nucleobases bases and their analogs. C-pyrimidine nucleobases are nucleobases that if located in a nucleoside would be connected to the sugar portion of the nucleoside via a carbon atom of the pyrimidine ring. As used with peptide nucleic acids of the invention, in a like manner to the above described nucleoside connections, the C-pyrimidine bases are connected to the peptide nucleic acid backbone via a carbon atom of the pyrimidine ring. Iso-pyrimidines according to the invention are 4-keto-2-amino-, 4-thio-2-amino, 2-thio-4-keto, and 2-keto-4-thiodisubstituted pyrimidines. Pseudo-pyrimidines are those that are directly or indirectly bound to a PNA strand through the pyrimidine 5-position.

During synthesis L may be blocked with protecting groups. Suitable protecting groups are acid, base or hydrogen-olytically or photochemically cleavable protecting groups such as, for example, t-butoxycarbonyl (Boc), fluorenylmethyloxycarbonyl (Fmoc), benzyloxycarbonyl (CBZ), benzoyl, 2-chlorobenzyloxycarbonyl, or 2-nitrobenzyl (2Nb).

A can be a wide variety of groups such as $-CR^1R^2CO-$, $-CR^1R^2CS-$, $-CR^1R^2CSe-$, $-CR^1R^2CNHR^3-$, $-CR^1R^2C=CH_2-$ and $-CR^1R^2C=C(CH_3)_2-$, where $R^1$, $R^2$ and $R^3$ are as defined above. Preferably, A is methylenecarbonyl ($-CH_2CO-$). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a $(C_2-C_6)$ alkylene chain, a $(C_2-C_6)$alkylene chain substituted with $R^1R^2$ or can be heterogenous, containing Y. In certain cases, A can just be a single bond.

In certain preferred embodiments of the invention, B is a nitrogen atom, thereby presenting the possibility of an achiral backbone. B can also be $R^3N^+$, where $R^3$ is as defined above. B can also be a CH group.

In certain preferred embodiments of the invention, C is $(-CR^6R^7-)_{\nu}$, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In certain preferred embodiments of the invention D is a $CH_2$ group. D may also be $CR^6R^7$ where $R^6$ and $R^7$ are as defined above.

In certain preferred embodiments of the invention G is selected from $-NR^3CO-$, $-NR^3CS-$, $-NR^3SO-$ or $-NR^3SO_2-$, in either orientation, where $R^3$ is as defined above.

The amino acids and the amino acid analogs that form the backbone of the peptide nucleic acids of the invention may be identical or different. We have found that those based on N-(2-aminoethyl)glycine are especially well suited to the purpose of the invention however a wide range of amino acid analogs may be used in the context of the invention.

The linking segments of the present invention are compounds that are capable of linking two PNA strands together. The preferred orientation is to link the C terminus of a first PNA molecule to the N terminus of a second PNA molecule. Two presently preferred linking segments for linking the PNAs segments are "egl groups" (ethylene glycol) and "Aha groups" (amino hexanoic acid) linked together by amino acid groups. A further presently preferred linking segment includes the above Aha groups interspaced with α-amino acids particularly glycine or lysine.

A wide range of other compounds are also useful for the linking segment and thus are included within the scope of the present invention. Generally the linking segment is a compound having a primary amino group and a carboxy group separated with a space spanning group wherein the space spanning group is made up of one or more functional groups. Some representative space spanning groups are $C_1$ to $C_{20}$ alkyl, $C_2$ to $C_{20}$ alkenyl, $C_2$ to $C_{20}$ alkynyl, $C_1$ to $C_{20}$ alkanoyl having at least one O or S atom, $C_7$ to $C_{34}$ aralkyl, $C_6$-$C_{14}$ aryl and amino acids. Preferred alkanoyl groups can have from 1 to 10 hetero atoms (O or S). Preferred alkanoyl groups include methyl, ethyl and propyl alkanoxy particularly polyethoxy, i.e., ethylene glycol. Amino acids including D, L, and DL isomers of α-amino acids as well as longer chained amino acids may also be linked together to form a linking segment. A particularly preferred amino acid is hexanoic amino acid. Aralkyl groups used as space spanning groups may have the amino or the carboxy group located on the aromatic ring or spaced with one or more $CH_2$ groups wherein the total number of $CH_2$ groups is less than or equal to twenty. The position of substitution in an aralkyl linked PNA may be varied; however, ortho and meta are presently preferred because substitution at these positions, especially ortho, induce the bis PNA to be bent, thus, facilitating location of the two joined peptide nucleic acid strands in spacial locations parallel to one another. Another group of bis PNAs that include induced bends are those that incorporate cis-alkenyl linkers or a proline linker.

In selecting a linking segment, compatibility with PNA chemistry and ability to link a functional group on one end of a PNA to a functional group on one end of a second PNA is a consideration. Also the linking segment can be selected so as to be flexible such that the two linked PNAs are able to interact with ssDNA, ssRNA or dsDNA in much the same way that two independent PNA single strands would. Some preferred linking segments that have been shown to be effective are 23 and 24 atoms in length.

Bis PNAs have shown improved binding affinity, thermal stability, and specificity over single stranded PNAs. Using dsDNA as a target it has been shown that the preferred orientation is with the first PNA strand of the bis PNA parallel to the target, i.e. the target DNA strand of the duplex is referenced in a 5' to 3' direction and the first PNA is complementary in an N to C direction, and the second PNA strand of the bis PNA is antiparallel to the target, i.e. it is complementary to the DNA strand (again referenced in a 5' to 3' direction) in a C to N direction. Thus the linking segment connects the PNA strands in opposite orientation to each other, i.e. from a common reference point, one strand is lined up in a N to C direction and the other is lined up in a C to N direction.

Although we do not wish to be bound by theory it is believed that the antiparallel strand of the bis PNA binds the DNA target thereby displacing the other DNA strand via strand invasion. This binding is of a Watson/Crick nature. The second PNA strand of the bis PNA, the parallel strand, now binds the DNA using Hoogsteen type hydrogen bonding. It has been shown using the component single stranded PNAs and comparing them separately and as a mixture to the bis PNA that the bis PNA has a faster on rate e.g. it binds faster to the target. This faster on rate is attributed to the enforced close proximity of the second strand in the bis PNA.

We have also studied the effect of pH on the Tm of bis PNA bound to dsDNA as compared to the same bis PNA with the cytosines replaced with pseudo isocytosines. It has been observed in previous studies that there is a pronounced dependence on pH for binding of PNA to dsDNA. The decrease in Tm with higher pH shows that Hoogsteen binding in a $(PNA)_2$/DNA complex is pH dependent. Normal Hoogsteen binding requires that the cytosines be protonated. This makes the Hoogsteen strand binding pH dependent. We have found that replacement of one or more of the cytosine nucleobases in a Hoogsteen strand with pseudo isocytosine and other like nucleobases removes this dependence. To demonstrate this effect, in two bis PNAs of the invention, one was synthesized such that the cytosines nucleobases in the parallel strand were replaced with pseudo isocytosines and the other was synthesized such that the cytosines in the antiparallel strand were replaced with pseudo isocytosines. The bis PNA with the pseudo isocytosines in the parallel strand showed almost no dependence on pH indicating that the parallel strand is involved with Hoogsteen binding.

The replacement of cytosine by pseudo isocytosine or other like C-pyrimidine nucleobases is effected in a straight forward manner as per certain of the examples set forth below. This is in direct contrast with replacement of cytosine with pseudo isocytosine or other C-pyrimidines in nucleosides. In nucleosides, an anomeric specific carbon-carbon bond must be formed in synthesizing the C-nucleoside. Since there are no anomeric (sugar) carbon atoms in peptide nucleic acids, such constraints need not be considered.

In a further aspect of the invention, the PNA and bis PNAs are conjugated to low molecular weight effector ligands such as ligands having nuclease activity or alkylating activity or reporter ligands (fluorescent, spin labels, radioactive, protein recognition ligands, for example, biotin or haptens). In a further aspect of the invention, the PNAs and bis PNAs are conjugated to peptides or proteins, where the peptides have signaling activity and the proteins are, for example, enzymes, transcription factors or antibodies. Also, the PNAs can be attached to water-soluble or water-insoluble polymers. In another aspect of the invention, the PNAs and bis PNAs are conjugated to oligonucleotides or carbohydrates. When warranted, a PNA or bis PNA can be synthesized attached to a further moiety (e.g., a peptide chain, reporter, intercalator or other type of ligand-containing group) that in turn is attached to a solid support. As with other PNAs of the invention, such PNA conjugates can be used for gene modulation (e.g., gene targeted drugs), for diagnostics, as biotechnology and research probes, primers, artificial restriction enzymes and the like.

As a further aspect of the invention, PNAs and bis PNAs can be used to target RNA and ssDNA to produce both complementary type gene regulating moieties and hybridization probes for the identification and purification of nucleic acids. Furthermore, the PNAs and bis PNAs can be modified in such a way that they can form triple helices with dsDNA. Reagents that bind sequence-specifically to dsDNA have applications as gene targeted drugs. These are foreseen as extremely useful drugs for treating diseases like cancer, AIDS and other virus infections, and may also prove effective for treatment of some genetic diseases. Furthermore, these reagents may be used for research and in diagnostics for detection and isolation of specific nucleic acids.

The triple helix principle is used in the art for sequence-specific recognition of dsDNA. Triple helix formation utilizes recognition of homopurine-homopyrimidine sequences. A strand displacement complex with triple helix formation is superior to simple triple helix recognition in that strand displacement complexes are very stable at physiological conditions, that is, neutral pH, ambient (20–40° C.) temperature and medium (100–150 mM) ionic strength.

Gene targeted drugs are designed with a nucleobase sequence (containing from about 10 to about 20 units) complementary to the regulatory region (the promoter) of the target gene. Therefore, upon administration of the drug, it binds to the promoter and blocks access thereto by RNA polymerase. Consequently, no mRNA, and thus no gene product (protein), is produced. If the target is within a vital gene for a virus, no viable virus particles will be produced. Alternatively, the target could be downstream from the promoter, causing the RNA polymerase to terminate at this position, thus forming a truncated mRNA/protein which is nonfunctional.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The bis PNAs of the invention are superior to prior reagents in that they have significantly higher affinity for complementary ssDNA. Also, they can be synthesized such that they possess no charge and are water soluble, which should facilitate cellular uptake, and they contain amides of non-biological amino acids, which should make them biostable and resistant to enzymatic degradation by, for example, proteases.

The bis-PNAs and the C-pyrimidine and iso-pyrimidine nucleobase containing PNAs of the invention are particularly useful for diagnostic assays and molecular biological cloning and sub-cloning techniques that can take advantage of the strand displacement effect that occurs upon binding of the bis-PNAs to double stranded DNA. Further they can also be advantageously used for transcription inhibition useful in diagnostic tests and for modification of PCR based assays since they exhibit a even greater base mismatch specificity than does normal PNA.

Synthesis of Monomeric Building Blocks

The monomeric building blocks of the present invention are composed of an amino acid or amino acid analog backbone portion and a nucleobase portion. A more generalized description would be a backbone with a carboxyl functional group, an amino functional group and at least one other functional group e.g. a nucleobase or nucleobase analog. The monomeric building blocks are preferably synthesized by a general procedure that varies depending on the monomer being synthesized. This involves preparation of a backbone portion of the monomeric building block prior to the addition of the nucleobase and any tethered functional moieties, e.g. N(2-aminoethyl) glycine. Illustrative examples are described in Examples 1, 2, 7, 8 and 9. Next, the desired nucleobase or nucleobase analog is covalently bound to the backbone portion to give the monomeric building block. The synthesis of the thymine monomer is illustrated in Examples 3–6, and that of the protected cytosine monomer is illustrated in Example 9–17.

The synthesis of the protected adenine monomer, as is illustrated in Examples 18–22, involved alkylation with ethyl bromoacetate and verification of the position of substitution by X-ray crystallography, as being the wanted 9-position. The $N^6$-amino group then was protected with the benzyloxycarbonyl group by the use of the reagent N-ethyl-benzyloxy-carbonylimidazole tetrafluoroborate. Simple hydrolysis of the product ester gave $N^6$-benzyloxycarbonyl-9-carboxymethyl adenine, which then was used in the standard procedure.

The synthesis of the protected G-monomer is illustrated in examples 23–25. The starting material, 2-amino-6-chloropurine, was alkylated with bromoacetic acid and the chlorine atom was then substituted with a benzyloxy group. The resulting acid was coupled to (boc-aminoethyl) glycine methyl ester with agent PyBrop™, and the resulting ester was hydrolysed. The $O^6$-benzyl group was removed in the final HF-cleavage step in the synthesis of the PNA-oligomer. Cleavage was verified by finding the expected mass of the final PNA-oligomer, upon incorporation into a PNA-oligomer using diisopropyl carbodiimide as the condensation agent.

The synthesis of monomers having C-pyrimidine and iso-pyrimidine heterocyclic bases and their incorporation into PNAs and bis PNAs is illustrated in further of the examples. The replacement of the cytosines with pseudo isocytosines in the parallel strand of a bis PNA that contains an anti-parallel strand has been shown to be stable in a range of pH's whereas the same bis PNA shows a pH dependence when cytosine is present. This effect is illustrated in Example 61.

The synthesis of the pseudo isocytosine monomer is illustrated by Examples 26–32. The synthesis of other monomeric building blocks having either iso-cytosine, 5-bromo uracil, or pseudo uracil are illustrated by Examples 33–44.

Synthesis of PNAs and bis PNAs

Synthesis of PNAs and bis PNAs involve attachment of a first monomeric building block to a solid support. Next, elucidation of the desired PNA is achieved through an iterative process involving deprotecting and coupling. If the desired molecule is a bis PNA, a tether is incorporated in much the same manner as a monomeric building block is incorporated followed by another iterative process as above to elucidate the second PNA chain of desired sequence.

The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85, 2149 and *Science*, 1986, 232, 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix can also be used in solid-phase PNA synthesis in accordance with the present invention (FIG. 8).

Concerning the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Illinois, 1984). Reactions for the introduction of chloromethyl functionality (Merrifield resin; via a chloromethyl methyl ether/SnCl$_4$ reaction), aminomethyl functionality (via an N-hydroxymethylphthalimide reaction; see, Mitchell, et al., *Tetrahedron Lett.*, 1976, 3795), and benzhydrylamino functionality (Pietta, et al., *J. Chem. Soc.*, 1970, 650) are the most widely applied. Regardless of its nature, the purpose of the functionality is normally to form an anchoring linkage between the copolymer solid support and the C-terminus of the first monomeric building block to be coupled to the solid support. As will be recognized, anchoring linkages also can be formed between the solid support and the N-terminus of the monomeric building block. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention. Preferred methods for PNA synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30, 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid, N-Boc-p-acylbenzhydrylamines such as N-Boc-p-glutaroylbenzhydrylamine, N-Boc-4'-lower alkyl-p-acylbenzhydrylamines such as N-Boc-4'-methyl-p-glutaroylbenzhydrylamine, N-Boc-4'-lower alkoxy-p-acylbenzhydrylamines such as N-Boc-4'-methoxy-p-glutaroylbenzhydrylamine, and 4-hydroxymethylphenoxyacetic acid. One type of spacer group particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized PNA or bis PNA chain from the solid support such that the C-terminal of the PNA or bis PNA chain is in amide form, not requiring the introduction of a spacer group. Any such functionality may advantageously be employed in the context of the present invention.

An alternative strategy concerning the introduction of spacer or handle groups is the so-called "preformed handle" strategy (see, Tam, et al., *Synthesis*, 1979, 955–957), which offers complete control over coupling of the first monomeric building block, and excludes the possibility of complications arising from the presence of undesired functional groups not related to the PNA synthesis. In this strategy, spacer or handle groups, of the same type as described above, are reacted with the first monomeric building block desired to be bound to the solid support, the monomeric building block being N-protected and optionally protected at the other side-chains which are not relevant with respect to the growth of the desired PNA chain. Thus, in those cases in which a spacer or handle group is desirable, the first monomeric building block to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (Tam, et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Suitable choices for N-protection are the tert-butyloxycarbonyl (Boc) group (Carpino, *J. Am. Chem. Soc.*, 1957, 79, 4427; McKay, et al., *J. Am. Chem. Soc.*, 1957, 79, 4686; Anderson, et al., *J. Am. Chem. Soc.*, 1957, 79, 6180) normally in combination with benzyl-based groups for the protection of side chains, and the 9-fluorenylmethyloxycarbonyl (Fmoc) group (Carpino, et al., *J. Am. Chem. Soc.*, 1970, 92, 5748 and *J. Org. Chem.*, 1972, 37, 3404), normally in combination with tert-butyl (tBu) for the protection of any side chains, although a number of other possibilities exist which are well known in conventional solid-phase peptide synthesis.

Thus, a wide range of other useful amino protecting groups exist, some of which are Adoc (Hass, et al., *J. Am. Chem. Soc.*, 1966, 88, 1988), Bpoc (Sieber, *Helv. Chem. Acta.*, 1968, 51, 614), Mcb (Brady, et al., *J. Org. Chem.*, 1977, 42, 143), Bic (Kemp, et al., *Tetrahedron*, 1975, 4624), the o-nitrophenylsulfenyl (Nps) (Zervas, et al., *J. Am. Chem. Soc.*, 1963, 85, 3660), and the dithiasuccinoyl (Dts) (Barany, et al., *J. Am. Chem. Soc.*, 1977, 99, 7363). These amino protecting groups, particularly those based on the widely-used urethane functionality, successfully prohibit racemization (mediated by tautomerization of the readily formed oxazolinone (azlactone) intermediates (Goodman, et al., *J. Am. Chem. Soc.*, 1964, 86, 2918) during the coupling of most α-amino acids. In addition to such amino protecting groups, a whole range of nonurethane-type of amino protecting groups are applicable when assembling PNA molecules, especially those built from achiral units. Thus, not only the above-mentioned amino protecting groups (or those derived from any of these groups) are useful within the context of the present invention, but virtually any amino protecting group which largely fulfills the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids or activated monomeric building blocks). Additionally: (4) the protecting group must be close to quantitatively removable, without serious side reactions, and (5) the optical integrity, if any, of the incoming monomeric building block should preferably be highly preserved upon coupling. Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA or bis PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach), Following coupling of the first monomeric building block, the next stage of solid-phase synthesis is the systematic elaboration of the desired PNA chain. This elaboration involves repeated deprotection/coupling cycles. The temporary protecting group, such as a Boc or Fmoc group, on the last-coupled monomeric building block is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected monomeric building block is then coupled to the N-terminal of the last-coupled monomeric building block. This coupling of the C-terminal of a monomeric building block with the N-terminal of the last-coupled monomeric building block can be achieved in several ways. For example, it can be bound by providing the incoming monomeric building block in a form with the carboxyl group activated by any of several methods, including the initial formation of an active ester derivative such as a 2,4,5-trichlorophenyl ester (Pless, et al., *Helv. Chim. Acta*, 1963, 46, 1609), a phthalimido ester (Nefkens, et al., *J. Am. Chem. Soc.*, 1961, 83, 1263), a pentachlorophenyl ester (Kupryszewski, *Rocz. Chem.*, 1961, 35, 595), a pentafluorophenyl ester (Kovacs, et al., *J. Am. Chem. Soc.*, 1963, 85, 183), an o-nitrophenyl ester (Bodanzsky, *Nature*, 1955, 175, 685), an imidazole ester (Li, et al., *J. Am. Chem. Soc.*, 1970, 92, 7608), and a 3-hydroxy-4-oxo-3,4-dihydroquinazoline (Dhbt-OH) ester (Konig, et al., *Chem. Ber.*, 1973, 103, 2024 and 2034), or the initial formation of an anhydride such as a symmetrical anhydride (Wieland, et al., *Angew. Chem., Int. Ed. Engl.*, 1971, 10, 336). Alternatively, the carboxyl group of the incoming monomeric building block can be reacted directly with the N-terminal of the last-coupled monomeric building block with the assistance of a condensation reagent such as, for example, dicyclohexylcarbodiimide (Sheehan, et al., *J. Am. Chem. Soc.*, 1955, 77, 1067) or derivatives thereof. Benzotriazolyl N-oxy-trisdimethylaminophosphonium hexafluorophosphate (BOP), "Castro's reagent" (see, e.g., Rivaille, et al., *Tetrahedron*, 1980, 36, 3413) is recommended when assembling PNA or bis PNA molecules containing secondary amino groups. Finally, activated PNA monomers analogous to the recently-reported amino acid fluorides (Carpino, *J. Am. Chem. Soc.*, 1990, 112, 9651) hold considerable promise to be used in PNA and bis PNA synthesis as well.

The synthesis of a bis PNA from a PNA chain attached to the solid support is similar to the iterative process that is used to synthesize the PNA chain. The last desired monomeric building block is coupled and the gel is washed with a suitable solvent e.g. pyridine. The terminal N protecting group is removed and an activated linking segment is coupled. The linking segment may be a single unit or as is the case with the ethyleneglycol or aminohexanoic acid type linking segments (Examples 47 and 55) the linking segment is added in sub units which, when coupled together will give the desired linking segment. Synthesis of the second segment of PNA is effected as per the first segment.

Following assembly of the desired PNA or bis PNA chain, including protecting groups, the next step will normally be deprotection of the coupled building blocks of the PNA or bis PNA chain and cleavage of the synthesized PNA or bis PNA from the solid support. These processes can take place substantially simultaneously, thereby providing the free PNA or bis PNA molecule in the desired form. Alternatively, in cases in which condensation of two separately synthesized PNA chains is to be carried out, it is possible by choosing a suitable spacer group at the start of the synthesis to cleave the desired PNA or bis PNA chains from their respective solid supports (both peptide chains still incorporating their side-chain protecting groups) and finally removing the side-chain protecting groups after, for example, coupling the two side-chain protected peptide chains to form a longer PNA or bis PNA chain.

In the above-mentioned "Boc-benzyl" protection scheme, the final deprotection of side-chains and release of the PNA or bis PNA molecule from the solid support is most often carried out by the use of strong acids such as anhydrous HF (Sakakibara, et al., *Bull. Chem. Soc. Jpn.*, 1965, 38, 4921), boron tris (trifluoroacetate) (Pless, et al., *Helv. Chim. Acta*, 1973, 46, 1609), and sulfonic acids such as trifluoromethane-sulfonic acid and methanesulfonic acid (Yajima, et al., *J. Chem. Soc., Chem. Comm.*, 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol and, therefore, the sulfide-assisted acidolytic $S_N2$ deprotection method (Tam, et al., *J. Am. Chem. Soc.*, 1983, 105, 6442 and *J. Am. Chem. Soc.*, 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.*, 1973, 95, 4501), and ammonolysis as well as hydrazinolysis (Bodanszky, et al., *Chem. Ind.*, 1964 1423), hydrogenolysis (Jones, *Tetrahedron Lett.*, 1977 2853 and Schlatter, et al., *Tetrahedron Lett.*, 1977, 2861), and photolysis (Rich and Gurwara, *J. Am. Chem. Soc.*, 1975, 97, 1575).

Finally, in contrast with the chemical synthesis of "normal" peptides, stepwise chain building of achiral PNAs and bis PNAs such as those based on aminoethylglycyl backbone units can start either from the N-terminus or the C-terminus, because the coupling reactions are free of racemization. Those skilled in the art will recognize that whereas syntheses commencing at the C-terminus typically employ protected amine groups and free or activated acid groups, syntheses commencing at the N-terminus typically employ protected acid groups and free or activated amine groups.

Based on the recognition that most operations are identical in the synthetic cycles of solid-phase peptide synthesis (as is also the case for solid-phase PNA and bis PNA synthesis), a new matrix, PEPS, was recently introduced (Berg, et al., *J. Am. Chem. Soc.*, 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple PNA and bis PNA molecules, these being conceptually simple to synthesize since only four different reaction compartments are normally required, one for each of the four "pseudo-nucleotide" units. Thus, the PEPS film support has been successfully tested in a number of PNA syntheses carried out in a parallel and substantially simultaneous fashion. The yield and quality of the products obtained from PEPS were comparable to those obtained by using the traditional polystyrene beaded support. Also, experiments with other geometries of the PEPS polymer such as, for example, non-woven felt, knitted net, sticks or microwell plates have not indicated any limitations of the synthetic efficacy.

Two other methods proposed for the simultaneous synthesis of large numbers of peptides also apply to the preparation of multiple, different PNA molecules. The first of these methods (Geysen, et al., *Proc. Natl. Acad. Sci. USA*, 1984, 81, 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, *Proc. Natl. Acad. Sci. USA*, 1985, 82, 5131) utilizes a "tea bag" containing traditionally-used polymer beads. Other relevant proposals for multiple peptide, PNA of bis PNA synthesis in the context of the present invention include the simultaneous use of two different supports with different densities (Tregear, in "*Chemistry and Biology of Peptides*", J. Meienhofer, ed., Ann Arbor Sci. Publ., Ann Arbor, 1972 pp. 175–178), combining of reaction vessels via a manifold (Gorman, *Anal Biochem.*, 1984, 136, 397), multicolumn solid-phase synthesis (e.g. Krchnak, et al., *Int. J. Peptide Protein Res.*, 1989, 33, 209), and Holm and Meldal, in "*Proceedings of the 20th European Peptide Symposium*", G. Jung and E. Bayer, eds., Walter de Gruyter & Co., Berlin, 1989, 208–210), and the use of cellulose paper (Eichler, et al., *Collect. Czech. Chem. Commun.*, 1989, 54, 1746), and U.S. Pat. No. 5,324,483 issued Jun. 28, 1994.

While the conventional cross-linked styrene/divinylbenzene copolymer matrix and the PEPS support are presently preferred in the context of solid-phase PNA and bis PNA synthesis, a non-limiting list of examples of solid supports which may be of relevance are: (1) particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.*, 1975, 97, 6584, *Bioorg. Chem.* 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.*, 1970, 4503); (3) a third general type of useful solid supports can be termed composites in that they contain two major ingredients: a resin and another material that is also substantially inert to the organic synthesis reaction conditions employed. One exemplary composite (see Scott, et al., *J. Chrom. Sci.*, 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, *Israel J. Chem.* 1978, 17, 243) and van Rietschoten in "*Peptides 1974*", Y. Wolman, Ed., Wiley and Sons, New York, 1975, pp. 113–116); and (4) contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345), are suited for PNA and bis PNA synthesis as well.

Whether manually or automatically operated, solid-phase PNA and bis PNA synthesis in the context of the present invention is normally performed batchwise. However, most of the syntheses may equally well be carried out in the continuous-flow mode, where the support is packed into columns (Bayer, et al., *Tetrahedron Lett.*, 1970, 4503 and Scott, et al., *J. Chromatogr. Sci.*, 1971, 9, 577). With respect to continuous-flow solid-phase synthesis, the rigid poly (dimethylacrylamide)-Kieselguhr support (Atherton, et al., *J. Chem. Soc. Chem. Commun.*, 1981, 1151) appears to be particularly successful, but another valuable configuration concerns the one worked out for the standard copoly (styrene-1%-divinylbenzene) support (Krchnak, et al., *Tetrahedron Lett.*, 1987, 4469).

While the solid-phase technique is presently preferred in the context of PNA and bis PNA synthesis, other methodologies or combinations thereof, for example, in combination with the solid-phase technique, apply as well: (1) the classical solution-phase methods for peptide synthesis (e.g., Bodanszky, *"Principles of Peptide Synthesis"*, Springer-Verlag, Berlin-New York 1984), either by stepwise assembly or by segment/fragment condensation, are of particular relevance when considering especially large scale productions (gram, kilogram) of PNA or bis PNA compounds; (2) the so-called "liquid-phase", strategy, which utilizes soluble polymeric supports such as linear polystyrene (Shemyakin, et al., *Tetrahedron Lett.*, 1965, 2323) and polyethylene glycol (PEG) (Mutter and Bayer, *Angew. Chem., Int. Ed. Engl.*, 1974, 13, 88), is useful; (3) random polymerization (see, e.g., Odian, *"Principles of Polymerization"*, McGraw-Hill, New York (1970)) yielding mixtures of many molecular weights ("polydisperse") peptide, PNA or bis PNA molecules are particularly relevant for purposes such as screening for antiviral effects; (4) a technique based on the use of polymer-supported amino acid active esters (Fridkin, et al., *J. Am. Chem. Soc.*, 1965, 87, 4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, PNA or bis PNA molecules, that can subsequently be used for fragment condensation into larger PNA or bis PNA molecules; (5) it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA or bis PNA molecules; (6) since antibodies can be generated to virtually any molecule of interest, the recently developed catalytic antibodies (abzymes), discovered simultaneously by the groups of Lerner (Tramantano, et al., *Science*, 1986, 234, 1566) and of Schultz (Pollack, et al., *Science*, 1986, 234, 1570), should also be considered as potential candidates for assembling PNA and bis PNA molecules. Thus, there has been considerable success in producing abzymes catalyzing acyl-transfer reactions (see for example Shokat, et al., *Nature*, 1989, 338, 269) (and references therein). Finally, completely artificial enzymes, very recently pioneered by Stewart's group (Hahn, et al., *Science*, 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty natural by occurring (proteinogenic) amino acids constituting peptides. In conclusion, no single strategy may be wholly suitable for the synthesis of a specific PNA or bis PNA molecule, and therefore, sometimes a combination of methods may work best.

The present invention also is directed to therapeutic or prophylactic uses for PNAs and bis PNAs. Likely therapeutic and prophylactic targets include herpes simplex virus (HSV), human papillomavirus (HPV), human immunodeficiency virus (HIV), candidia albicans, influenza virus, cytomegalovirus (CMV), intracellular adhesion molecules (ICAM), 5-lipoxygenase (5-LO), phospholipase $A_2$ ($PLA_2$), protein kinase C (PKC), and RAS oncogene. Potential applications of such targeting include treatments for ocular, labial, genital, and systemic herpes simplex I and II infections; genital warts; cervical cancer; common warts; Kaposi's sarcoma; AIDS; skin and systemic fungal infections; flu; pneumonia; retinitis and pneumonitis in immunosuppressed patients; mononucleosis; ocular, skin and systemic inflammation; cardiovascular disease; cancer; asthma; psoriasis; cardiovascular collapse; cardiac infarction; gastrointestinal disease; kidney disease; rheumatoid arthritis; osteoarthritis; acute pancreatitis; septic shock; Crohn's disease; and bacterial infections.

For therapeutic or prophylactic treatment, the PNAs and bis PNAs of the invention can be formulated in a pharmaceutical composition, which may include carriers, thickeners, diluents, buffers, preservatives, surface active agents and the like. Pharmaceutical compositions may also include one or more active ingredients such as antimicrobial agents, anti-inflammatory agents, anesthetics, and the like in addition to PNA or bis PNA.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic PNAs or bis PNAs. As used herein, therapeutics is meant to include the eradication of a disease state, by killing an organism or by control of erratic or harmful cellular growth or expression.

The present invention also pertains to the advantageous use of PNA and bis PNA molecules in solid-phase biochemistry (see, e.g., "Solid-Phase Biochemistry—Analytical and Synthetic Aspects", W. H. Scouten, ed., John Wiley & Sons, New York, 1983), notably solid-phase biosystems, especially bioassays or solid-phase techniques which concerns diagnostic detection/quantitation or affinity purification of complementary nucleic acids (see, e.g., "Affinity Chromatography—A Practical Approach", P. D. G. Dean, W. S. Johnson and F. A. Middle, eds., IRL Press Ltd., Oxford 1986; "Nucleic Acid Hybridization—A Practical Approach", B. D. Harnes and S. J. Higgins, IRL Press Ltd., Oxford 1987). Present day methods for performing such bioassays or purification techniques almost exclusively utilize "normal" or slightly modified oligonucleotides either physically adsorbed or bound through a substantially permanent covalent anchoring linkage to beaded solid supports such as cellulose, glass beads, including those with controlled porosity (Mizutani, et al., *J. Chromatogr.*, 1986, 356, 202), "Sephadex", "Sepharose", agarose, polyacrylamide, porous particulate alumina, hydroxyalkyl methacrylate gels, diol-bonded silica, porous ceramics, or contiguous materials such as filter discs of nylon and nitrocellulose. One example employed the chemical synthesis of oligo-dT on cellulose beads for the affinity isolation of poly A tail containing mRNA (Gilham in "*Methods in Enzymology,*" L. Grossmann and K. Moldave, eds., vol. 21, part D, page 191, Academic Press, New York and London, 1971). All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process. There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight. In contrast with oligonucleotides, PNA and bis PNA molecules are easier to attach onto solid supports because they contain strong nucleophilic and/or electrophilic centers. In addition, the direct assembly of oligonucleotides onto solid supports suffers from an extremely low loading of the immobilized molecule, mainly due to the low surface capacity of the materials that allow the successful use of the state-of-the-art phosphoramidite chemistry for the construction of oligonucleotides. (Beaucage and Caruthers, *Tetrahedron Lett.*, 1981, 22, 1859; Caruthers, *Science*, 1985, 232, 281). It also suffers from the fact that by using the alternative phosphite triester method (Letsinger and Mahadevan, *J. Am. Chem. Soc.* 1976, 98, 3655), which is suited for solid supports with a high surface/loading capacity, only relatively short oligonucleotides can be obtained. As for conventional solid-phase peptide synthesis, however, the latter supports are excellent materials for building up immobilized PNA and bis PNA molecules (the side-chain protecting groups are removed from the synthesized PNA or bis PNA chain without cleaving the anchoring linkage holding the chain to the solid support). Thus, PNA species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They also can be loaded onto solid supports in large amounts, thus further increasing the sensitivity/capacity of the solid-phase technique. Further, certain types of studies concerning the use of PNA in solid-phase biochemistry can be approached, facilitated, or greatly accelerated by use of the recently-reported "light-directed, spatially addressable, parallel chemical synthesis" technology (Fodor, et al., *Science*, 1991, 251, 767), a technique that combines solid-phase chemistry and photolithography to produce thousands of highly diverse, but identifiable, permanently immobilized compounds (such as peptides) in a substantially simultaneous way.

Additional objects, advantages, and novel features of this invention will become apparent to those skilled in the art upon examination of the following examples thereof, which are not intended to be limiting.

General Remarks

The following abbreviations are used in the experimental examples: egl, —NH—$CH_2$—$CH_2$—O—$CH_2$—$CH_2$—O—$CH_2$—C(=O)—; Aha, 6-amino hexanoic acid; DMF, N,N-dimethylformamide; DCC, N,N-dicyclohexyl carbodiimide; DCU, N,N-dicyclohexyl urea; THF, tetrahydrofuran; aeg, (2'-aminoethyl)glycine; pfp, pentafluorophenyl; Boc, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift;

NMR spectra were recorded on either a JEOL FX 90Q spectrometer, or a Bruker 250 MHz with tetramethylsilane as internal standard. Mass spectrometry was performed on a MassLab VG 12-250 quadropole instrument fitted with a VG FAB source and probe. Melting points were recorded on Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled before use. Dioxane was passed through basic alumina prior to use. t-Butyloxycarbonyl anhydride, 4-nitrophenol, methyl bromoacetate, benzyloxycarbonyl chloride, pentafluorophenol were all obtained through Aldrich Chemical Company. Thymine, cytosine, adenine were all obtained through Sigma.

Thin layer chromatography (Tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) or/and spraying with a ninhydrin solution (3 g ninhydrin in 1000 ml 1-butanol and 30 ml acetic acid), after heating at 120° C. for 5 min and, after spraying, heating again. Tlc plates were glass or plastic backed silica gel containing a fluorescent indicator.

EXAMPLE 1 tert-Butyl 4-Nitrophenyl Carbonate (1)

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was refluxed for 1 h, cooled to 0° C., filtered and concentrated to ⅓, and then poured into water (350 ml) at 0° C. After stirring for ½ h., the product was collected by filtration, washed with water, and then dried over sicapent, in vacuo. Yield 21.3 g (97%). M.p. 73.0–74.5° C. (litt. 78.5–79.5° C.). Anal. for $C_{11}H_{13}NO_5$ found(calc.) C: 55.20(55.23) H: 5.61(5.48) N: 5.82(5.85).

EXAMPLE 2

(N'-Boc-2'-Aminoethyl)glycine N-(2-Boc-Aminoethyl)glycine (2)

The title compound was prepared by a modification of the procedure by Heimer, et al. *Int. J. Pept.*, 1984, 23, 203–211 N-(2-Aminoethyl)glycine (3.00 g; 25.4 mmol) was dissolved in water (50 ml), dioxane (50 ml) was added, and the pH was adjusted to 11.2 with 2 N sodium hydroxide. tert-Butyl-4-nitrophenyl carbonate (1, 7.29 g; 30.5 mmol) was dissolved in dioxane (40 ml) and added dropwise over a period of 2 h, during which time the pH was maintained at 11.2 with 2 N sodium hydroxide. The pH was adjusted periodically to 11.2 for three more hours and then the solution was left overnight. The solution was cooled to 0° C. and the pH was carefully adjusted to 3.5 with 0.5 M hydrochloric acid. The aqueous solution was washed with chloroform (3×200 ml), the pH adjusted to 9.5 with 2N sodium hydroxide and the solution was evaporated to dryness, in vacuo (14 mmHg). The residue was extracted with DMF (25+2×10 ml) and the extracts filtered to remove excess salt. This results in a solution of the title compound in about 60% yield and greater than 95% purity by tlc (system 1 and visualised with ninhydrin, Rf=0.3). The solution was used in the following preparations of Boc-aeg derivates without further purification.

EXAMPLE 3

N-1-Carboxymethylthymine (3)

This procedure is different from the literature synthesis, but is easier, gives higher yields, and leaves no unreacted thymine in the product. To a suspension of thymine (40.0 g; 0.317 mol) and potassium carbonate (87.7 g; 0.634 mmol) in DMF (900 ml) was added methyl bromoacetate (30.00 ml; 0.317 mmol). The mixture was stirred vigorously overnight under nitrogen. The mixture was filtered and evaporated to dryness, in vacuo. The solid residue was treated with water (300 ml) and 4 N hydrochloric acid (12 ml), stirred for 15 min at 0° C., filtered, and washed with water (2×75 ml). The precipitate was treated with water (120 ml) and 2N sodium hydroxide (60 ml), and was boiled for 10 minutes. The mixture was cooled to 0° C., filtered, and the pure title compound was precipitated by the addition of 4 N hydrochloric acid (70 ml). Yield after drying, in vacuo over sicapent: 37.1 g (64%). $^1$H-NMR: (90 MHz; DMSO-$d_6$) 11.33 ppm (s, 1H, NH); 7.49 (d, J=0.92 Hz, 1H, ArH); 4.38 (s, 2H, CH$_2$); 1.76 (d, J=0.92 Hz, T—CH$_3$)

EXAMPLE 4

N-1-Carboxymethylthymine Pentafluorophenyl Ester (4)

N-1-Carboxymethylthymine (3, 10.0 g; 54.3 mmol) and pentafluorophenol (10.0 g; 54.3 mmol) were dissolved in DMF (100 ml) and cooled to 5° C. in ice water. DCC (13.45 g; 65.2 mmol) then was added. When the temperature passed below 5° C., the ice bath was removed and the mixture was stirred for 3 h at ambient temperature. The precipitated DCU was removed by filtration and washed twice with DMF (2×10 ml). The combined filtrate was poured into ether (1400 ml) and cooled to 0° C. Petroleum ether (1400 ml) was added and the mixture was left overnight. The title compound was isolated by filtration and was washed thoroughly with petroleum ether. Yield: 14.8 g (78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C: 44.79(44.59); H: 2.14(2.01) N: 8.13(8.00). FAB-MS: 443 (M+1+glycerol), 351 (M+1). $^1$H-NMR (90 MHz; DMSO-$d_6$): 11.52 ppm (s, 1H, NH); 7.64 (s, 1H, Ar H); 4.99 (s, 2H, CH$_2$); 1.76 (s, 3H, CH$_3$).

EXAMPLE 5

1-(Boc-aeg)thymine (5)

To the DMF-solution from Example 2 was added triethyl amine (7.08 ml; 50.8 mmol) followed by N-1-carboxymethylthymine pentafluorophenyl ester (4, 4.45 g; 12.7 mmol). The resultant solution was stirred for 1 h. The solution was cooled to 0° C. and treated with cation exchange material ("Dowex 5W X-8", 40 g) for 20 min. The cation exchange material was removed by filtration, washed with dichloromethane (2×15 ml), and dichloromethane (150 ml) was added. The resulting solution was washed with saturated sodium chloride, dried over magnesium sulfate, and evaporated to dryness, in vacuo, first by a water aspirator and then by an oil pump. The residue was shaken with water (50 ml) and evaporated to dryness. This procedure was repeated once. The residue then was dissolved in methanol (75 ml) and poured into ether (600 ml) and petroleum ether (1.4 L). After stirring overnight, the white solid was isolated by filtration and was washed with petroleum ether. Drying over sicapent, in vacuo, gave 3.50 g (71.7%). M.p. 142–147° C. Anal. for $C_{16}H_{24}N_4O_7$. Found(calc.) C: 49.59(50.00) H: 6.34(6.29) N: 14.58(14.58). $^1$H-NMR (250 MHz, DMSO-$d_6$): Due to the limited rotation around the secondary amide bond several of the signals were doubled in the ratio 2:1, (indicated in the list by mj. for major and mi. for minor). 12.73 ppm (b, 1H, —CO$_2$H); 11.27 ppm (s, mj., imide); 11.25 ppm (s, mi., imide); 7.30 ppm (s, mj., ArH); 7.26 ppm (s, mi., ArH); 6.92 ppm (unres. t, mj., BocNH); 6.73 ppm (unres. t; mi., BocNH); 4.64 ppm (s, mj., T—CH$_2$—CO—); 4.47 ppm (s, mi., T—CH$_2$—CO—); 4.19 ppm (s, mi., CONRCH$_2$CO$_2$H); 3.97 ppm (s, mj., CONRCH$_2$CO$_2$H); 3.41–2.89 ppm (unres. m, —CH$_2$CH$_2$— and water); 1.75 ppm (s, 3H, T—CH$_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C$_5$"); 141.92 (C$_6$"); 108.04 (C2'); 77.95 and 77.68 (Thy-CH$_2$CO); 48.96, 47.45 and 46.70 (—CH$_2$CH$_2$— and NCH$_2$CO$_2$H); 37.98 (Thy-CH$_3$); 28.07 (t-Bu). FAB-MS: 407 (M+Na$^+$); 385 (M+H$^+$).

EXAMPLE 6

1-(Boc-aeg)thymine Pentafluorophenyl Ester (6, Boc-Taeg.OPfp)

1-(Boc-aeg)thymine (5) (2.00 g; 5.20 mmol) was dissolved in DMF (5 ml) and methylene chloride (15 ml) was added. Pentafluorophenol (1.05 g; 5.72 mmol) was added and the solution was cooled to 0° C. in an ice bath. DDC then was added (1.29 g; 6.24 mmol) and the ice bath was removed after 2 min. After 3 h with stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 ml) and poured into water (200 ml) at 0° C. The title compound was isolated by filtration, washed with water, and dried over sicapent, in vacuo. Yield: 2.20 g (77%). An analytical sample was obtained by recrystallisation from 2-propanol. M.p. 174–175.5° C. Analysis for C$_{22}$H$_{23}$N$_4$O$_7$F$_5$, found(-calc.): C: 48.22(48.01); H: 4.64(4.21); N: 9.67(10.18). $^1$H-NMR (250 MHz, CDCl$_3$): Due to the limited rotation around the secondary amide bond several of the signals were doubled in the ratio 6:1 (indicated in the list by mj. for major and mi. for minor). 7.01 ppm (s, mi., ArH); 6.99 ppm (s, mj., ArH); 5.27 ppm (unres. t, BocNH); 4.67 ppm (s, mj., T—CH$_2$—CO—); 4.60 ppm (s, mi., T—CH$_2$—CO—); 4.45 ppm (s, mj., CONRCH$_2$CO$_2$PfP); 4.42 ppm (s, mi., CONRCH$_2$CO$_2$Pfp); 3.64 ppm (t, 2H, BocNHCH$_2$CH$_2$—); 3.87 ppm ("q", 2H, BocNHCH$_2$CH$_2$—); 1.44 (s, 9H, t-Bu). FAB-MS: 551 (10; M+1); 495 (10; M+1–tBu); 451 (80; –Boc)

EXAMPLE 7

N-Benzyloxycarbonyl-N'-(bocaminoethyl)glycine (7)

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2 N NaOH at 0° C. Benzyloxycarbonyl chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml). Yield 124.7 g (79%). M.p. 64.5–85° C. Anal. for C$_{17}$H$_{24}$N$_2$O$_6$ found(calc.) C: 58.40(57.94); H: 7.02(6.86); N: 7.94(7.95). $^1$H-NMR (250 MHz, CDCl$_3$) 7.33 & 7.32 (5H, Ph); 5.15 & 5.12 (2H, PhCH$_2$); 4.03 & 4.01 (2H, NCH$_2$CO$_2$H); 3.46 (b, 2H, BocNHCH$_2$CH$_2$); 3.28 (b, 2H, BocNHCH$_2$CH$_2$); 1.43 & 1.40 (9H, $^t$Bu). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 8

N'-Boc-aminoethyl Glycine Ethyl Ester (8)

N-Benzyloxycarbonyl-N'-(bocaminoethyl)glycine (7, 60.0 g; 0.170 mol) and N,N-dimethyl-4-aminopyridine (6.00 g) were dissolved in absolute ethanol (500 ml), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g SiO$_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, CD$_3$OD); 4.77 (b. s, NH); 4.18 (q, 2H, MeCH$_2$—); 3.38 (s, 2H, NCH$_2$CO$_2$Et); 3.16 (t, 2H, BocNHCH$_2$CH$_2$); 2.68 (t, 2H, BocNHCH$_2$CH$_2$); 1.43 (s, 9H, $^t$Bu) and 1.26 (t, 3H, CH$_3$) $^{13}$C-NMR 171.4 (COEt); 156.6 (CO); 78.3 ((CH$_3$)$_3$C); 59.9 (CH$_2$); 49.0 (CH$_2$); 48.1 (CH$_2$); 39.0 (CH$_2$); 26.9 (CH$_2$) and 12.6 (CH$_3$).

EXAMPLE 9

N'-Boc-aminoethyl Glycine Methyl Ester (9)

The above procedure was used, with methanol being substituted for ethanol. The final product was purified by flash column chromatography.

EXAMPLE 10

1-(Boc-aeg)thymine Ethyl Ester (10)

N'-Boc-aminoethyl glycine ethyl ester (8, 13.5 g; 54.8 mmol), DhbtOH (9.84 g; 60.3 mmol) and N-1-carboxymethyl thymine (4, 11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration, The organic phase was dried over magnesium sulfate and evaporated to dryness, in vacuo. The oily residue was dissolved in methylene chloride (150 ml), filtered, and the title compound was precipitated by the addition of petroleum ether (350 ml) at 0° C. The methylene chloride/petroleum ether procedure was repeated once. This afforded 16.0 g (71%) of the title compound which was more than 99%. pure by HPLC.

EXAMPLE 11

1-(Boc-aeg)thymine (6a)

The material from Example 10 was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to the solution which was then washed with methylene chloride (300 ml). Additional water (30 ml) was added, and the alkaline solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts were dried over magnesium sulfate and were evaporated to dryness, in vacuo. The residue was evaporated once from methanol, which after drying overnight afforded a colorless glassy solid. Yield 9.57 g (64%). HPLC >98% $R_T$=14.8 min. Anal. for $C_{16}H_{24}N_4O_7 \cdot 0.25\ H_2O$ Found (calc.) C: 49.29 (49.42); H: 6.52(6.35); N: 14.11 (14.41). Due to the limited rotation around the secondary amide, several of the signals were doubled in the ratio 2:1 (indicated in the list by mj. for major and mi. for minor). $^1$H-NMR (250 MHz, DMSO-$d_6$): 12.75 (b.s., 1H, $CO_2H$); 11.28 (s, "1H", mj., imide NH); 11.26 (s, "1H", mi., imide NH); 7.30 (s, "1H", mj., T H-6); 7.26 (s, "1H", mi., T H-6); 6.92 (b.t., "1H", mj., BocNH); 6.73 (b.t., "1H", mi., BocNH); 4.64 (s, "2H", mj., C$\underline{H}_2$CON); 4.46 (s, "2H", mj., C$\underline{H}_2$CON); 4.19 (s, "2H", mi., C$\underline{H}_2$CO$_2$H); 3.97 (s, "2H", mj., C$\underline{H}_2$CO$_2$H); 3.63–3.01 (unresolved m, includes water, C$\underline{H}_2$C$\underline{H}_2$); 1.75 (s, 3H, C$\underline{H}_3$) and 1.38 (s, 9H, $^t$Bu)

EXAMPLE 12

N-4-Benzyloxycarbonyl Cytosine (12)

Over a period of about 1 h, benzyloxycarbonyl chloride (52 ml; 0.36 mol) was added dropwise to a suspension of cytosine (8, 20.0 g; 0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo. Yield 24.7 g (54%). M.p. >250° C. Anal. for $C_{12}H_{11}N_3O_3$. Found(calc.); C: 58.59(58.77); H: 4.55 (4.52); N: 17.17(17.13). No NMR spectra were recorded since it was not possible to get the product dissolved.

EXAMPLE 13

N-4-Benzyloxycarbonyl-N-1-carboxymethyl Cytosine (13)

In a three necked round bottomed flask equipped with mechanical stirring and nitrogen coverage was placed methyl bromacetate (7.82 ml; 82.6 mmol) and a suspension of N-4-benzyloxycarbonyl cytosine (12, 21.0 g; 82.6 mmol) and potassium carbonate (11.4 g; 82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal. for $C_{14}H_{13}N_3O_5$. Found(calc.); C: 55.41 (55.45); H: 4.23(4.32); N: 14.04(13.86). $^1$H-NMR (90 MHz; DMSO-$d_6$): 8.02 ppm (d, J=7.32 Hz, 1H, H-6); 7.39 (s, 5H, Ph); 7.01 (d, J=7.32 Hz, 1H, H-5); 5.19 (s, 2H, PhC$\underline{H}_2$—); 4.52 (s, 2H).

EXAMPLE 14

N-4-Benzyloxycarbonyl-N-1-carboxymethyl Cytosine Pentafluorophenyl Ester (14)

N-4-Benzyloxycarbonyl-N-1-carboxymethyl-cytosine (13, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for $C_{20}H_{12}N_3F_5O_5$. Found(calc.); C: 51.56(51.18); H: 2.77(2.58); N: 9.24(8.95). $^1$H-NMR (90 MHz; CDCl$_3$): 7.66 ppm (d, J=7.63 Hz, 1H, H-6); 7.37 (s, 5H, Ph); 7.31 (d, J=7.63 Hz, 1H, H-5); 5.21 (s, 2H, PhC$\underline{H}_2$—); 4.97 (s, 2H, NC$\underline{H}_2$—). FAB-MS: 470 (M+1)

EXAMPLE 15

N-4-Benzyloxycarbonyl-1-Boc-aeg-cytosine (15)

To a solution of (N-Boc-2-aminoethyl)glycine 2, in DMF, prepared as described in Example 2, was added triethyl amine (7.00 ml; 50.8 mmol) and N-4-benzyloxycarbonyl-N-1-carboxymethyl-cytosine pentafluorophenyl ester (14, 2.70 g; 5.75 mmol). After stirring the solution for 1 h at room temperature, methylene chloride (150 ml), saturated sodium chloride (250 ml), and 4 N hydrochloric acid to pH~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C. (decomp.). $^1$H-NMR (250 MHz, CDCl$_3$): Due to the limited rotation around the secondary amide bond several of the signals were doubled in the ratio 2:1, (indicated in the list by mj. for major and mi. for minor). 7.88 ppm (dd, 1H, H-6); 7.39 (m, 5H, Ph); 7.00 (dd, 1H, H-5); 6.92 (b, 1H, BocN$\underline{H}$); 6.74 (b, 1H, ZN$\underline{H}$)—?; 5.19 (s, 2H, Ph—C$\underline{H}_2$); 4.81 ppm (s, mj., Cyt-CH$_2$—CO—); 4.62 ppm (s, mi., Cyt-CH$_2$—CO—); 4.23 (s, mi., CONRC$\underline{H}_2$CO$_2$H); 3.98 ppm (s, mj., CONRC$\underline{H}_2$CO$_2$H); 3.42–3.02 (unres. m, —CH$_2$CH$_2$— and water); 1.37 (s, 9H, tBu). FAB-MS: 504 (M+1); 448 (M+1–tBu).

EXAMPLE 16

N-4-Benzyloxycarbonyl-1-Boc-aeg-cytosine Pentafluorophenyl Ester (16)

N-4-Benzyloxycarbonyl-1-Boc-aeg-cytosine (15, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over sicapent, in vacuo. Yield 1.30 g (65%). Analysis for C$_{29}$H$_{28}$N$_5$O$_8$F$_5$. Found(calc.); C: 52.63(52.02); H: 4.41(4.22); N: 10.55(10.46). $^1$H-NMR (250 MHz; DMSO-d$_6$): showed essentially the spectrum of the above acid, most probably due to hydrolysis of the ester. FAB-MS: 670 (M+1); 614 (M+1–tBu)

EXAMPLE 17

N-4-Benzyloxycarbonyl-1-(Boc-aeg)cytosine (17)

N'-Boc-aminoethyl glycine ethyl ester (8, 5.00 g; 20.3 mmol), DhbtOH (3.64 g; 22.3 mmol) and N-4-benzyloxycarbonyl-N-1-carboxymethyl cytosine (13, 6.77 g; 22.3 mmol) were suspended in DMF (100 ml). Methylene chloride (100 ml) then was added. The solution was cooled to 0° C. and DCC (5.03 g; 24.4 mmol) was added. The ice bath was removed after 2 h and stirring was continued for another hour at ambient temperature. The reaction mixture then was evaporated to dryness, in vacuo. The residue was suspended in ether (100 ml) and stirred vigorously for 30 min. The solid material was isolated by filtration and the ether wash procedure was repeated twice. The material was then stirred vigorously for 15 min with dilute sodium hydrogencarbonate (aprox. 4% solution, 100 ml), filtered and washed with water. This procedure was then repeated once, which after drying left 17.0 g of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for 15 minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% R$_T$=19.5 min, and a minor impurity at 12.6 min (approx. 1%) most likely the Z-de protected monomer. Anal. for C$_{23}$H$_{29}$N$_5$O$_8$ found(calc.) C: 54.16(54.87); H: 5.76(5.81) and N: 13.65(13.91). $^1$H-NMR (250 MHz, DMSO-d$_6$). 10.78 (b.s, 1H, CO$_2$$\underline{H}$); 7.88 (2 overlapping dublets, 1H, Cyt H-5); 7.41–7.32 (m, 5H, Ph); 7.01 (2 overlapping doublets, 1H, Cyt H-6); 6.94 & 6.78 (unres. triplets, 1H, BocN$\underline{H}$); 5.19 (s, 2H, PhC$\underline{H}_2$); 4.81 & 4.62 (s, 2H, C$\underline{H}_2$CON); 4.17 & 3.98 (s, 2H, C$\underline{H}_2$CO$_2$H); 3.42–3.03 (m, includes water, C$\underline{H}_2$C$\underline{H}_2$) and 1.38 & 1.37 (s, 9H, $^t$Bu). $^{13}$C-NMR. 150.88; 128.52; 128.18; 127.96; 93.90; 66.53; 49.58 and 28.22. IR: Frequency in cm$^{-1}$ (intensity). 3423 (26.4), 3035 (53.2), 2978(41.4), 1736(17.3), 1658(3.8), 1563(23.0), 1501(6.8) and 1456 (26.4).

EXAMPLE 18

9-Carboxymethyl Adenine Ethyl Ester (18)

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5–220° C. Anal. for C$_9$H$_{11}$N$_5$O$_2$ found(calc.): C: 48.86 (48.65); H: 5.01(4.91); N: 31.66(31.42). $^1$H-NMR (250 MHz; DMSO-d$_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0), 1671(1.8), 1644(10.9), 1606(0.6), 1582(7.1), 1522(43.8), 1477(7.2), 1445(35.8) and 1422(8.6). The position of alkylation was verified by X-ray crystallography on crystals, which were obtained by recrystallization from 96% ethanol.

Alternatively, 9-carboxymethyl adenine ethyl ester 18, can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) haxane washed sodium hydride-mineral oil dispersion. The mixture was stirred vigorously for 2 hours, then ethyl bromacetate 75 ml, 0.67 mol) was added dropwise over the course of 3 hours. The mixture was stirred for one additional hour, whereafter tlc indicated complete conversion of adenine. The mixture was evaporated to dryness at 1 mmHg and water (500 ml) was added to the oily residue which caused crystallization of the title compound. the solid was recrystallized from 06% ethanol (600 ml). Yield after drying 53.7 (65.6%). HPLC (215 nm) purity >99.5%.

EXAMPLE 19

N-6-Benzyloxycarbonyl-9-carboxymethyl Adenine Ethyl Ester (19)

9-Carboxymethyladenine ethyl ester (18, 3.40 g, 15.4 mmol) was dissolved in dry DMF (50 ml) by gentle heating, cooled to 20° C., and added to a solution of N-ethyl-benzyloxy-carbonylimidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleum ether (50 ml). This procedure was repeated once to give 3.45 g (63%) of the title compound. M.p. 132–35° C. Analysis for $C_{17}H_{17}N_5O_4$ found (calc.): C: 56.95(57.46); H: 4.71(4.82); N: 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N—C$\underline{H}_2$); 4.96 (s, 2H, Ph—C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+—CO$_2$). IR: frequency in cm$^{-1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 1492(37.9); 1465(14.0) and 1413(37.3).

EXAMPLE 20

N-6-Benzyloxycarbonyl-9-carboxymethyl Adenine (20)

N-6-Benzyloxycarbonyl-9-carboxymethyladenine ethyl ester (19, 3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50 ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C: 46.32(55.05); H: 4.24(4.00); N: 18.10 (21.40) and C/N: 2.57(2.56). $^1$H-NMR (250 MHz; DMSO-d$_6$): 8.70 (s, 2H, H-2 and H-8); 7.50–7.35 (m, 5H, Ph); 5.27 (s, 2H, N—C$\underline{H}_2$); and 5.15 (s, 2H, Ph—C$\underline{H}_2$). $^{13}$C-NMR. 168.77, 152.54, 151.36, 148.75, 145.13, 128.51, 128.17, 127.98, 66.76 and 44.67. IR (KBr) 3484(18.3); 3109(15.9); 3087(15.0); 2966(17.1); 2927(19.9); 2383(53.8); 1960 (62.7); 1739(2.5); 1688(5.2); 1655(0.9); 1594(11.7); 1560 (12.3); 1530(26.3); 1499(30.5); 1475(10.4); 1455(14.0); 1429(24.5) and 1411(23.6). FAB-MS: 328 (MH+) and 284 (MH+—CO$_2$). HPLC (215 nm, 260 nm) in system 1: 15.18 min, minor impurities all less than 2%.

EXAMPLE 21

N-6-Benzyloxycarbonyl-1-(Boc-aeg)adenine Ethyl Ester (21)

N'-Boc-aminoethyl glycine ethyl ester (8, 2.00 g; 8.12 mmol), DhbtOH (1.46 g; 8.93 mmol) and N-6-benzyloxycarbonyl-9-carboxymethyl adenine (20, 2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95% . Anal. for $C_{26}H_{33}N_7O_7.2O$ found(calc.) C: 55.01(54.44; H: 6.85 (6.15) and N: 16.47(17.09). $^1$H-NMR (250 MHz, CDCl$_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BocNH); 5.30 (s, 2H, PhCH$_2$); 5.16 & 5.00 (s, 2H, C$\underline{H}_2$CON); 4.29 & 4.06 (s, 2H, C$\underline{H}_2$CO$_2$H); 4.20 (q, 2H, OC$\underline{H}_2$CH$_3$); 3.67–3.29 (m, 4H, C$\underline{H}_2$C$\underline{H}_2$); 1.42 (s, 9H, $^t$Bu) and 1.27 (t, 3H, OCH$_2$C$\underline{H}_3$). The spectrum shows traces of ethanol and DCU.

EXAMPLE 22

N-6-Benzyloxycarbonyl-1-(Boc-aeg)adenine (22)

N-6-Benzyloxycarbonyl-1-(Boc-aeg)adenine ethyl ester (21, 1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, affording 0.82 g (58%). The product reprecipitated twice with methylene chloride/petroleum ether, 0.77 g (55%) after drying. M.p. 119° C. (decomp.) Anal. for $C_{24}H_{29}N_7O_7.H_2O$ found(calc.) C: 53.32(52.84); H: 5.71 (5.73); N: 17.68(17.97). FAB-MS. 528.5 (MH+). $^1$H-NMR (250 MHz, DMSO-d$_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BocNH); 5.33 & 5.16 (s, 2H, CH$_2$CON); 5.22 (s, 2H, PhC$\underline{H}_2$); 4.34–3.99 (s, 2H, CH$_2$CO$_2$H); 3.54–3.03 (m's, includes water, C$\underline{H}_2$C$\underline{H}_2$) and 1.39 & 1.37 (s, 9H, $^t$Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 23

2-Amino-6-chloro-9-carboxymethylpurine (23)

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over sicapent. Yield (3.02 g; 44.8%). $^1$H-NMR (DMSO-d6): d=4.88 ppm (s, 2H); 6.95 (s, 2H); 8.10 (s, 1H).

EXAMPLE 24

2-Amino-6-benzyloxy-9-carboxymethylpurine (24)

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (23, 4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacuo, over sicapent: 2.76 g (52%). M.p. 159–65° C. Anal. (calc., found) C(56.18; 55.97), H(4.38; 4.32), N(23.4; 23.10). $^1$H-NMR (DMSO-d$_6$): 4.82 ppm. (s, 2H); 5.51 (s, 2H) 6.45 (s, 2H); 7.45 (m, 5H); 7.82 (s, 1H).

EXAMPLE 25

N-([2-Amino-6-benzyloxy-purine-9-yl]-acetyl)-N-(2-Boc-aminoethyl)-glycine [BocGaeg Monomer] (25)

2-Amino-6-benzyloxy-9-carboxymethyl-purine (24, 0.50 g; 1.67 mmol), N'-Boc-aminoethyl glycine methyl ester (0.65 g; 2.80 mmol), diisopropylethyl amine (0.54 g; 4.19 mmol), and bromo-tris-pyrrolidino-phosphonium-hexafluoro-phosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3×40 ml). The organic layer was washed with potassium hydrogen sulfate solution (1 N; 2×40 ml), sodium hydrogen carbonate (1 N; 1×40 ml) and saturated sodium chloride solution (60 ml). After drying with anhydrous sodium sulfate and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^1$H-NMR(250, MHz, DMSO-d$_6$): d=1.4 ppm. (s, 9H); 3.2 (m, 2H); 3.6 (m, 2H); 4.1 (s, mj., CONRC$\underline{H}_2$COOH); 4.4 (s, mi., CONRC $\underline{H}_2$COOH); 5.0 (s, mi., Gua-C$\underline{H}_2$CO—); 5.2 (s, mj., Gua-C $\underline{H}_2$CO); 5.6 (s, 2H); 6.5 (s, 2H); 6.9 (m, mi., BocNH); 7.1 (m, mj., BocNH); 7.5 (m., 3H); 7.8 (s, 1H); 12,8 (s; 1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 26

Methyl α-Formylsuccinate, FIG. 1 (26a)

In a modification of the procedure of Fissekis and Sweet, *Biochemistry* 1970, 9, 3136–42, sodium methoxide (40.5 g, 0.75 mol) was suspended in dry ether (500 ml) and stirred under nitrogen at 0° C. A mixture of dimethylsuccinate (65.4 ml, 0.50 mol) and methylformate (123 ml, 2.00 mol) was added dropwise over 30 min. The reaction mixture was stirred at 0° C. for 2 hours and then at room temperature overnight. Subsequently, the reaction mixture was evaporated to a viscous brown residue which was washed once with petroleum ether and then dissolved in 3 M hydrochloric acid (160 ml). This solution was made weakly acidic with concentrated hydrochloric acid and then extracted with dichloromethane (4×250 ml). The organic phase was dried (MgSO$_4$), filtered and evaporated under reduced pressure. The resulting residue was distilled in a kugelrohr apparatus at 60° C. and 0.6 mBar yielding 52.3 g of a mixture of the title compound and dimethyl succinate in the molar ratio 80:20 (determined by NMR) as a colorless oil. This mixture can be used directly in the following preparation. The product can be isolated free of dimethyl succinate by exchanging the extraction with dichloromethane with a continuous extraction with diethyl ether. However, in our hands this reduced the yield to 34%. Fissekis and Sweet, ibid, had reported a 62% yield. $^1$H-NMR (DMSO-d$_6$/TMS): δ=3.20 (s, 2H, CH$_2$); 3.59 (s, 3H, OMe); 3.61 (s, 3H, OMe); 7.73 (s, 1H, C$\underline{H}$OH); 10.86 (br s, 1H, CH$\underline{OH}$). $^{13}$C-NMR (DMSO-d$_6$/TMS): δ=28.9 (CH$_2$); 51.0 (OMe); 51.6 (OMe); 102.1 ($\underline{C}$=CHOH); 156.6 (CHOH); 168.3 (COO); 171.7 (COO).

EXAMPLE 27

Isocytosin-5-ylacetic Acid (27)

In a modification of the procedure of Beran et al., *Collect. Czech. Chem. Commun*. 1983, 48, 292–8, sodium methoxide (41.9 g, 0.78 mol) was dissolved in dry methanol (200 ml) and guanidine hydrochloride (49.4 g, 0.52 mol) was added. The mixture was stirred for 10 min under nitrogen at room temperature. A solution of methyl α-formylsuccinate (26, 30.0 g, 0.17 mol) in dry methanol (100 ml) was added to the mixture. The reaction mixture was refluxed under nitrogen for 3 hours and then stirred at room temperature overnight. Subsequently, the reaction mixture was filtered, and the filter cake was washed once with methanol. The collected filtrate and washing were evaporated under reduced pressure. The resulting residue was dissolved in water (80 ml) and the solution was acidified with concentrated hydrochloric acid to pH 4.2. After having been stirred at 0° C. the mixture was filtered, the precipitate washed once with water and then freeze-dried leaving 28.29 g (97%) of the title compound as a white solid. Calcd. for C$_6$H$_7$N$_3$O$_3$1/2H$_2$O: C, 40.45; H, 4.53; N, 23.59. Found: C, 40.13; H, 4.22; N, 23.26.

Due to the poor solubility properties of the product it was further characterized as its sodium salt. 27 (0.42 g, 2.5 mmol) and sodium bicarbonate were dissolved in boiling water (35 ml). The solution was cooled and evaporated. The residue was dissolved in water (6 ml) and ethanol (4 ml) and isopropanol (8 ml) were added. The sodium salt of 27 was collected by filtration, washed with abs. ethanol and petroleum ether and dried to yield 0.31 g (65%) as white crystals. $^1$H-NMR (D$_2$O/TMS): δ=3.10 (s, 2H, CH$_2$COO); 7.40 (s, 1H, H-6). $^{13}$C-NMR (DMSO-d$_6$/TMS): δ=34.8 (CH$_2$COO); 112.0 (C-5); 145.6–146.5 (m, C-2); 155.1 (C-6); 169.4 (C-4); 179.3 (COOH). MS (FAB+) m/z (%): 192 (100, M+H).

EXAMPLE 28

Methyl Isocytosin-5-ylacetate (28)

Thionylchloride (3.6 ml, 50 mmol) was added to stirred methanol (210 ml) at −40° C. under nitrogen. Isocytosin-5-ylacetic acid (27, 7.0 g, 41 mmol) was added and the reaction mixture was stirred at room temperature for 1 hour, at 60° C. for 3 hours and overnight at room temperature. The reaction mixture was evaporated to dryness and the residue was dissolved in saturated aqueous sodium bicarbonate (80 ml) giving a foamy precipitate. 4 M hydrochloric acid was added to pH 6.5 and the suspension was stirred for 1 hour. The precipitate was collected by filtration, washed with water, recrystallized from water and freeze-dried yielding 4.66 g (62%) of methyl isocytosin-5-ylacetate as white crystals.

$^1$H-NMR (DMSO-d$_6$/TMS): δ=3.28 (s, 2H, CH$_2$COO); 3.64 (s, 3H, COOMe); 6.87 (br s, 2H, NH$_2$); 7.54 (s, 1H, H-6). $^{13}$C-NMR (DMSO-d$_6$/TMS): δ=32.0 (CH$_2$COO); 51.5 (COOMe); 108.4 (C-5); 153.3 (C-2); 156.4 (C-6); 164.0 (C-4); 171.8 (CH$_2$COO). MS(FAB+) m/z (%) 184 (100, M+H). Calcd. for C$_7$H$_9$N$_3$O$_3$/2H$_2$O: C, 40.00; H, 5.75; N, 19.99. Found: C, 40.18; H, 5.46; N, 20.30.

EXAMPLE 29

Methyl N-2-(Benzyloxycarbonyl)isocytosin-5-ylacetate (29)

Methyl isocytosin-5-ylacetate (28, 9.5 g, 52 mmol) was dissolved in dry DMF (95 ml) and the solution was stirred at 0° C. under nitrogen. N-Benzyloxycarbonyl-N'-methylimidazolium triflate (37.99 g, 104 mmol) was added slowly. The reaction mixture was stirred for 30 min at 0° C. and then overnight at room temperature. Dichloromethane (800 ml) was added and the resultant mixture was washed with half-saturated aqueous sodium bicarbonate (2×400 ml), half-saturated aqueous potassium hydrogen sulfate (2×400 ml) and with brine (1×400 ml). The organic phase was dried (MgSO$_4$), filtered and evaporated under reduced pressure. The residue was recrystallized from methanol affording 13.32 g (81%) of the title compound as white crystals. $^1$H-NMR (DMSO-d$_6$/TMS): δ=3.43 (s, 2H, CH$_2$COO); 3.67 (s, 3H, COOMe); 5.30 (s, 2H, PhCH$_2$); 7.43–7.52 (m, 5H, PhCH$_2$); 7.77 (s, 1H, H-6). $^{13}$C-NMR (DMSO-d$_6$/TMS): δ=31.9 (CH$_2$COO); 51.6 (COOMe); 67.0 (PhCH$_2$); 128.1–128.5 (m, PhCH$_2$); 135.7 (PhCH$_2$); 150.7 (Z—CO); 170.8 (COO). MS (FAB+) m/z (%): 318 (3.5, M+H) Calcd. for C$_{15}$H$_{15}$N$_3$O$_5$: C, 56.78; H, 4.76; N, 13.24. Found: C, 56.68; H, 4.79; N, 13.28.

EXAMPLE 30

N-2(Benzyloxycarbonyl)isocytosin-5-ylacetic Acid (30)

Methyl N-2(benzyloxycarbonyl)isocytosin-5-ylacetate (29, 5.2 g, 16 mmol) was suspended in THF (52 ml) and cooled to 0° C. 1 M lithium hydroxide (49 ml, 49 mmol) was added and the reaction mixture was stirred at 0° C. for 25 min. Additional 1 M lithium hydroxide (20 ml, 20 mmol) was added and the mixture was stirred at 0° C. for 90 min. The product was precipitated by acidifying to pH 2 with 1 M hydrochloric acid, collected by filtration, washed once with water and dried to yield 4.12 g (83%) of white crystals. $^1$H-NMR (DMSO-d$_6$/TMS): δ=3.33 (s, 2H, CH$_2$COO); 5.29 (s, 2H, PhCH$_2$); 7.43–7.52 (m, 5H, PhCH$_2$); 7.74 (s, 1H, H-6); 11.82 (br s, 3H, exchangeable protons). MS (FAB+) m/z (%): 304 (12, M+H) Calcd. for C$_{14}$H$_{13}$N$_3$O$_5$: C, 55.45; H, 4.32; N, 13.86. Found: C, 55.55; H, 4.46; N, 13.84.

EXAMPLE 31

Ethyl N-(2-BOC-aminoethyl)-N-(N-2 (benzyloxycarbonyl)isocytosin-5-ylacetyl)glycinate (31)

N-2 (Benzyloxycarbonyl)isocytosin-5-ylacetic acid (30, 2.0 g, 6.6 mmol) was transferred to a flask equipped with a stirring bar and a septum through which a flow of nitrogen was applied. Dry DMF (20 ml) and N-methylmorpholine (2.2 ml, 19.8 mmol) were added. The mixture was cooled to 0° C. and ethyl N-(2-BOC-aminoethyl)glycinate (1.8 g, 7.3 mmol) and O-benzotriazol-1-yl-N,N,N',N'-tetramethyluronium hexafluorophosphate (HBTU, 3.0 g, 7.9 mmol) were added. The reaction mixture was stirred under nitrogen for 4 h followed by addition of dichloromethane (100 ml). The organic phase was washed with half-saturated aqueous sodium bicarbonate (2×75 ml), half-saturated aqueous potassium hydrogen sulfate (2×75 ml) and with brine (1×75 ml), dried (MgSO$_4$), filtered and evaporated under reduced pressure. The residue was dissolved in ethyl acetate (50 ml), stirred at 0° C. for 10 min and filtered through celite which was washed with ethyl acetate. The collected filtrate and washing were concentrated to a volume of 10 ml. Diethyl ether (100 ml) was added and the resultant solution was stirred overnight at room temperature. The product was collected by filtration, washed once with diethyl ether and dried to yield 2.6 g (74%) of the title compound as white crystals. Due to hindered rotation around the amide bond several of the NMR signals are comprised of a major (ma) and minor (mi) component. $^1$H-NMR (DMSO-d$_6$/TMS): δ=1.20–1.30 (m, 3H, CH$_2$CH); 1.45 (s, 9H, BOC); 3.05–3.52 (m, 6H, NCH$_2$, CH$_2$N, CH$_2$CON); 4.08 and 4.40 (s, ma and s, mi, respectively, 2H, CH$_2$COO); 4.15 and 4.25 (q, ma, J=7 Hz and q, mi, respectively, 2H, CH$_2$CH$_3$); 5.29 (s, 2H, PhCH$_2$); 7.40–7.52 (m, 5H, PhCH$_2$); 7.64 and 7.67 (s, mi and s, ma, respectively, 1H, H-6). $^{13}$C-NMR (DMSO-d$_6$/TMS): δ=14.1 (CH$_2$CH$_3$); 28.2 (BOC); 30.2 and 30.5 (ma and mi, respectively, CH$_2$CON); 37.9 and 38.3 (mi and ma, respectively, NCH$_2$); 47.7 and 48.0 (ma and mi, respectively, CH$_2$N); 50.2 (CH$_2$COO); 60.4 and 61. 0 (ma and mi, respectively, CH$_2$CH$_3$); 67.0 (PhCH$_2$); 127. 9–128.5 (m, PhCH$_2$); 135.8 (phCH$_2$); 155.7 (C-6), 169.4 (CON); 170.0 (COO). MS (FAB+) m/z (%): 532 (3.5, M+H); 432 (3.5, M-BOC+H) Calcd. for C$_{25}$H$_{33}$N$_5$O$_8$: C, 56.49; H, 6.26; N, 13.17. Found: C, 56.46; H, 6.14; N, 12.86.

EXAMPLE 32

N-(2-BOC-aminoethyl)-N-(N-2-(benzyloxycarbonyl)isocytosin-5-ylacetyl)glycinate (32)

Ethyl N-(2-BOC-aminoethyl)-N-(N-2-(benzyloxycarbonyl)isocytosin-5-ylacetylglycinate (31, 1.6 g, 3.0 mmol) was dissolved in methanol (16 ml) by gentle heating. The solution was cooled to 0° C. and 2 M sodium hydroxide (23 ml) was added. The reaction mixture was stirred at room temperature for 75 min and then cooled to 0°

C. again. The pH was adjusted to 1.7 and the product was collected by filtration, washed once with water and dried to give 1.24 g (82%) of 32 as white crystals.

Due to hindered rotation around the amide bond several of the NMR signals are comprised of a major (ma) and minor (mi) component. $^1$H-NMR (DMSO-d$_6$/TMS): δ=1.45 (s, 9H, BOC); 3.05–3.52 (m, 6H, NCH$_2$, CH$_2$N, CH$_2$CON); 4.01 and 4.29 (s, ma and s, mi, respectively, CH$_2$COO); 5.29 (s, 2H, PhC$\underline{H}_2$); 7.40–7.51 (m, 5H, P$\underline{h}$CH$_2$); 7.63 and 7.68 (s, mi and s, ma, respectively, 1H, H-6). $^{13}$C-NMR (DMSO-d$_6$/TMS): δ=28.2 (BOC); 30.2 and 30.5 (ma and mi, respectively, C$\underline{H}_2$CON); 37.9 and 38.3 (mi and ma, respectively, NC$\underline{H}_2$); 47.5 and 47.9 (ma and mi, respectively, CH$_2$N); 50.2 (C$\underline{H}_2$COO); 67.0 (PhC$\underline{H}_2$); 128.0–128.5 (m, P$\underline{h}$CH$_2$); 135.8 (P$\underline{h}$CH$_2$); 150.5 (Z—CO); 155.7 (C-6); 169.9 and 170.3 (ma and mi, respectively, CON); 170.8 and 171.2 (ma and mi, respectively, COO) MS (FAB+) m/z (%): 504 (16, M+H); 448 (3.5, M-t-Bu+H); 404 (23, M-BOC+H)

EXAMPLE 33

Figure 2:
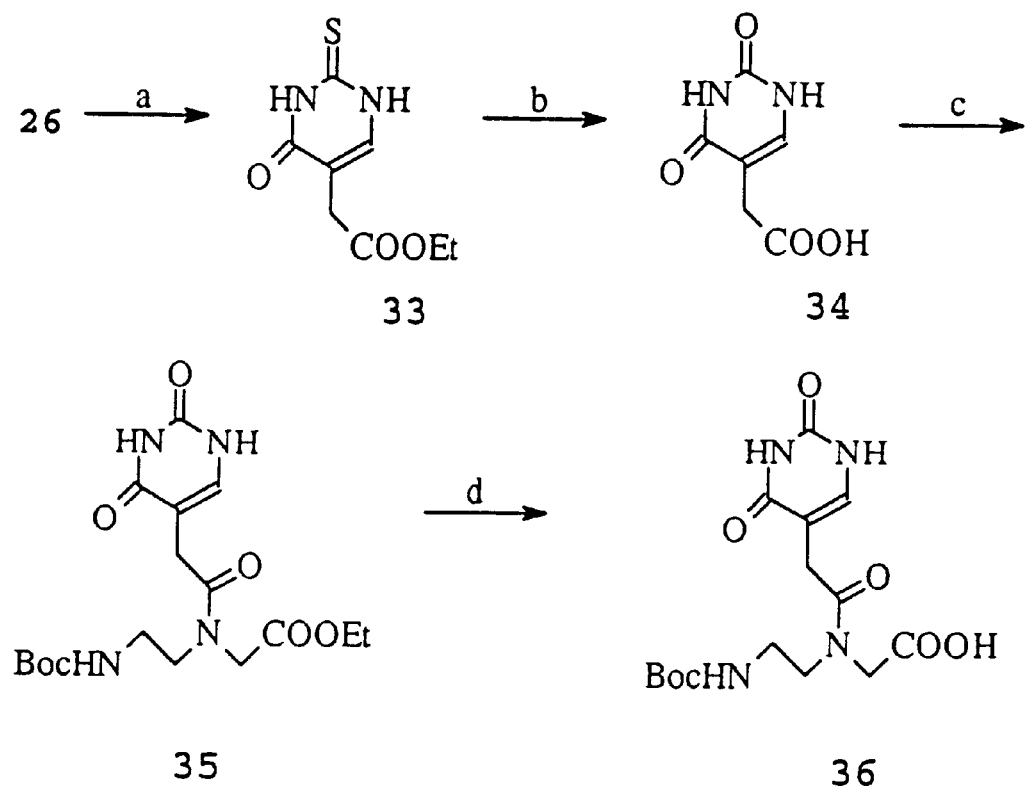
FIG. 2 shows a synthetic scheme according to the invention and discussed in Example 33.

Ethyl (2-Thiouracil-5-yl)acetate, FIG. 2 (33)

All operations were carried out in dry equipment under an atmosphere of nitrogen. Sodium (4.36 g, 190 mmol) was dissolved in abs. ethanol (440 ml). Thiourea (14.4 g, 190 mmol) and methyl α-formylsuccinate (26, 30.0 g, 172 mmol) were added. The reaction mixture was refluxed for 6 hours and, subsequently, evaporated to dryness under reduced pressure. Cold 15% aqueous acetic acid (300 ml) was added to the residue. The mixture was stirred at 0° C. overnight and filtered. The precipitate was washed once with water and dried to yield 12.29 g (37%) of the title compound as a white solid. $^1$H-NMR (DMSO-d$_6$/TMS): δ=1.25 (t, 3H, J=7 Hz, CH$_3$); 3.35 (s, 2H, CH$_2$COO); 4.13 (q, 2H, J=7 Hz, OCH$_2$); 7.52 (s, 1H, H-6); 12.35 (br, 2H, exchangeable protons). $^{13}$C-NMR (DMSO-d$_6$/TMS): δ=14.1 (CH$_3$); 31.6 (C$\underline{H}_2$COO); 60.3 (OCH$_2$); 111.7 (C-5); 140 9 (C-6), 161.2 (C-4); 170.1 (C-2); 175.5 (COO). MS(FAB+) m/z (%): 215 (57, M+H). Calcd. for C$_8$H$_{10}$N$_2$O$_3$S: C, 44.85; H, 4.70; N, 13.08; C/N, 3.43. Found: C, 42.95; H, 4.58; N, 12.89; C/N, 3.33.

EXAMPLE 34

Uracil-5-ylacetic Acid (34)

Ethyl (2-thiouracil-5-yl)acetate (33, 7.8 g, 36 mmol) was mixed with chloroacetic acid (1.9 g, 20 mmol) and water (47 ml) and refluxed for 2 hours. Concentrated hydrochloric acid (22 ml) was added and the reaction mixture was refluxed overnight. The reaction mixture was filtered and the precipitate was washed once with water and dried. The procedure was repeated with the precipitate in place of 8 yielding 4.19 g (68%) of the title compound as a white solid. $^1$H-NMR (DMSO-d$_6$/TMS): 2=3.13 (s, 2H, CH$_2$COO); 7.35 (d, 1H, J=6.5 Hz, H-6); 10.74 (m, 1H, H-1); 11.09 (s, 1H, H-3); 12.20 (br, 1H, COOH). $^{13}$C-NMR (DMSO-d$_6$/TMS): δ=31.3 (C$\underline{H}_2$COO); 106.6 (C-5); 139.7 (C-6); 151.2 (C-2); 164.0 (C-4); 171.9 (COOH).

EXAMPLE 35

Ethyl N-(2-BOC-aminoethyl)-N-(uracil-5-ylacetyl)glycinate (35)

Uracil-5-ylacetic acid (34, 1.0 g, 5.9 mmol) was transferred to a round bottomed flask equipped with a septum through which a flow of nitrogen was applied. Dry DMF (10 ml) and N-methylmorpholine (1.9 ml, 17.6 mmol) were transferred to the flask and the mixture was cooled to 0° C. Ethyl N-(2-BOC-aminoethyl)glycinate (1.6 g, 6.5 mmol) and O-(3,4-dihydro-4-oxo-1,2,3-benzotriazin-3-yl)-N,N,N',N'-tetramethyl uronium tetrafluoroborate (TDBTU, 2.5 g, 7.0 mmol) were added to the mixture. The reaction mixture was stirred for 3 hours at 0° C. and was then poured into ethyl acetate (300 ml). The resultant suspension was washed with saturated aqueous potassium hydrogen sulfate (2×50 ml), saturated aqueous sodium bicarbonate (2×50 ml) and with brine (1×50 ml). The organic phase was dried over magnesium sulfate, filtered and evaporated under reduced pressure. The residue was stirred overnight in dichloromethane (10 ml) and diethyl ether (40 ml). The resultant precipitate was isolated by filtration, washed once with diethyl ether and dried to give 1.13 g (48%) of the title compound as white crystals.

Due to hindered rotation around the amide bond several of the NMR signals are comprised of a major (ma) and minor (mi) component. $^1$H-NMR (DMSO-d$_6$/TMS): δ=1.27 (m, 3H, CH$_3$); 1.45 (s, 9H, BOC); 3.10–3.49 (m, CH$_2$CON, NCH$_2$, CH$_2$N and water); 4.07 (ma), 4.37 (mi) (s, 2H, CH$_2$COO); 4.20 (m, 2H, OCH$_2$); 6.75 (mi), 6.95 (ma) (br, 1H, BOC-N$\underline{H}$); 7.31 (s, 1H, H-6); 10.80 (br, 1H, H-1); 11.15 (br, 1H, H-3). MS(FAB+) m/z (%): 399 (29, M+H); 299 (100, M-BOC+H). Calcd. for C$_{11}$H$_{26}$N$_4$O$_7$: C, 51.25; H, 6.58; N, 14.06; C/N, 3.65. Found: C, 50.62; H, 6.51; N, 13.60; C/N, 3.72.

EXAMPLE 36

N-(2-BOC-Aminoethyl)-N-(uracil-5-ylacetyl)glycine (36)

Ethyl N-(2-BOC-aminoethyl)-N-(uracil-5-ylacetyl)glycinate (35, 1.00 g, 2.5 mmol) was dissolved in 1 M aqueous sodium hydroxide (50 ml) and the mixture was stirred for 15 min at room temperature. The reaction mixture was cooled to 0° C. and the pH was adjusted to 1.5 by the addition of 2 M hydrochloric acid. After 30 min the aqueous solution was extracted with n-butanol (4×80 ml). The n-butanol of the combined organic phases was evaporated under reduced pressure. Residual n-butanol was removed azeotropically with water (5×50 ml). The resultant aqueous solution was freeze-dried to yield 0.93 g (100%) of the title compound as a white solid. Due to hindered rotation around the amide bond several of the NMR signals are comprised of a major (ma) and minor (mi) component. $^1$H-NMR (DMSO-d$_6$/TMS): δ=1.44 (s, 9H, BOC); 3.07–3.48 (m, CH$_2$CON, NCH$_2$, CH$_2$N and water); 4.00 (ma), 4.26 (mi) (s, 2H, CH$_2$COO); 6.75 (mi), 6.94 (ma) (br, 1H, BOC-N$\underline{H}$); 7.28 (mi), 7.32 (ma) (d, 1H, J=5.5 Hz, H-6); 10.87 (br, 1H, H-1); 11.12 (br, 1H, H-3). MS (FAB+) m/z (%): 371 (26, M+H). Calcd. for C$_{15}$H$_{22}$N$_4$O$_7$: C, 48.65; H, 5.99; N, 15.13; C/N, 3.22. Found: C, 35.13; H, 4.66; N, 10.48; C/N, 3.35.

EXAMPLE 37

Figure 3:
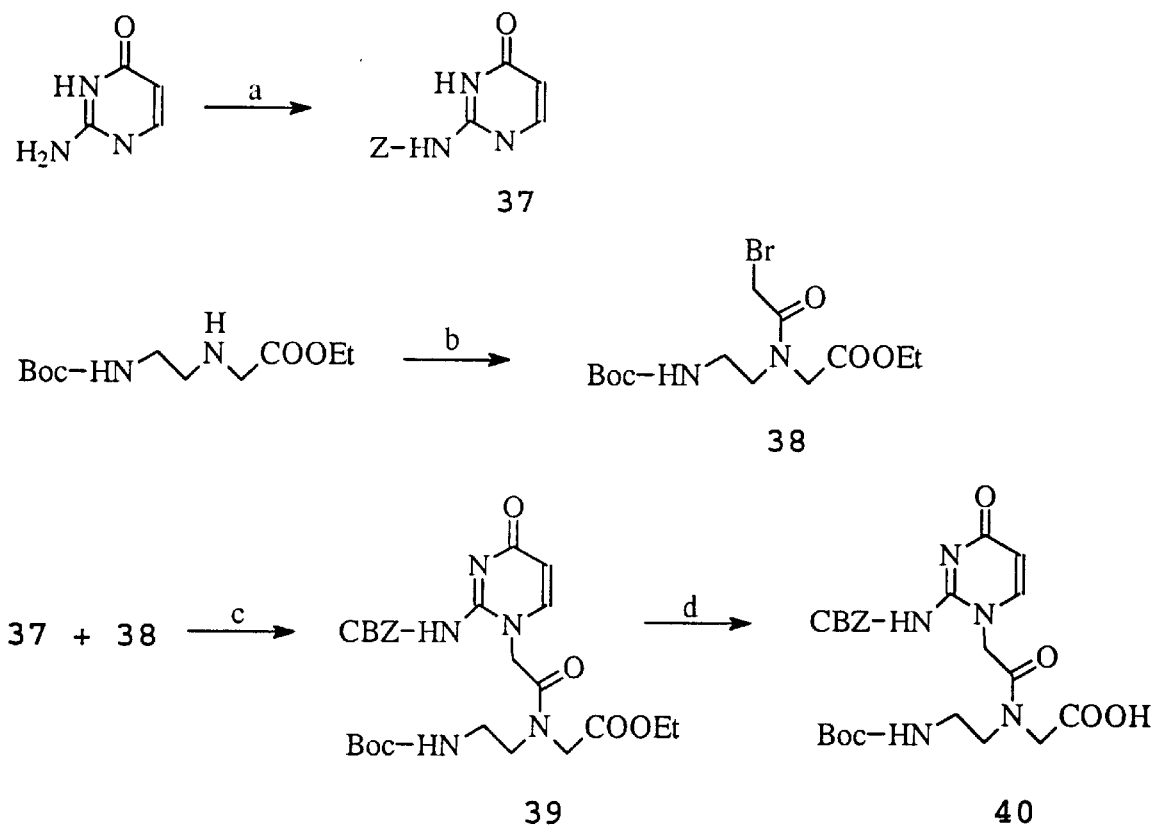
FIG. 3 shows a synthetic scheme according to the invention and discussed in Example 37.

N-2-(Benzyloxycarbonyl)isocytosine, FIG. 3 (37)

Isocytosin (5.0 g, 45 mmol) was dissolved in dry DMF (50 ml) by heating. The solution was cooled to 0° C. and N-benzyloxycarbonyl-N'-methylimidazolium triflate (33 g, 90 mmol) was added slowly. The reaction mixture was stirred under nitrogen at 0° C. for 30 min and then overnight at room temperature. Dichloromethane (400 ml) was added and the organic phase was washed with half-saturated aqueous sodium bicarbonate (2×200 ml), half-saturated aqueous potassium hydrogen sulfate (2×200 ml) and with brine (1×10 ml), dried (MgSO$_4$), filtered and evaporated under reduced pressure. The residue was recrystallized from methanol yielding 7.52 g (68%) of the title compound as white crystals. $^1$H-NMR (DMSO-d$_6$/TMS): δ=5.28 (s, 2H, PhC<u>H</u>$_2$); 6.00 (d, 1H, J=7.0 Hz, H-5); 7.43–7.51 (m, 5H, <u>Ph</u>CH$_2$); 7.77 (d, 1H, J=7.0 Hz, H-6); 11.57 (s, 2H, exchangeable protons). $^{13}$C-NMR (DMSO-d$_6$/TMS): δ=67.0 (Ph<u>C</u>H$_2$); 107.8 (C-5); 128.0–128.5 (m, <u>Ph</u>CH$_2$); 135.8 (<u>Ph</u>CH$_2$); 151.9 (Z—CO). MS (FAB+) m/z (%): 246 (15, M+H).

EXAMPLE 38

Ethyl N-(2-BOC-aminoethyl)-N-(bromoacetyl) glycinate (38)

N'-Boc-aminoethylglycine ethyl ester (8, 5.95 g, 24.2 mmol) was dissolved in dichloromethane (15 ml) and cooled to 0° C. 3,4-Dihydro-3-hydroxy-4-oxo-1,2,3-benzotriazine (DhbtOH, 4.34 g, 26.6 mmol), dicyclohexylcarbodiimide (DCC, 5.98 g, 29.0 mmol) in dichloromethane (15 ml) and bromoacetic acid (3.69 g, 26.6 mmol) in dichloromethane (30 ml) were added. The reaction mixture was stirred at 0° C. for 100 min and then at room temperature for 100 min. It was then filtered and the precipitate was washed with dichloromethane (3×30 ml). The collected filtrate and washings were washed with saturated aqueous sodium bicarbonate (3×120 ml), saturated aqueous potassium hydrogen sulfate (2×120 ml) and with brine (2×120 ml). The organic phase was dried (Na$_2$SO$_4$), filtered and evaporated under reduced pressure. The residue was filtered through silica (30 g, EtOAc/petroleum ether 25:75, v/v until the fastest moving spots on TLC had been removed and then 50:50, v/v to collect the product). The collected fractions were evaporated under reduced pressure to yield 8.29 g (93%) of the title compound as a yellow oil. This oil was used in the next step without further purification. Due to hindered rotation around the amide bond several of the NMR signals are comprised of a major (ma) and minor (mi) component. $^1$H-NMR (CDCl$_3$/TMS): δ=1.24–1.33 (m, 3H, CH$_2$<u>CH</u>$_3$); 1.43 and 1.44 (s, mi and s, ma, respectively, 9H, BOC); 3.28–3.32 (m, 2H, NCH$_2$); 3.54–3.56 (m, 2H, CH$_2$N); 3.79 and 3.93 (s, mi and s, ma, respectively, CH$_2$CON); 4.02 and 4.19–4.26 (s, ma, CH$_2$COO and m, s, mi, <u>CH</u>$_2$CH$_3$, CH$_2$COO, respectively, 4H). $^{13}$C-NMR (CDCl$_3$/TMS): δ=13.8 (CH$_2$<u>CH</u>$_3$); 28.1 (BOC); 38.2 and 38.5 (mi and ma, respectively, NCH$_2$); 48.0 and 48.9 (mi and ma, respectively, CH$_2$N); 50.1 and 50.8 (ma and mi, respectively, <u>CH</u>$_2$COO); 61.4 (<u>CH</u>$_2$CON); 61.8 (<u>CH</u>$_2$CH$_3$). MS (FAB+) m/z (%): 369 (10, M+2+H); 367 (12, M+H); 313 (24, M-t-Bu+2+H); 311 (27, M-t-Bu+H); 269 (67, M-BOC+2+H); 267 (75, M-BOC+H)

EXAMPLE 39

Ethyl N-(2-BOC-aminoethyl)-N-(N-2-(benzyloxycarbonyl)isocytosin-1-yl-acetyl)glycinate (39)

N-2(Benzyloxycarbonyl)isocytosin (37, 2.00 g, 8.2 mmol) was dissolved in dry DMF (15 ml) and potassium carbonate (1.69 g, 12.3 mmol) was added. The mixture was heated to 75° C. for 30 min and then cooled to room temperature. Ethyl N-(2-BOC-aminoethyl)-N-(bromoacetyl)glycinate (38, 3.00 g, 8.2 mmol) in dry DMF (10 ml) was added and the reaction mixture was stirred overnight under nitrogen at room temperature. Water (150 ml) was added to the reaction mixture which was then extracted with dichloromethane (150 and 100 ml). The organic phase was washed with saturated aqueous potassium hydrogen sulfate (3×100 ml) and with brine (2×100 ml), dried (Na$_2$SO$_4$), filtered and evaporated under reduced pressure. The residue was chromatographed on silica (180 ml, EtOAc/n-hexane 1:1 v/v and then EtOAc) to yield 1.95 g (45%) of the title compound as a white glassy foam. Due to hindered rotation around the amide bond several of the NMR signals are comprised of a major (ma) and minor (mi) component. $^1$H-NMR (CDCl$_3$/TMS): δ=1.22–1.29 (m, 3H, CH$_2$<u>CH</u>$_3$); 1.39 and 1.40 (s, ma and s, mi, respectively, 9H, BOC); 3.15–3.25 and 3.35–3.36 (m, mi and m, ma, respectively, 2H, NCH$_2$); 3.50–3.53 (m, 2H, CH$_2$N); 4.02 and 4.27 (s, ma and s, mi, respectively, 2H, CH$_2$COO); 4.09–4.23 (m, 2H, <u>CH</u>$_2$CH$_3$); 4.48 and 4.71 (s, mi and s, ma, respectively, 2H, CH$_2$CON); 5.12 (s, 2H, Ph<u>CH</u>$_2$); 5.80 (d, J=8 Hz, 1H, H-5); 7.19 (d, J=8 Hz, 1H, H-6); 7.25–7.38 (m, 5H, <u>Ph</u>CH$_2$). $^{13}$C-NMR (CDCl$_3$/TMS): δ=13.7 (CH$_2$<u>CH</u>$_3$); 28.0 (BOC); 38.4 (NCH$_2$); 48.4 and 48.9 (mi and ma, respectively, CH$_2$N); 49.1 and 49.4 (ma and mi, respectively, <u>CH</u>$_2$CON); 50.5 (<u>CH</u>$_2$COO); 61.3 and 61.8 (ma and mi, respectively, <u>CH</u>$_2$CH$_3$); 67.1 (<u>Ph</u>CH$_3$); 104.0 (C-5); 127.7–128.1 (m, <u>Ph</u>CH$_2$); 135.8 (<u>Ph</u>CH$_2$); 144.9 (C-6); 153.9 (Z-CO); 159.4 (C-2); 161.9 (C-4); 166.4 (CON); 168.9 (COO). MS (FAB+) m/z (%): 532 (92, M+H); 476 (8, M-t-Bu+H) Calcd. for C$_{25}$H$_{33}$N$_5$O$_8$: C, 56.49; H, 6.26; N, 13.17; C/N, 4.29. Found: C, 55.76; H, 6.54; N, 12.64; C/N, 4.41.

EXAMPLE 40

N-(2-BOC-Aminoethyl)-N-(N-2(benzyloxycarbonyl)isocytosin-1-yl-acetyl)glycine (40)

Ethyl N-(2-BOC-aminoethyl)-N-(N$^2$-(benzyloxycarbonyl)isocytosin-1-ylacetyl)glycinate (39, 1.34 g, 2.5 mmol) was dissolved in THF (40 ml) at 0° C. 1M aqueous lithium hydroxide (7.5 ml, 7.5 mmol) was added and the reaction mixture was stirred for 75 min at 0° C. Water (50 ml) was added and the pH was adjusted to 3 with concentrated hydrochloric acid. The aqueous phase was extracted with EtOAc (2×70 ml). The extracts were collected, dried (Na$_2$SO$_4$), filtered and evaporated under reduced pressure. The residue was dried in a desiccator over sicapent for 65 hours yielding 1.26 g (100%) of product as a white glassy foam.

Due to hindered rotation around the amide bond several of the NMR signals are comprised of a major (ma) and minor (mi) component. $^1$H-NMR (DMSO-d$_6$/TMS): δ=1.44 (s, 9H, BOC); 3.29–3.51 (m, 4H, NCH$_2$ and CH$_2$N); 4.07 and 4.31 (s, ma and s, mi, respectively, 2H, CH$_2$COO); 4.82 and 5.01 (s, mi and s, ma, respectively, 2H, CH$_2$CON); 5.19 (s, 2H, Ph<u>CH</u>$_2$); 5.99–6.01 (m, 1H, H-5); 7.73 and 7.76 (d, mi, J=8 Hz and d, ma, J=8 Hz, respectively, $^1$H, H-6); 7.39–7.45 (m, 5H, <u>Ph</u>CH$_2$). $^{13}$C-NMR (DMSO-d$_6$/TMS): δ=28.2 (BOC); 37.6 and 38.2 (mi and ma, respectively, NCH$_2$); 47.0 and 47.9 (mi and ma, respectively, CH$_2$N); 49.2 (<u>CH</u>$_2$CON); 49.4 and 49.6 (ma and mi, respectively, <u>CH</u>$_2$COO); 66.8 and 66.9 (ma and mi, respectively, Ph<u>CH</u>$_2$); 103.2 (C-5); 127.8–128.3 (m, <u>Ph</u>CH$_2$): 136.5 (<u>Ph</u>CH$_2$); 147.4 (C-6); 154.1 (Z—CO); 155.7 (BOC-CO); 159.5 (C-2); 162.2 (C-4); 166.5 and 166.9 (ma and mi, respectively, CON); 170.3 and 170.7 (ma and mi, respectively, COO). MS (FAB+) m/z (%): 504 (21, M+H); 448 (6, M-t-Bu+H); 404 (11, M-BOC+H); 91 (100, PhCH$_2$).

EXAMPLE 41

Figure 4:
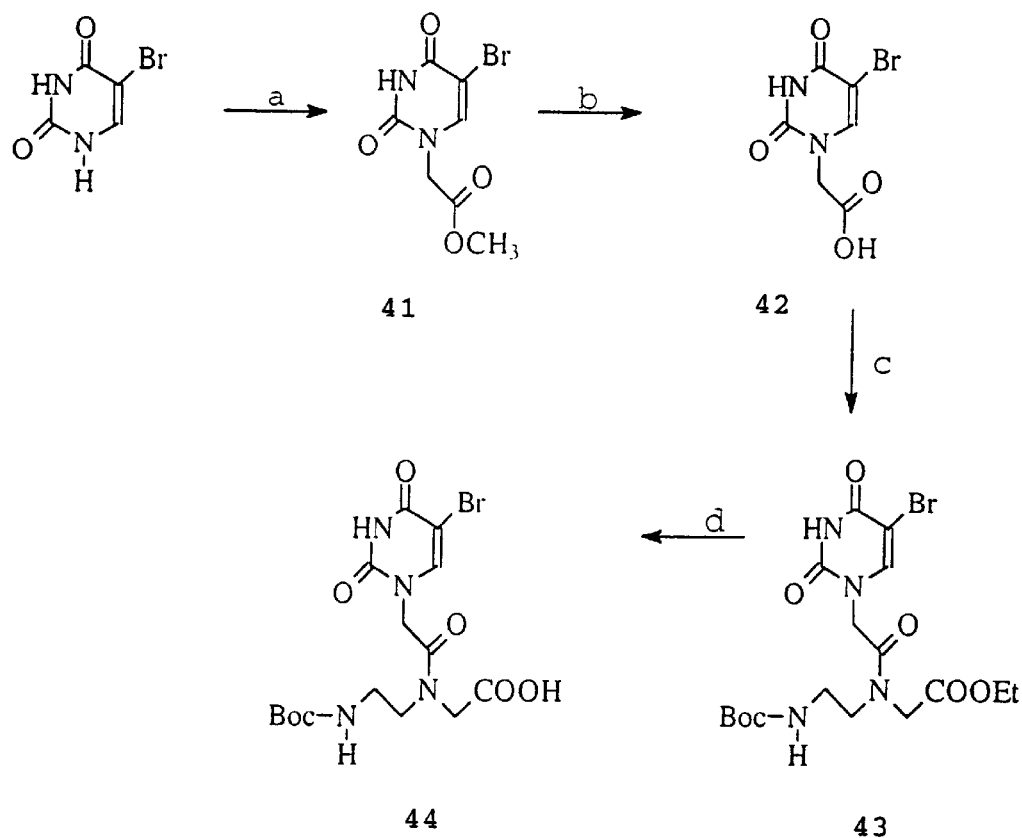
FIG. 4 shows a synthetic scheme according to the invention and discussed in Example 41.

5-Bromouracil-N-1-methyl Acetate, FIG. 4 (41)

5-Bromouracil (5.00 g; 26.2 mmol) and potassium carbonate (7.23 g; 52.3 mmol) were suspended in DMF (75 ml).

Methyl bromoacetate (2.48 ml; 26.1 mmol) was added over a period of 5 min. The suspension was stirred for 2 hours at room temperature, and then filtered. The solid residue was washed twice with DMF, and the combined filtrates were evaporated to dryness, in vacuo. The residue was an oil containing the title compound, DMF and some unidentified impurities. It is not necessary to purify the title compound before hydrolysis. $^1$H-NMR (DMSO-d$_6$, 250 MHz); 8.55 (impurity); 8.27 (CBr=CHN); 8.02 (impurity); 4.76 (impurity); 4.70 (impurity); 4.62 (NCH$_2$COOCH$_3$); 3.78 (COOCH$_3$); 2.96 (DMF); 2.80 (DMF). $^{13}$C-NMR (DMSO-d$_6$, 250 MHz); 168.8 (COOCH$_3$); 172.5 (CH=CBrCON); 161.6 (DMF); 151.9 (NCON); 145.0 (CO—CBr=CHN); 95.6 (COCBr=CHN); 52.6 (impurity); 52.5 (OCH$_3$); 49.7 (impurity); 48.8 (NCH$_2$COOMe); 43.0 (impurity); 36.0 (DMF). UV (Methanol; $_{max}$nm); 226; 278. IR (KBr; cm$^{-1}$—; 3158s (—NH); 1743vs (—C=O, COOMe); 1701vs (—C=O, CONH); 1438vs (∂ CH, CH$_3$O); 1223vs (—C—O, COOMe); 864 m (∂ CH, Br=C—H). FAB-MS m/z (assignment): 265/263 (M+H).

EXAMPLE 42

(5-Bromouracil)acetic Acid (42)

Water (30 ml) was added to the oil of the crude product from Example 41 and the mixture was dissolved by adding sodium hydroxide (2M, 60 ml). After stirring at 0° C. for 10 min, hydrochloric acid (4M, 45 ml) was added to pH=2 and the title compound precipitated. After 50 min, the solid residue was isolated by filtration, washed once with cold water, and then dried in vacuo over sicapent. Yield: 2.46 g (38%). Mp, 250°–251° C. Anal. for C$_6$H$_5$BrN$_2$O$_4$. Found (calc.): C: 28.78 (28.94); H: 2.00 (2.02); Br: 32.18 (32.09); N: 11.29 (11.25). $^1$H-NMR (DMSO-d$_6$, 250 MHz): 12,55 (1H.s, COOH); 11.97 (1H, s, NH); 8.30 (1H, s, C=C—H); 4.49 (2H, s, NCH$_2$COOH). $^{13}$C-NMR (DMSO-d$_6$, 250 MHz); 169.4 (COCH); 159.8 (NHCOCBr=CH); 150.04 (N CON); 145.8 (COCBr=CHN); 94.6 (COCBr=CHN); 48.8 (NCH$_2$COOH). UV (Methanol; $^{max}$nm); 226; 278. IR (KBr; cm$^{-1}$); 3187s (—NH); 1708vs (—C=O,COOH); 1687vs; 1654VS (—C=O, CONH); 1192s (—C—O, COOH); 842 m (∂ CH, Br—C=C—H). FAB-MS m/z (assignment, intensity); 251/249 (M+H, 5).

EXAMPLE 43

N-(Boc-aminoethyl)-N-(5-bromouracil-N-1-methylenecarbonoyl)-glycine Ethyl Ester (43)

N'-Boc-aminoethylglycineethyl ester (8, 1.80 g; 7.30 mmol) was dissolved in DMF (10 ml). Dhbt-OH (1.31 g; 8.03 mmol) was added, whereby a precipitate was formed. DMF (2×10 ml) was added until the precipitate was dissolved. (5-Bromouracil)acetic acid (42, 2.00 g; 8.03 mmol) was added slowly to avoid precipitation. Methylene chloride (30 ml) was added, and the mixture was cooled to 0° C. and then filtered. The precipitate, DCU, was washed twice with methylene chloride. To the combined filtrate was added methylene chloride (100 ml). The mixture was washed with half saturated NaHCO$_3$-solution (3×100 ml, H$_2$O:saturated NaHCO$_3$-solution 1:1 v/v), then with dilute KHSO$_4$-solution (2×100 ml, H$_2$O:saturated KHSO$_4$-solution 4:1 v/v), and finally with saturated NaCl-solution (1×100 ml). The organic phase was dried over magnesium sulphate, filtered, and evaporated to dryness in vacuo (about 15 mmHg and then about 1 mmHg). The residue was suspended in methylene chloride (35 ml), stirred for 45 min at room temperature, and filtered (the precipitate was DCU). Petroleum ether (2 volumes) was added dropwise to the filtrate at 0° C., whereby an oil precipitated. The liquor was decanted and the remaining oil dissolved in methylene chloride (20–50 ml). Precipitated was effected by the addition of petroleum ether (2 volumes). This procedure was repeated 5 times until an impurity was removed. The impurity can be seen at TLC with 10% MeOH/CH$_2$Cl$_2$ as the developing solvent. The resulting oil was dissolved in methylene chloride (25 ml) and evaporated to dryness in vacuo, which caused solidification of the title compound. Yield: 2.03 g ((58%). Mp. 87°–90° C. Anal. for C$_{17}$H$_{25}$BrN$_4$O$_7$. Found (calc.): C: 42.33 (42.78); H: 5.15 (5.28); Br: 17.20 (16.74); N: 1.69 (11.74). $^1$H-NMR (DMSO-d$_6$, 250 MHz, J in Hz): 1.93 & 11.92 (1H, s, C=ONHC=O); 8.09 & 8.07 (1H, s, C=C—H); 7.00 & 6.80 (1H, t, b, BocNH); 4.80 & 4.62 (2H, s, NCH$_2$CON); 4.35 & 4.24 (2H, s, NCH$_2$COOEt); 4.27–4.15 (2H, m's, COOCH$_2$CH$_3$O); 3.47–3.43 (2H, m's, BocNHCH$_2$CH$_2$N); 3.28–3.25 & 3.12–3.09 (2H, m's, Boc-NHCH$_2$CH—$_2$N): 1.46 & 1.45 (9H, s, $^t$Bu); 1.26 & 1.32 (3H, t, J=7.1, COOCH$_2$CH$_3$). $^{13}$C-NMR (DMSO-d$_6$, 250 MHz); 169.3 & 169.0 ($^t$BuOC=O); 167.4 & 167.1 (COOEt); 159.8 (C=C—CON); 155.9 (NCH$_2$CON); 150.4 (NCON); 145.9 (COCBr—CHN); 94.5 (COCBr=CHN); 78.2 (Me$_3$C); 61.3 & 60.7 (COCH$_2$CH$_3$); 49.1 & 48.0 (N CH$_2$COOH); 48.0 & 47.0 (NCH$_2$CON); 38.6 (BocNHCH$_2$ CH$_2$N); 38.2 (BocNHCH$_2$CH$_2$N); 26.3 (C(CH$_3$)$_3$); 14.1 (COCH$_2$CH$_3$). UV (Methanol; $_{max}$NM): 226; 280. IR (KBr, CM$^{-1}$): 3200ms, broad (—NH); 168vs, vbroad (—C=O, COOH, CONH); 1250s (—C—O, COOEt); 1170s (—C—O, COO$^t$Bu); 859m (∂ CH, Br—C=C—H). FAB-MS m/z (assignment, relative intensity): 479/477 (M+H, 5); 423/421 (M+2H−$^t$Bu, 8); 379/377 (M+2H −Boc, 100); 233/231 (M—backbone, 20).

EXAMPLE 44

N-(Boc-aminoethyl)-N-(5-bromouracil-N-1-methylenecarbonoyl)-glycine (44)

N-(Boc-aminoethyl)-N-(5-bromouracil-N-1-methylenecarbonoyl)ethyl ester (43, 1.96 g; 4.11 mmol) was dissolved in methanol (30 ml) by heating, and then cooled to 0° C. Sodium hydroxide (2M, 30 ml) was added, and the mixture was stirred for 30 min. HCl (1M, 70 ml) was added to pH=2.0. The water phase was extracted with ethyl acetate (3×65 ml+7×40 ml). The combined ethyl acetate extractions were washed with saturated NaCl-solution (500 ml). The ethyl acetate phase was dried over magnesium sulphate, filtered and evaporated to dryness in vacuo. Yield: 1.77 g (96%). Mp. 92°–97° C. Anal. for C$_{15}$H$_{21}$BrN$_4$O$_8$. Found (calc.): C: 40.79 (40.10); H: 5.15 (4.71); Br: 14.64 (17.70); N: 11.35 (12.47). $^1$H-NMR (DMSO-d$_6$, 250 MHz, J in Hz): 12.83 (1H, s, COOH); 11.93 & 11.91 (1H, s, C=ON HC=O) 8.10 & 8.07 (1H, s, C=C—H); 7.00 & 6.81 (1H, t, b, BocNH); 4.79 & 4.61 (2H, s, NCH$_2$CON); 4.37 & 4.25 (2H, s, NCH$_2$COOH); 3.46–3.39 (2H, m's, BocNHCH$_2$C H$_2$N); 3.26–3.23 & 3.12–3.09 (2H, m's, BocNHCH$_2$CH$_2$N); 1.46 (9H, s, $^t$Bu). $^{13}$C-NMR 9DMSO-d$_6$, 250 MHz); 170.4 ($^t$BuOC=O); 166.9(COOH); 159.7 (C=C—CON); 155.8 (NCH$_2$CON); 150.4 (NCON); 145.9 (COCBr=CHN); 94.4 (COCBr=CHN); 78.1 (Me$_3$C); 49.1 & 48.0 (NCH$_2$COOH); 47.7 & 47.8 (NCH$_2$CON); 38.6 (BocNHC$_2$CH$_2$N); 38.1 (Boc NHCH$_2$CH$_2$N); 28.2 (C(CH$_3$)$_3$). UV (Methanol; $^{max}$nm); 226; 278. IR (KBr,cm$^{-1}$): 3194ms, broad (—NH); 1686vs, vbroad (—C=O COOH, CONH); 1250s (—C—O,COOH); 1170s (—C—O, COO$^t$Bu); 863m (∂ CH, Br—C=C—H). FAB-MS m/z (assignment, relative intensity): 449/451 (M+H, 70); 349/351 (M+2H −Boc, 100); 231/233 (M −backbone, 20).

EXAMPLE 45

Synthesis of PNA Oligomers by Solid Phase, General Procedure

The functionalized resin is measured out to typically provide 0.1–1.0 millimoles of functionality, (functionalities attached to resins are commercially available through various sources e.g. Peptides International, Kentucky). This weight of resin is suspended in a 1:1 (v:v) dichloromethane:dimethylformamide solution (5 mL/1 gm of resin) and allowed to swell for a period of time if desired. The solvent is then removed by filtration and the resin resuspended in trifluoroacetic acid (1 mL/1 gm of resin) and shaken for 2 minutes. The trifluoroacetic acid is removed by filtration and this step is repeated once. The resin is washed three times with a solution of 1:1 (v:v) dichloromethane:dimethylformamide. The resulting resin is resuspended in pyridine solution (5 mL/1 gm of resin) and vacuum filtered to remove the pyridine. This step is repeated once. This is followed by resuspension followed by filtration (designated "washing") using 1:1 (v:v) dichloromethane:dimethylformamide solution (5 mL/1 gm of resin) this washing step is repeated twice. The resin is suspended in 1:1 (v:v) pyridine:dimethylformamide and to this suspension is added the desired PNA monomer (2–10 molar equivalents), TBTU (1.9–9.9 molar equivalents), and di-isopropylethylamine (5–20 molar equivalents) such that the final concentration of PNA monomer is 0.2M. The suspension is shaken for 15–60 minutes and the spent coupling solution is removed by filtration. The resin is washed with pyridine three times, and any unreacted amines are capped using Rapoport's Reagent, 5 equivalents in DMF for 5 minutes. The resin is then washed three times with pyridine followed by three washes with a solution of 1:1 (v:v) dichloromethane: dimethylformamide (5 mL/1 gm of resin). At this point, the resin is ready for the next coupling reaction and this procedure is repeated until the desired PNA is assembled on the resin.

Specific Examples of Amino Ethyl Glycine (aeg-) PNAs and aeg-PNA Derivatives Prepared by this General Method

| Resin Employed | aeg-PNA/aeg-PNA Derivative Prepared |
|---|---|
| Merrifield | $H_2N$-GCAT-COOH (SEQ ID NO:1) |
| Lys Substituted Merrifield | $H_2N$-GCAT-Lys-COOH (SEQ ID NO:2) |
| MBHA | $H_2N$-GCAT-CONH$_2$ (SEQ ID NO:3) |
| Lys Substituted MBHA | $H_2N$-GCAT-Lys-CONH$_2$ (SEQ ID NO:4) |

EXAMPLE 46

Capping of the PNA

PNA can be capped by a non-PNA moiety on the N terminus by following the procedures described in Example 45 and substituting a desired carboxylic acid-based capping reagent for the PNA monomer in the final coupling step.

Specific Examples of (aeg) PNAs and aeg PNA Derivatives Prepared by this General Method

| Resin Employed | aeg-PNA/aeg-PNA Derivative Prepared |
|---|---|
| Capping Reagent = Acetyl | |
| Merrifield | $CH_3$CONH-GCAT-COOH (SEQ ID NO:5) |
| | $H_2N$-GCAT-COOH (SEQ ID NO;6) |
| Lys Substituted Merrifield | $H_2N$-GCAT-Lys-COOH (SEQ ID NO:7) |
| Merrifield | $H_2N$-GCAT-CONH$_2$ (SEQ ID NO:8) |
| Lys Substituted MBHA | $H_2N$-GCAT-Lys-CONH$_2$ (SEQ ID NO:9) |
| Lys Substituted Merrifield | $CH_3$CONH-GCAT-Lys-COOH (SEQ ID NO:10) |
| | $H_2$NGCAT-COOH (SEQ ID NO:11) |
| Lys Substituted Merrifield | $H_2N$-GCAT-Lys-COOH (SEQ ID NO:12) |
| Merrifield | $H_2N$-GCAT-CONH$_2$ (SEQ ID NO:13) |
| MBHA | $H_2N$-GCAT-CONH$_2$ (SEQ ID NO:14) |
| Lys Substituted MBHA | $H_2N$-GCAT-Lys-CONH$_2$ (SEQ ID NO:15) |
| MBHA | $CH_3$CONH-GCAT-CONH$_2$ (SEQ ID NO:16) |
| | $H_2N$-GCAT-CONH$_2$ (SEQ ID NO:17) |
| Lys Substituted MBHA | $CH_3$CONH-GCAT-Lys-CONH$_2$ (SEQ ID (NO:18) |

| | |
|---|---|
| Merrifield | BocGly-GCAT-COOH (SEQ ID NO:19) |
| Lys Substituted Merrifield | BocGly-GCAT-Lys-COOH (SEQ ID NO:20) |
| MBHA | BocGly-GCAT-CONH$_2$ (SEQ ID NO:21) |
| Lys Substituted MBHA | BocGly-GCAT-Lys-CONH$_2$ (SEQ ID NO:22) |
| Capping Reagent = 1. Glycine; 2. Cholic Acid (Chol) | |
| Merrifield | Chol-GlyGCAT-COOH (SEQ ID NO:23) |
| Lys Substituted Merrifield | Chol-GlyGCAT-Lys-COOH (SEQ ID NO:24) |
| MBHA | Chol-GlyGCAT-CONH$_2$ (SEQ ID NO:25) |
| Lys Substituted MBHA | Chol-GlyGCAT-Lys-CONH$_2$ (SEQ ID NO:26) |

EXAMPLE 47

Lys/Aha Linked Bis aeg-PNA Preparation H-Gly-TTC-TCT-CTC-T-Lys-Aha-Lys-Aha-Lys-T-CTC-TCT-CTT-Lys-NH$_2$ (SEQ ID NO:27)

The first ten aeg-PNA monomeric units were coupled by coupling an aeg-T monomeric unit to a lysine-MBHA resin via standard solid phase methods as per the procedures of Example 45, using TBTU activation resulting in a resin-bound PNA monomer containing amino terminal t-butyloxycarbonyl (BOC) protection. In an iterative process the other 9 aeg-PNA monomeric units were coupled. The terminal aeg-PNA contains an amino terminal t-butyloxycarbonyl (BOC) protection group.

The support was washed four times with N,N-dimethylformamide/dichloromethane (1:1) and then treated twice with 5% m-cresol in trifluoroacetic acid (3 mL) with shaking for three minutes each time. The support was washed again with N,N-dimethylformamide/dichloromethane (1:1) and then with pyridine. To a vial was added t-butyloxycarbonyl-N-ε-(2- chlorobenzyloxycarbonyl)-L-lysine (200 mmoles) and O-(benzotriazol- 1-yl)-1,1,3,3-tetramethyluronium tetrafluoroborate (180 mmoles). N,N-Dimethylformamide (1 mL) and pyridine (1 mL) were added to the vial followed by N,N-diisopropylethylamine (400 mmoles) The vial was shaken until all solids were dissolved. After one minute the contents of the vial were added to the peptide synthesis vessel and shaken for 20 minutes. The reaction solution was then drained away and the support washed five times with pyridine. Remaining free amine was capped by addition of a 10% solution of N-benzyloxycarbonyl-N'-methyl-imidazole triflate in N,N-dimethylformamide (1.5 mL). After shaking for five minutes, the capping solution was drained and the support washed five times with pyridine.

The remainder of the linker was prepared by the sequential coupling (as above) of N-t-butyloxycarbonyl-ε-amino-hexanoic acid, t-butyloxycarbonyl-N-ε-(2-chlorobenzyloxycarbonyl)-L-lysine, N-t-butyloxycarbonyl-ε-aminohexanoic acid, and t-butyloxycarbonyl-N-ε-(2-chlorobenzyloxycarbonyl)-L-lysine. The resulting oligomer consisting of a decamer aeg-PNA containing an amino terminal linker with a t-butyloxycarbonyl cap was then extended for the remaining 10 PNA units again via standard solid phase methods. Cleavage off of the support and HPLC purification was as described for standard PNA oligomers. The title compound was determined by electrospray mass spectrometry to have the expected molecular weight of 6012 daltons. The thermal stability of the PNA/DNA triplex formed by this bis-PNA and its target was found to be greater than the PNA/DNA triplex formed by the corresponding single PNA and target (Tm=89° C. for bis vs. 85° C. for single). Mass spectrometry also demonstrated that the bis-PNA formed a 1:1 complex with target while the single PNA formed a 2:1 complex with its target.

EXAMPLE 47a

Lys/Amino Cis-Hexenoic Acid Linked Bis aeg-PNA Preparation H-Gly-TTC-TCT-CTC-T-Lys-Achea-Lys-Achea-Lys-T-CTC-TCT-CTT-Lys-NH$_2$ (Achea=Amino Cis-hexenoic Acid) (SEQ ID NO:28)

The first ten aeg-PNA monomeric units are coupled by coupling an aeg-T monomeric unit to a lysine-MBHA resin via standard solid phase methods as per the procedures of Example 45, using TBTU activation resulting in a resin-bound PNA monomer containing amino terminal t-butyloxycarbonyl (BOC) protection. In an iterative process the other 9 aeg-PNA monomeric units are coupled. The terminal aeg-PNA contains an amino terminal t-butyloxycarbonyl (BOC) protection group.

The support is washed four times with N,N-dimethylformamide/dichloromethane (1:1) and then treated twice with 5% m-cresol in trifluoroacetic acid (3 mL) with shaking for three minutes each time. The support is washed again with N,N-dimethylformamide/dichloromethane (1:1) and then with pyridine. To a vial is added t-butyloxycarbonyl-N-ε-(2-chlorobenzyloxycarbonyl)-L-lysine (200 mmoles) and O-(benzotriazol-1-yl)-1,1,3,3-tetramethyluronium tetrafluoroborate (180 mmoles). N,N-Dimethylformamide (1 mL) and pyridine (1 mL) were added to the vial followed by N,N-diisopropylethylamine (400 mmoles). The vial is shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 mL). After shaking for five minutes, the capping solution is drained and the support washed five times with pyridine.

The remainder of the linker is prepared by the sequential coupling (as above) of N-t-butyloxycarbonyl-ε-amino-hexenoic acid, t-butyloxycarbonyl-N-ε-(2-chlorobenzyloxycarbonyl)-L-lysine, N-t-butyloxycarbonyl-ε-aminohexenoic acid, and t-butyloxycarbonyl-N-ε-(2-chlorobenzyloxycarbonyl)-L-lysine. The resulting oligomer consisting of a decamer aeg-PNA containing an amino terminal linker with a t-butyloxycarbonyl cap is then extended for the remaining 10 PNA units again via standard solid phase methods. Cleavage off of the support and HPLC purification is as described for standard PNA oligomers.

EXAMPLE 47b

Lys/Amino Hexynoic Acid Linked Bis aeg-PNA Preparation H-Gly-TTC-TCT-CTC-T-Lys-Ahya-Lys-Ahya-Lys-T-CTC-TCT-CTT-Lys-NH$_2$ (Ahya= Amino Hexynoic Acid) (SEQ ID NO:29)

The first ten aeg-PNA monomeric units are coupled by coupling an aeg-T monomeric unit to a lysine-MBHA resin via standard solid phase methods as per the procedures of Example 45, using TBTU activation resulting in a resin-bound PNA monomer containing amino terminal t-butyloxycarbonyl (BOC) protection. In an iterative process the other 9 aeg-PNA monomeric units are coupled. The terminal aeg-PNA contains an amino terminal t-butyloxycarbonyl (BOC) protection group.

The support is washed four times with N,N-dimethylformamide/dichloromethane (1:1) and then treated twice with 5% m-cresol in trifluoroacetic acid (3 mL) with shaking for three minutes each time. The support is washed again with N,N-dimethylformamide/dichloromethane (1:1) and then with pyridine. To a vial is added t-butyloxycarbonyl-N-ε-(2-chlorobenzyloxycarbonyl)-L-lysine (200 mmoles) and O-(benzotriazol-1-yl)-1,1,3,3-tetramethyluronium tetrafluoroborate (180 mmoles). N,N-Dimethylformamide (1 mL) and pyridine (1 mL) are added to the vial followed by N,N-diisopropylethylamine (400 mmoles). The vial was shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 mL). After shaking for five minutes, the capping solution is drained and the support washed five times with pyridine.

The remainder of the linker is prepared by the sequential coupling (as above) of N-t-butyloxycarbonyl-ε-amino-hexynoic acid, t-butyloxycarbonyl-N-ε-(2-chlorobenzyloxycarbonyl)-L-lysine, N-t-butyloxycarbonyl-ε-aminohexynoic acid, and t-butyloxycarbonyl-N-ε-(2-chlorobenzyloxycarbonyl)-L-lysine. The resulting oligomer consisting of a decamer aeg-PNA containing an amino terminal linker with a t-butyloxycarbonyl cap is then extended for the remaining 10 PNA units again via standard solid phase methods. Cleavage off of the support and HPLC purification is as described for standard PNA oligomers.

EXAMPLE 47c

Lys/Meta-Amino Benzoic Acid Linked Bis aeg-PNA Preparation H-Gly-TTC-TCT-CTC-T-Lys-MABA-Lys-MABA-Lys-T-CTC-TCT-CTT-Lys-NH$_2$ (SEQ ID NO:30) (MABA=Meta-Amino Benzoic Acid)

The first ten aeg-PNA monomeric units are coupled by coupling an aeg-T monomeric unit to a lysine-MBHA resin via standard solid phase methods as per the procedures of Example 45, using TBTU activation resulting in a resin-bound PNA monomer containing amino terminal t-butyloxycarbonyl (BOC) protection. In an iterative process the other 9 aeg-PNA monomeric units are coupled. The terminal aeg-PNA contains an amino terminal t-butyloxycarbonyl (BOC) protection group.

The support is washed four times with N,N-dimethylformamide/dichloromethane (1:1) and then treated twice with 5% m-cresol in trifluoroacetic acid (3 mL) with shaking for three minutes each time. The support is washed again with N,N-dimethylformamide/dichloromethane (1:1) and then with pyridine. To a vial is added t-butyloxycarbonyl-N-ε-(2-chlorobenzyloxycarbonyl)-L-lysine (200 mmoles) and O-(benzotriazol-1-yl)-1,1,3,3-tetramethyluronium tetrafluoroborate (180 mmoles). N,N-Dimethylformamide (1 mL) and pyridine (1 mL) are added to the vial followed by N,N-diisopropylethylamine (400 mmoles). The vial was shaken until all solids are dissolved. After one minute the contents of the vial are added to the peptide synthesis vessel and shaken for 20 minutes. The reaction solution is then drained away and the support washed five times with pyridine. Remaining free amine is capped by addition of a 10% solution of N-benzyloxycarbonyl-N'-methyl-imidazole triflate in N,N-dimethylformamide (1.5 mL). After shaking for five minutes, the capping solution is drained and the support washed five times with pyridine.

The remainder of the linker is prepared by the sequential coupling (as above) of N-t-butyloxycarbony-meta-aminobenzoic acid, t-butyloxycarbonyl-N-ε-(2-chlorobenzyloxycarbonyl)-L-lysine, N-t-butyloxycarbony-meta-aminobenzoic acid, and t-butyloxycarbonyl-N-ε-(2-chlorobenzyloxycarbonyl)-L-lysine. The resulting oligomer consisting of a decamer aeg-PNA containing an amino terminal linker with a t-butyloxycarbonyl cap is then extended for the remaining 10 PNA units again via standard solid phase methods. Cleavage off of the support and HPLC purification is as described for standard PNA oligomers.

EXAMPLE 48

Lys/Aha Linked Bis aeg-PNA Preparation H-Gly-TCT-TTT-Lys-Aha-Lys-Aha-Lys-TTT-TCT-TTT-Lys-CONH$_2$ (SEQ ID NO:31)

The title Lys/Aha linked aeg-PNA was synthesized as per the procedures of Example 47 except the polystrene polyethylene glycol copolymer resin "Tentagel Resin" was used as the synthetic support.

EXAMPLE 49

Lys/Aha Linked Bis aeg-PNA Preparation H-Gly-TTT-TGT-TTT-Lys-Aha-Lys-Aha-Lys-TTT-TCT-TTT-Lys-CONH$_2$ (SEQ ID NO:32)

The title Lys/Aha linked aeg-PNA was synthesized as per the procedures of Example 47 except the polystrene polyethylene glycol copolymer resin "Tentagel Resin" was used as the synthetic support.

EXAMPLE 50

Lys/Aha Linked Bis aeg-PNA Preparation H-Gly-TTT-TCT-TTT-Lys-Aha-Lys-Aha-Lys-TTT-TCT-TTT-Lys-CONH$_2$ (SEQ ID NO:33)

The title Lys/Aha linked aeg-PNA was synthesized as per the procedures of Example 47 except the polystrene polyethylene glycol copolymer resin "Tentagel Resin" was used as the synthetic support.

EXAMPLE 51

Lys/Aha Linked Bis aeg-PNA Having Pseudoisocytosine(J) H-Gly-TTJ-TJT-JTJ-T-Lys-Aha-Lys-Aha-Lys-T-CTC-TCT-CTT-Lys-NH$_2$ (SEQ ID NO:34)

The title Lys/Aha linked bis aeg-PNA is synthesized as per the procedures of Example 47. Pseudoisocytosine "(J)" monomeric units are synthesized as per the procedures of examples 26 thru 32 and are used in place of cytosine monomeric units to give the title compound.

EXAMPLE 52

Lys/Aha Linked Bis aeg-PNA Having Pseudouracil (ΨU) H-Gly-GΨUA-GAΨU-JAC-ΨU-Lys-Aha-Lys-Aha-Lys-GUA-GAU-CAC-U-Lys-NH$_2$ (SEQ ID NO:35)

The title Lys/Aha linked bis PNA is synthesized as per the procedures of Example 47. Pseudouracil "ΨU" monomeric units are synthesized as per the procedures of examples 33 thru 36 and are used in place of some of the uracil monomeric units to give the title compound.

EXAMPLE 53

Lys/Aha Linked Bis aeg-PNA Having Isocytosine (iC)

H-Gly-TTiC-TiCT-iCTiC-T-Lys-Aha-Lys-Aha-Lys-T-CTC-TCT-CTT-Lys-NH$_2$ (SEQ ID NO:36)

The title Lys/Aha linked bis aeg-PNA is synthesized as per the procedures of Example 47. Aeg-isocytosine "iC" monomeric units are synthesized as per the procedures of Examples 37 thru 40 and are used in place of some of the aeg-cytosine monomeric units to give the title compound.

EXAMPLE 54

Lys/Aha Linked Bis aeg-PNA Having 5-Bromouracil (5BrU) H-Gly-G5BrUA-GA5BrU-JAC-5BrU-Lys-Aha-Lys-Aha-Lys-GUA-GAU-CAC-U-Lys-NH$_2$ (SEQ ID NO:37)

The title Lys/Aha linked bis aeg-PNA is synthesized as per the procedures of Example 47. aeg-5-bromo-uracil monomeric units are synthesized as per the procedures of Examples 41 thru 44 and are used in place of some of the aeg-uracil monomeric units to give the title compound.

EXAMPLE 55 egl Linked Bis aeg-PNA Preparation H-TCT-CTT-T-egl-egl-egl-TTT-CTC-T-Lys-NH$_2$ (SEQ ID NO:38) (egl=—NH—CH$_2$—CH$_2$—O—CH$_2$—CH$_2$—O—CH$_2$—C(=O)—)

The protected bis aeg-PNA was assembled on a Boc-Lys (ClZ) functionalized MBHA resin with a substitution of approximately 0.10 mmol/g. The synthesis was initiated on 200 mg (dry weight) of t-Boc-Lys(ClZ)-MBHA resin, pre-swollen overnight in dichloromethane. The following steps were repeated until the desired sequence was obtained: (1) removal of the N-terminal t-Boc protecting group by treatment with 95:5 TFA/m-Cresol (2×4 min, 1 ml); (2) wash with 1:1 DMF/dichloromethane (3×1 min, 1 ml); (3) wash with pyridine (2×1 min, 1 ml); (4) HBTU (18.0 mg, 0.48 mmol) and monomer (0.5 mmol, t-Boc-$C^ZOH$ (25.1 mg), t-Boc-T-OH (19.2 mg) or t-Boc-egl-OH (13.1 mg)) was taken up in 1:1 DMF/pyridine (in the case of t-Boc-egl-OH neat DMF was used) and added DECA (16 ml, 1 mmol) to a final volume of 0.5 ml and the mixture was allowed to preactivate for 1 minute before addition to the resin where the coupling was allowed to proceed for 20 min at room temperature; (5) a few beads were removed for qualitative Kaiser test (Ninhydrin); (6) Wash with pyridine (2×1 min, 1 ml); (7) acylation with Rappoport's reagent (100 mg, 0.28 mmol) in DMF (1 ml); (8) Wash with 8:2 DMF/pipiridine; (9) wash with pyridine (3×1 min, 1 ml); (10) Wash with 1:1 DMF/dichloromethane (3×1 min, 1 ml).

When the desired sequence was obtained the resin was washed with neat dichloromethane (3×1 min, 1.5 ml) and then dried in a desiccator under vacuum. All qualitative Kaiser-tests were yellow with no coloration of the beads.

The bis aeg-PNA was cleaved from the resin and the permanent protection groups were removed. A solution of 1:8:1 TFA/DMS/m-cresol (50 μL) and a solution of 9:1 TFA/TFMSA (50 μL) were cooled on an icebath and added per 10 mg of dry resin. The reaction was allowed to proceed for 1 hour at room temperature and the resin was drained and washed with neat TFA (1×1 min, 1 ml). A solution of 8:1:1 TFA/TFMSA/m-cresol (100 μL) (cooled on an icebath) was added per 10 mg of dry resin. The reaction was allowed to proceed for 2 hours and the resin was drained and washed with TFA(1×1 min, 1 ml). The two TFA solutions combined and the aeg-PNA was precipitated by addition of dry ether. The precipitate was washed four times with dry ether. Yield: 12.7 mg (Purity >90%, purified by RP-HPLC, μBondapak $C_{18}$). MS(FAB+) m/z: :(found/calcd) 4249/4247

EXAMPLE 55a egl Linked Bis aeg-PNA Preparation H-TTT-TCC-TCT-C-egl-egl-egl-CTC-TCC-TTT-T-Lys-NH$_2$ (SEQ ID NO:39) (egl=—NH—CH$_2$—CH$_2$—O—CH$_2$—CH$_2$—O—CH$_2$—C(=O)—)

The title egl linked bis aeg-PNA was synthesized according to the procedures of Example 55.

EXAMPLE 55b egl Linked Bis aeg-PNA Preparation H-GTA-GAT-CA-egl-egl-egl-TGA-TCT-AC-Lys-NH$_2$ (SEQ ID NO:40) (egl=—NH—CH$_2$—CH$_2$—O—CH$_2$—CH$_2$—O—CH$_2$—C(=O)—)

The title egl linked bis aeg-PNA was synthesized according to the procedures of Example 55.

EXAMPLE 56 egl Linked Bis aeg-PNA Having Pseudoisocytosine (J)

H-TJT-JTT-T-egl-egl-egl-TTT-CTC-T-Lys-NH$_2$ (SEQ ID NO:41) (egl=—NH—CH$_2$—CH$_2$—O—CH$_2$—CH$_2$—O—CH$_2$—C(=O)—)

The protected aeg-PNA was assembled on a Boc-Lys (ClZ) modified MBHA resin with a substitution of approximately 0.10 mmol/g. The synthesis was initiated on 100 mg (dry weight) of t-Boc-Lys(ClZ)-MBHA resin, preswollen overnight in dichloromethane. The bis aeg-PNA was synthesized as per the procedures of Example 55. In step (4) the aeg-pseudoisocytosine monomer of Examples 26 thru 32 (25.1 mg, 0.5 mmol) was used for the incorporation of the aeg-J unit. The bis aeg-PNA was cleaved from the resin as per the procedures of Example 45. Yield: 5.5 mg (purity>90%, purified by RP-HPLC, μBondapak C18). MS(FAB+) m/z: :(found/calcd) 4748/4747.

Using the procedures of this Example the following additional egl linked Bis aeg-PNAs Having Pseudoisocytosine (J), were synthesized:

H-TTJ-TJJ-TT-egl-egl-egl-TTC-CTC-TT-Lys-NH$_2$ (SEQ ID NO:42);
H-TTJ-JJT-TT-egl-egl-egl-TTT-JJJ-TT-Lys-NH$_2$ (SEQ ID NO:43);
H-TTJ-TJJ-TTT-egl-egl-egl-TTT-CCT-CTT-NH$_2$ (SEQ ID NO:44);
H-TTT-JJT-T-egl-egl-egl-TTC-CTT-T-NH$_2$ (SEQ ID NO:45);
H-TTT-TJJ-TJT-J-egl-egl-egl-CTC-TCC-TTT-T-Lys-NH$_2$ (SEQ ID NO:46);
H-TTT-TJJ-TJT-JJJ-TJT-egl-egl-egl-TCT-CCC-TCT-CCT-TTT-Lys-NH$_2$ (SEQ ID NO:47);
H-TTJ-TTJ-TTT-T-egl-egl-egl-TTT-TCT-TCT-T-Lys-NH$_2$ (SEQ ID NO:48);
H-CTT-TTT-TCT-T-egl-egl-egl-TTJ-TTT-TTT-J-Lys-NH$_2$ (SEQ ID NO:49);
H-CTC-TTC-TTT-C-egl-egl-egl-JTT-TJT-TJT-J-Lys-NH$_2$ (SEQ ID NO:50).

EXAMPLE 56a aeg-PNA Having Pseudoisocytosine (J) H-T$_3$JTJT-Lys-NH$_2$ (SEQ ID NO:51) (egl=—NH—CH$_2$—CH$_2$—O—CH$_2$—CH$_2$—O—CH$_2$—C(=O)—)

The title compound was synthesized according to the procedures in Example 56. No linker was incorporated for this aeg-PNA having the pseudoisocytosine (J) base.

EXAMPLE 57 egl Linked Bis aeg-PNA Having Pseudoisocytosine (J) H-TCT-CTT-T-egl-egl-egl-TTT-JTJ-T-Lys-NH$_2$ (SEQ ID NO:52) (egl=—NH—CH$_2$—CH$_2$—O—CH$_2$—CH$_2$—O—CH$_2$—C(=O)—)

The protected aeg-PNA was assembled on a Boc-Lys (ClZ) modified MBHA resin with a substitution of approximately 0.10 mmol/g. The synthesis was initiated on 100 mg (dry weight) of t-Boc-Lys(ClZ)-MBHA resin, preswollen overnight in dichloromethane. The bis aeg-PNA was synthesized as per the procedures of Example 55. In step (4) aeg-pseudoisocytosine monomer of Examples 26 thru 32 (25.1 mg, 0.5 mmol) was used for the incorporation of the aeg-pseudoisocytosine unit. The bis aeg-PNA was cleaved from the resin as per the procedures of Example 45. Yield: 2.8 mg (purity >90%, purified by RP-HPLC, μBondapak C18). MS(FAB+) m/z: :(found/calcd) 4749/4747.

EXAMPLE 58

Synthesis of aeg-PNA H-TCT-CTT-T-Lys-NH$_2$ (SEQ ID NO:53)

The title aeg-PNA was synthesized as per the procedures of Example 45.

EXAMPLE 59 aeg-PNA Oligomer Having Pseudoisocytosine (J), and Pseudouridine (ΨU), H-GΨUA-GAΨU-JAJ-ΨU-Lys-NH$_2$ (SEQ ID NO:54)

The protected aeg-PNA oligomer was assembled on a Boc-Lys(ClZ) modified MBHA resin with a substitution of approximately 0.10 mmol/g. The synthesis was initiated on 100 mg (dry weight) of t-Boc-Lys(ClZ)-MBHA resin, preswollen overnight in dichloromethane. The aeg-PNA oligomer was synthesized as per the procedures of Example 55. In step (4) aeg-pseudoisocytosine monomer of Examples 26 thru 32 (25.1 mg, 0.5 mmol) and the aeg-pseudouracil monomer of Examples 33 thru 36 (19.2 mg, 0.5 mmol) were used for the incorporation of the aeg-pseudoisocytosine and aeg-pseudouracil monomeric units. The aeg-PNA was cleaved from the resin as per the procedures of Example 45. Yield: 5.8 mg (purity >90%, purified by RP-HPLC, μBondapak C18). MS(FAB+) m/z: (found/calcd) 2811/2811

EXAMPLE 60 aeg-PNA Oligomer Having aeg-Isocytosine (aeg-iC), and aeg-Pseudoisocytosine (aeg-J) H-TiCC-iCTC-JCT-J-Lys-NH$_2$ (SEQ ID NO:55)

The protected aeg-PNA was assembled on a Boc-Lys (ClZ) modified MBHA resin with a substitution of approximately 0.10 mmol/g. The synthesis was initiated on 100 mg (dry weight) of t-Boc-Lys(ClZ)-MBHA resin, preswollen overnight in dichloromethane. The aeg-PNA-oligomer was synthesized as per the procedures of Example 45. In step (4) aeg-pseudoisocytosine monomer from Examples 26 thru 32 (25.1 mg, 0.5 mmol) and the aeg-isocytosine monomer from Examples 37 thru 40 (25.1 mg, 0.5 mmol) were used for the incorporation of the aeg-pseudoisocytosine and the aeg-isocytosine monomeric units. The aeg-PNA was cleaved from the resin as per the procedures of Example 45. Yield: 5.8 mg (purity >90%, purified by RP-HPLC, μBondapak C18). MS(FAB+) m/z: (found/calcd) 2702/2701

EXAMPLE 61

Thermal Stability of Bis PNA

The title aeg-PNA from Example 58 and the title bis aeg-PNA from Examples 55, 56 and 57 were used in a study to determine the thermal stability of (PNA)$_2$/DNA triplex formation relative to oligonucleotide targets at pH 5, 7 and 9. The deoxyoligonucleotides used as the targets were: I-CGC-AGA-GA3C-GC; and II-CGC-A3GA-GAC-GC. These target molecules are antiparallel.

The study was carried out in 100 mM NaCl, 10 mM Na-phosphate, 0.1 mM EDTA. The heating rate was 0.5° C./min at 5–90° C.

The PNA and each bis PNA was independently bound to each of the targets and the Tm was determined at each of the pH ranges. The results are tabulated below.

| Sequence | pH | Target I | Target II |
|---|---|---|---|
| Compound A | 5 | 69.0° C. | 68.5° C. |
| H-TCT-CTT-T-egl-egl-egl- | 7 | 49.0° C. | 52.0° C. |
| TTT-CTC-T-Lys-NH$_2$ | 9 | 38.5° C. | 41.0° C. |
| (SEQ ID NO:38) | | | |
| Compound B | 5 | 67.0° C. | 65.0° C. |
| H-TJT-JTT-T-ogl-eg-egl | 7 | 64.0° C. | 48.5° C. |
| TTT-CTC-T-Lys-NH$_2$ | 9 | 60.5° C. | 39.0° C. |
| (SEQ ID NO:41) | | | |
| Compound C | 5 | 66.0° C. | 61.5° C. |
| H-TCT-CTT-T-egl-egl-egl- | 7 | 47.0° C. | 60.0° C. |
| TTT-JTJ-T-Lys-NH$_2$ | 9 | 37.5° C. | 59.0° C. |
| (SEQ ID NO:52) | | | |
| Compound D | 5 | 50.0° C. | 55.5° C. |
| H-TCT-CTT-T-Lys-NH$_2$ | 7 | 40.0° C. | 39.0° C. |

-continued

| Sequence | pH | Target I | Target II |
|---|---|---|---|
| (SEQ ID NO:53) | 9 | — | 23.5° C. |
| Compound E | 5 | 46.0° C. | 48.5° C. |
| H-T$_3$JTJT-LysNH$_2$ | 7 | 36.0° C. | 44.0° C. |
| (SEQ ID NO:51) | 9 | 37.0° C. | 42.5° C. |
| plus Compound D | | | |

The results of the study clearly show that a small but significant increase in Tm is obtained by linking the two PNA together. This is shown by comparing the results obtained for Compound A with the results obtained for Compound D. The study also shows that no major difference is observed when comparing DNA targets of opposite polarity.

The Tms of the compounds studied show a strong pH dependence for compounds that do not have pseudoisocytosine in the parallel hoogsteen strand. This pH dependence is accounted for by the necessary protonation of the cytosine in the Hoogsteen strand. This protonation is not necessary with the pseudoisocytosine for binding to occur.

In compound B the cytosines in one of the linked strands of the compound were replaced by pseudoisocytosines and in Compound C the cytosines in the other strand of the linked strands were similarly substituted, to study the effect of pH on the thermal stability of the triplexes formed. These PNA showed thermal stability at acidic pH (5) comparable to that of bis PNA compound A. However in the complexes where the cytosine containing portion of the compound is anti-parallel to the DNA target (and thus the pseudoisocytosine strand is parallel) almost no pH dependence of the Tm is observed. This was observed in Compound B with target I and Compound C with target II. These results indicate that the orientation directs the complex formation (anti-parallel→Watson/Crick). The pH dependence shown for Compound B with target II and Compound C with target I shows that the cytosine strands of these compounds are involved in Hoogsteen hydrogen binding. Compounds A thru C showed a very fast rate of formation upon cooling. This lack of a pronounced hysterisis in the melting behavior that is normally observed with two single strands of PNA binding to DNA is ascribed to the high local concentration of the now covalently linked second PNA strand.

EXAMPLE 62

Effect of Base Pair Mismatches on bis-PNA/DNA, aeg-PNA$_2$/DNA Thermal Stabilities (Tm)

Three of the aeg-PNA studied in Example 61, Compound C H-TCT-CTT-T-egl-egl-egl-TTT-JTJ-T-Lys-NH$_2$ (SEQ ID NO:52) (PNA-C), Compound D H-TCT-CTT-T-Lys-NH$_2$ (SEQ ID NO:53) (PNA-D) and Compound E H-T$_3$JTJT-LysNH$_2$ (SEQ ID NO:51) (PNA-E) were studied to determine the effect of binding to an oligonucleotides target containing a mismatch.

| Oligonucleotide | PNA-C | PNA-D + PNA-E |
|---|---|---|
| 5'-dCGC-A$_3$-GAG-ACG-C-3' | 60.0° C. | 44.0° C. |
| (SEQ ID NO:56) | | |
| 5'-dCGC-A$_3$-CAG-ACG-C-3' | 27.0° C. | 32.5° C. |
| (SEQ ID NO:57) | | |

-continued

| Oligonucleotide | PNA-C | PNA-D + PNA-E |
|---|---|---|
| 5'-dCGC-A<sub>3</sub>-AGA-GAC-GC-3' (SEQ ID NO:58) | 36.5° C. | 34.0° C. |
| 5'-dCGC-A<sub>3</sub>-TAG-ACG-C-3 (SEQ ID NO:59) | 23.0° C. | 33.0° C. |
| 5'-dCGC-A<sub>3</sub>-CAC-ACG-C-3' (SEQ ID NO:60) | ≦11.0° C. | ≦11.0° C. |

The sequence discrimination of the bis PNA (PNA-C) as judged from thermal stability measurements suffers a very high cost in stability (30° C. for a base mismatch), reflecting the two-fold recognition process involving both PNA strands.

EXAMPLE 63

Strand Displacement Binding of Bis aeg-PNA's

A $^{32}$P-end labeled EcoRI-PvuII fragment of the plasmid pTHa$^{12}$ was incubated with aeg-PNA in 100 µl 10 mM Na-phosphate, 1 mM EDTA, pH 7 for 60 minutes at 20° C., and subsequently treated with KMnO$_4$ (20 mM for 15 sec). Following precipitation and treatment with piperidine the samples were analyzed by electrophoresis in polyacrylamide sequencing gels and the radioactive DNA bands visualized by autoradiography. The following concentrations of PNA were used: 1 µM, 3 µM, 10 µM, and 30 µM, and the PNAs were compounds A, B, C and D from Example 61. A control was also run which contained no PNA.

The results show the fragments expected for strand displacement.

EXAMPLE 64

Binding Affinity of Bis aeg-PNA

In order to study the binding properties of bis aeg-PNA's as compared to that of the unlinked aeg-PNA's the following aeg-PNA's and bis aeg-PNA'S were synthesized:

| | |
|---|---|
| Compound A | H$_2$N-TTCTCTCTCT-CONH$_2$ (SEQ ID NO:61) |
| Compound B | H$_2$N-gly-TCTCTCTCTT-lys-CONH$_2$ (SEQ ID NO:62) |
| Compound C | H$_2$N-gly-TTCTCTCTCT-lys-Aha-lys-Aha-lys-TCTCTCTCTT-lys-CONH$_2$ (SEQ ID NO:27) |
| Compound D | H$_2$N-gly-TTCTCTCTCT-egl-egl-egl-TCTCTCTCTT-lys-CONH$_2$ (SEQ ID NO:63) |

Two standard 10 mer aeg-PNA's were synthesized opposite in orientation e.g. antiparallel (compounds A and B), as per the procedures of Example 45, and two bis aeg-PNAs were synthesized with two 10 mer sequences linked together via linking moieties. One of the bis aeg-PNAs (Compound C) was linked using Aha and lys groups previously described in Example 47. The other bis aeg-PNA (Compound D) was linked using poly ethylene glycol linking moieties described in Example 55. The bis aeg-PNAs are identical except for the linking moieties.

Dissociation constants ($K_d$s) for duplex DNA strand invasion were determined for each bis aeg-PNA, each single aeg-PNA and an equimolar mixture of the single aeg-PNAs. Hybridization was for 4 days at 37° C. in 100 mM Na$^+$ (1× TMTB). The DNA targets were 65 mer duplexes containing the complementary sequence in opposite orientations.

The Aha linked bis aeg-PNA (Compound C), bound duplex DNA about 500 times better than the best single aeg-PNA (Compound B). The PEG linked bis aeg-PNA bound as well as the best single aeg-PNA (Compound B). The observed orientation of bis binding was with the Aha linker crossing the 5' end of the triplex. Bis binding to single stranded RNA and DNA targets was also evaluated and compared to individual aeg-PNAs. The Aha linked bis aeg-PNA bound ssDNA more than 100 times better than aeg-PNA. The preferred orientation has the linker crossing the 5' end of the target strand. The individual aeg-PNAs bound ssRNA more than 500 times tighter than ssDNA. The bis aeg-PNA bound ssRNA 3 times better than the best binding single aeg-PNA.

Bis aeg-PNA strand invasion was evaluated in the presence of Mg$^{++}$ and spermine. In previous experiments, Mg$^{++}$ was shown to weaken PNA strand invasion while spermine completely inhibited binding. Mg++ and spermine resulted in weaker binding of Compound C, however detectable strand invasion was observed in the presence of spermine.

The hybridization rate for Compound C invasion of duplex DNA was determined at two concentrations and compared to invasion rates for several single PNAs. Compound C bound 9 times faster than single PNA. The improved strand invasion by bis PNA is associated with a faster on rate. This may be due to the close proximity of the second, triple stranding aeg-PNA to stabilize the strand invaded aeg-PNA in the duplex. The second aeg-PNA may prevent the invaded aeg-PNA from being ejected from the duplex.

To ensure that the above improved binding with bis aeg-PNA (Compound C) was not due to non-specific binding of the Aha linker. Compound C was hybridized with up to 1 µM noncomplementary duplex target. No binding was observed.

EXAMPLE 65

ES/MS of Bis-aeg-PNA:DNA

Compound AATT GTA GAG AGA GAA T (SEQ ID NO:64)

The binding stoichiometry of a bis aeg-PNA and a single stranded DNA were determined by mass spectrometry using a Hewlett-Packard 59987A electrospray unit, 5989A quadrapole mass spectrometer with extended mass range, and a Hewlett Packard 1090 HPLC connected to the electrospray needle via an LC packings 1/100 splitter. Compound A a DNA single strand 16 mer with mass 4991 AMU (8 µM in a 50 mM NH$_4$OAC solution) and Compound C from Example 64, a bis aeg-PNA of mass 6012 (10 µM in a 50 mM NH$_4$OAC solution) were analyzed separately and as a mixture. The sample to be tested as a mixture was taken from the 50 mM stock solutions in NH$_4$Oac, incubated to 37° C. for 72 hours, and cooled to 2° C. for 48hours. The samples are warmed to room temperature prior to testing. 50 µl of the stock each sample and the mixture was mixed with 75 µl of isopropanol and injected into a 50 µl loop which continuously feeds the mass spectrometer. The samples were all analyzed in negative ion mode and a minimum of 16 scans were averaged to determine the masses. The deconvolution of data was performed by Hewlett-Packard's electrospray deconvolution program. The observed mass of the single stranded DNA was 4990 AMU and the observed mass of the bis aeg-PNA was 6012 AMU. The observed mass of the mixture was 11005 AMU which corresponds to one DNA strand and one bis aeg-PNA strand e.g. a 1:1 ratio. The calculated mass for the triplex is 11002 AMU, within 0.03% of the calculated mass of 11005 AMU.

EXAMPLE 66

ES/MS of aeg-PNA$_2$/DNA

The binding stoichiometry of two single aeg-PNAs and a single stranded DNA containing the complimentary sequence, were determined by mass spectrometry using the apparatus of Example 65.

Compound AATT GTA GAG AGA GAA T (SEQ ID NO:64) 8 μM single strand DNA (Compound A) was taken from a 50 mM NH$_4$Oac stock solution and mixed with 20 μM single aeg-PNA (Compound C, Example 64) also taken from a stock solution of 50 mM NH$_4$Oac. The two samples are mixed together and incubated to 37° C. for 72 hours, and cooled to 2° C. for 48 hours. The samples are warmed to room temperature prior to testing. The experimentally found mass of the compound thus formed in the mixture was 10597 Da. The mass of the single aeg-PNA is 2802 and the mass of the single stranded DNA target (Compound A) is 4990 Da. The total of one single stranded DNA and two of the aeg-PNAs is 10594 Da. This mass is the result of two to one stoichiometry e.g. two aeg-PNAs to one DNA.

EXAMPLE 67

Transcription Initiation with Single PNA, Trans PNA and Cis PNA

Restriction fragments of three plasmids pT9C, pT9CT9C (pUC19 derivatives containing respectively the sequences T9C and T9CT9C) and pT9CA9GKS 9bluescript KS+ derivative containing a T9CA9G sequence) were isolated by digestion with PvuII and purification on polyacrylamide gels resulting in fragments of 338 base pairs (pT9C), 354 base pairs (pT9CT9C) and 477 base pairs (pT9CA9GKS). PNA-DNA complexes were formed by incubating PNA with DNA fragments in 10 mM Tris-HCl pH 8.0 and 0.1 mM EDTA in a total volume of 15 μL for 1 hour at 37° C. The reaction mixture was adjusted to contain a final concentration of 40 mM Tris-HCl pH 7.9, 120 mM KCl, 5 mM MgCl$_2$, 011 mM DTT, and 1 mM of ATP, CTP, GTP and 0.1 mM of UTP and 5 μCi $^{32}$p UTP. The PNA used was T9C-lysNH$_2$ in each case.

The three plasmids used provide respectively a single binding site for the PNA (mono), a pair of binding sites on the same DNA strand (cis), and a pair of binding sites on opposite strands of the DNA (trans). Complexes were formed between the PNA's and each of the three plasmids with the PNA concentration at 0 m, 3 nM, 10 nM, 3 μM and 10 μM.

The transcriptions were initiated by addition of 100 nM *E. Coli* RNA polymerase holoenzyme (Boeringer). The mixtures (total volume of 30 μl) were incubated at 37° C. for 20 minutes and the RNA produced by transcription was subsequently recovered by ethanol precipitation. The RNA transcripts were analyzed on 8% denaturing polyacrylamide gels, and visualized by autoradiography.

As viewed on the corresponding gel for the mono at a PNA concentration of 10 μM is the production of a single RNA product having the size expected if transcription occurs at the PNA binding site.

As viewed on the corresponding gel for the cis at a PNA concentration of 10 μM is the production of a single RNA transcript but transcription is shown to be more efficiently promoted by the presence of two oligo PNA's at the binding site arranged in cis.

As viewed on the corresponding gel for the trans PNA at concentrations of 10 nM, 3 μM and 10 μM is the production of two RNA transcripts of the expected sizes if transcription is initiated of each of the two DNA strands and proceeds from the respective binding site to the end of the DNA fragment.

In the gels where transcript RNA is seen, it is estimated that from 1 to 5 RNA molecules are being produced per DNA template molecule.

We claim:

1. A compound comprising a first peptide nucleic acid segment and a second peptide nucleic acid segment, wherein:

said segments are joined via at least one linking segment;

said linking segment is not a peptide nucleic acid or an oligonucleotide; and said peptide nucleic acid segments are of the formula:

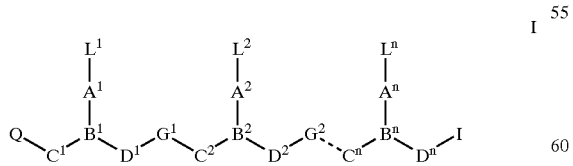

I wherein:

n is at least 2, each of $L^1$–$L^n$ is independently selected from the group consisting of hydrogen, hydroxy, $(C_1$–$C_4)$alkanoyl, naturally occurring nucleobases, non-naturally occurring nucleobases, aromatic moieties, DNA intercalators, nucleobase-binding groups, heterocyclic moieties, and reporter ligands;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$ alkylthio, $NR^3R^4$ and $SR^5$, where $R^3$ and $R^4$ are each independently selected from the group consisting of hydrogen, $(C_1$–$C_4)$alkyl, hydroxy- or alkoxy- or alkylthio-substituted $(C_1$–$C_4)$alkyl, hydroxy, alkoxy, alkylthio and amino, and $R^5$ is hydrogen, $(C_1$–$C_6)$alkyl, hydroxy-, alkoxy-, or alkylthio-substituted $(C_1$–$C_6)$ alkyl, or $R^6$ and $R^7$ taken together complete an alicyclic or heterocyclic system;

each of $D^1$–$D^n$ is $(CR^6R^7)$ where $R^6$ and $R^7$ are as defined above;

each of y and z is zero or an integer from 1 to 10, the sum y+z being greater than 1 but not more than 10;

each of $G^1$–$G^{n-1}$ is —$NR^3CO$—, in either orientation, where $R^3$ is as defined above;

each of $A^1$–$A^n$ and $B^1$–$B^n$ are selected such that:
(a) A is a group of formula (IIa), (IIb), (IIc) or (IId), and B is N or $R^3N^+$; or
(b) A is a group of formula (IId) and B is CH;

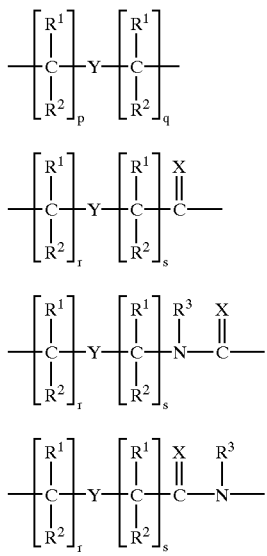

where:
X is O, S, Se, $NR^3$, $CH_2$ or $C(CH_3)_2$;
Y is a single bond, O, S or $NR^4$;
each of p and q is zero or an integer from 1 to 5;
each of r and s is zero or an integer from 1 to 5;
each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and
each $R^3$ and $R^4$ are as defined above;
Q is —$CO_2H$, —CONR'R", —$SO_3H$ or —$SO_2NR'R"$ or an activated derivative of —$CO_2H$ or —$SO_3H$; and
I is —NHR'"R"" or —NR'"C(O)R"", where R', R", R'" and R"" are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

2. A compound of claim 1 wherein said linking segment includes at least one unit of an aminoalkylcarboxylic acid of the formula

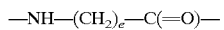

where e is 1 to 15.

3. A compound of claim 2 wherein e is 4 to 8.
4. A compound of claim 2 wherein said linking segment further includes at least one amino acid.
5. A compound of claim 3 wherein e is 5 or 6.
6. A compound of claim 1 wherein said linking segment comprises a compound of the formula

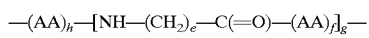

where:
AA is an α-amino acid;
e is 4 to 8;
f and h are 0 or 1; and
g is 1 to 4.

7. A compound of claim 1 wherein said linking segment includes at least one unit of a glycol amino acid.
8. A compound of claim 7 wherein said glycol amino acid comprises glycol sub-units that are linked together in a linear array and that have an amino group on one terminus and a carboxyl group on the other terminus.
9. A compound of claim 1 wherein said linking segment comprises a compound of the formula

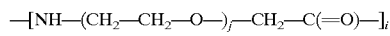

wherein:
j is 1 to 6; and
i is 1 to 6.

10. A compound of claim 9 wherein j is 2 and i is 3.
11. A compound of claim 1 wherein said peptide nucleic acid segments are joined together via two of said linking segments to form a cyclic structure.
12. A compound of claim 1 wherein said linking segment connects a terminal amine function on one of said first and second peptide nucleic acid segments to a carboxyl function on the other of said first and second peptide nucleic acid segments.
13. A compound of claim 12 wherein said first peptide nucleic acid segment has a nucleobase sequence determined in a direction from its amine terminus to its carboxyl terminus, said second peptide nucleic acid segment has a nucleobase sequence determined in a direction from its carboxyl terminus to its amine terminus, and said sequences are the same.
14. A compound of claim 1 wherein at least a portion of nucleobases of said first and second peptide nucleic acid segments are pyrimidine nucleobases.
15. A compound of claim 14 wherein at least one of said pyrimidine nucleobases of one of said first or said second peptide nucleic acid segments comprises a C-pyrimidine heterocyclic base or an iso-pyrimidine heterocyclic base.
16. A compound of claim 14 wherein said portion of said nucleobases that are pyrimidine nucleobases are located in contiguous homopyrimidine sequences.
17. A compound of claim 1 wherein said linking segment comprises a carboxylic acid functional group and a primary amino functional group.
18. A compound of claim 1 wherein said linking segment is of the formula:

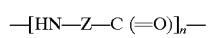

wherein:
n is 1 to 3; and
Z is $C_1$ to $C_{20}$ alkyl, $C_2$ to $C_{20}$ alkenyl, $C_2$ to $C_{20}$ alkynyl, $C_1$ to $C_{20}$ alkanoyl having at least one O or S atom, $C_7$ to $C_{34}$ aralkyl, $C_6$–$C_{14}$ aryl or an amino acid.

19. A multiple stranded structure comprising:
a nucleic acid strand, at least a portion of which forms a target nucleotide sequence; and
a further strand, said further strand including first and second peptide nucleic acid segments that are joined together via a linker;
wherein:
said first peptide nucleic acid segment has a nucleobase sequence that is complementary to the target nucleotide sequence in the 5' to 3' direction of said target nucleotide sequence;
said second peptide nucleic acid segment has a nucleobase sequence that is complementary to the target nucleotide sequence in the 3' to 5' direction of said target nucleotide sequence; and said peptide nucleic acid segments are of the formula:

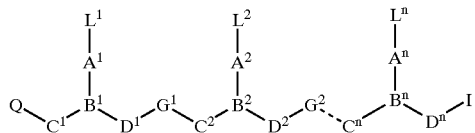

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, provided that at least one of said $L^1$–$L^n$ is a C-pyrimidine heterocyclic base or an iso-pyrimidine heterocyclic base;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are each independently selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio and amino, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $(CR^6R^7)_z$ where $R^6$ and $R^7$ are as defined above;

each of y and z is zero or an integer from 1 to 10, the sum y+z being greater than 1 but not more than 10;

each of $G^1$–$G^{n-1}$ is —$NR^3CO$—, in either orientation, where $R^3$ is as defined above;

each of $A^1$–$A^n$ and $B^1$–$B^n$ are selected such that:

(a) A is a group of formula (IIa), (IIb), (IIc) or (IId), and B is N or $R^3N^+$; or (b) A is a group of formula (IId) and B is CH;

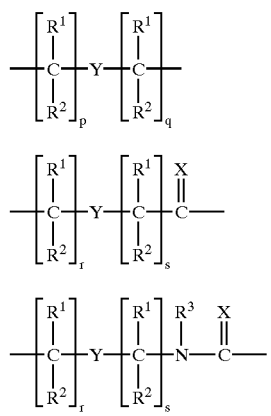

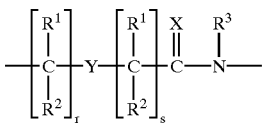

where:

X is O, S, Se, $NR^3$, $CH_2$ or $C(CH_3)_2$;

Y is a single bond, O, S or $NR^4$;

each of p and q is zero or an integer from 1 to 5;

each of r and s is zero or an integer from 1 to 5;

each $R^1$ and $R^2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and each $R^3$ and $R^4$ are as defined above;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

20. The structure of claim 19 wherein said nucleic acid strand is a single stranded DNA or RNA.

21. The structure of claim 19 wherein said nucleic acid strand is a double stranded DNA.

22. The structure of claim 19 wherein one of said first or second peptide nucleic acid segments exhibits Watson/Crick binding to said target nucleotide sequence and the other of said first and second peptide nucleic acid segments exhibits Hoogsteen binding to said target nucleotide sequence.

23. The structure of claim 22 wherein said one of said first or second peptide nucleic acid segments that exhibits Hoogsteen binding to said target nucleotide sequence includes C-pyrimidine heterocyclic nucleobases or iso-pyrimidine heterocyclic nucleobases in at least one of the positions that are complementary to nucleobases in said target nucleotide sequence.

24. The structure of claim 23 wherein said C-pyrimidine heterocyclic nucleobase or iso-pyrimidine heterocyclic nucleobase is pseudo-isocytosine, iso-cytosine, pseudo-uracil or 5-bromouracil.

25. A compound comprising a peptide nucleic acid strand of the formula:

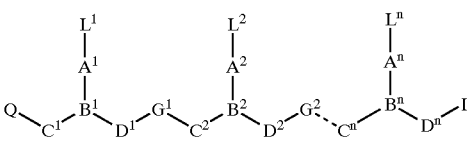

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, provided that at least one of said $L^1$–$L^n$ is pseudo-uracil;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$alkylthio, $NR^3R^4$ and $SR^5$, where $R^3$ and $R^4$ are eac independently selected from the group consisting of hydrogen, $(C_1$–$C_4)$alkyl, hydroxy- or alkoxy- or alkylthio-substituted $(C_1$–$C_4)$ alkyl, hydroxy, alkoxy, alkylthio and amino, and $R^5$ is hydrogen, $(C_1$–$C_6)$alkyl, hydroxy-, alkoxy-, or alkylthio-substituted $(C_1$–$C_6)$alkyl, or $R^6$ and $R^7$ taken together complete an alicyclic or heterocyclic system;

each of $D^1$–$D^n$ is $(CR^6R^7)_2$ where $R^6$ and $R^7$ are as defined above;

each of y and z is zero or an integer from 1 to 10, the sum y+z being greater than 1 but not more than 10;

each of $G^1$–$G^{n-1}$ is —$NR^3CO$—, in either orientation, where $R^3$ is as defined above;

each of $A^1$–$A^n$ and $B^1$–$B^n$ are selected such that:
(a) A is a group of formula (IIa), (IIb), (IIc) or (IId), and B is N or $R^3N^+$; or
(b) A is a group of formula (IId) and B is CH;

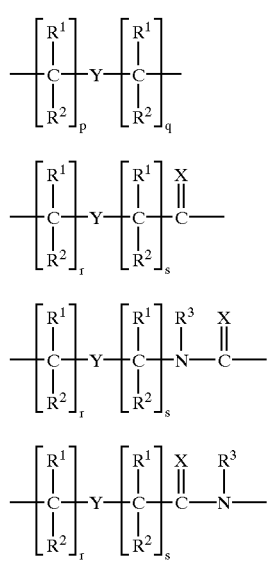

(IIa)

(IIb)

(IIc)

(IId)

where:
X is O, S, Se, $NR^3$, $CH_2$ or $C(CH_3)_2$;
Y is a single bond, O, S or $NR^4$;
each of p and q is zero or an integer from 1 to 5;
each of r and s is zero or an integer from 1 to 5;
each $R^1$ and $R^2$ is independently selected from the group consisting of hydrogen, $(C_1$–$C_4)$alkyl which may be hydroxy- or alkoxy- or alkylthio-substituted, hydroxy, alkoxy, alkylthio, amino and halogen; and
each $R^3$ and $R^4$ are as defined above;
Q is —$CO_2H$, —$CONR'R''$, —$SO_3H$ or —$SO_2NR'R''$ or an activated derivative of —$CO_2H$ or —$SO_3H$; and
I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

26. A compound comprising a peptide nucleic acid strand of the formula:

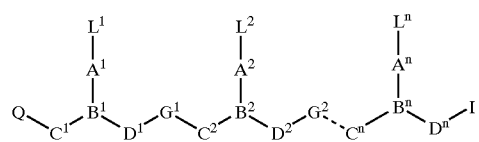

I wherein:

n is at least 2, each of $L^1$–$L^n$ is independently selected from the group consisting of hydrogen, hydroxy, $(C_1$–$C_4)$alkanoyl, naturally occurring nucleobases, non-naturally occurring nucleobases, aromatic moieties, DNA intercalators, nucleobase-binding groups, heterocyclic moieties, and reporter ligands, provided that at least one of said $L^1$–$L^n$ is 5-bromouracil;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, $(C_2$–$C_6)$alkyl, aryl, aralkyl, heteroaryl, hydroxy, $(C_1$–$C_6)$alkoxy, $(C_1$–$C_6)$alkylthio, $NR^3R^4$ and $SR^5$, where $R^3$ and $R^4$ are each independently selected from the group consisting of hydrogen, $(C_1$–$C_4)$alkyl, hydroxy- or alkoxy- or alkylthio-substituted $(C_1$–$C_4)$ alkyl, hydroxy, alkoxy, alkylthio and amino, and $R^5$ is hydrogen, $(C_1$–$C_6)$alkyl, hydroxy-, alkoxy-, or alkylthio-substituted $(C_1$–$C_6)$alkyl, or $R^6$ and $R^7$ taken together complete an alicyclic or heterocyclic system;

each of $D^1$–$D^n$ is $(CR^6R^7)_z$ where $R^6$ and $R^7$ are as defined above;

each of y and z is zero or an integer from 1 to 10, the sum y+z being greater than 1 but not more than 10;

each of $G^1$–$G^{n-1}$ is —$NR^3CO$—, in either orientation, where $R^3$ is as defined above;

each of $A^1$–$A^n$ and $B^1$–$B^n$ are selected such that:
(a) A is a group of formula (IIa), (IIb), (IIc) or (IId), and B is N or $R^3N^+$; or
(b) A is a group of formula (IId) and B is CH;

(IIa)

(IIb)

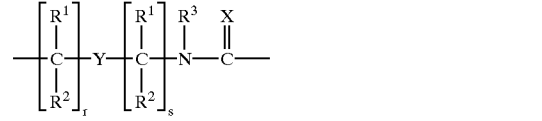

(IIc)

-continued

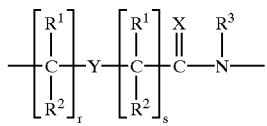

(IId)

where:
X is O, S, Se, $NR^3$, $CH_2$ or $C(CH_3)_2$;
Y is a single bond, O, S or $NR^4$;
each of p and q is zero or an integer from 1 to 5;
each of r and s is zero or an integer from 1 to 5;
each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and each $R^3$ and $R^4$ are as defined above;

Q is $-CO_2H$, $-CONR'R''$, $-SO_3H$ or $-SO_2NR'R''$ or an activated derivative of $-CO_2H$ or $-SO_3H$; and I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

* * * * *